(12) United States Patent
Parham et al.

(10) Patent No.: US 9,337,430 B2
(45) Date of Patent: May 10, 2016

(54) ORGANIC ELECTROLUMINESCENT DEVICE

(71) Applicant: Merck Patent GmbH, Darmstadt (DE)

(72) Inventors: Amir Hossain Parham, Frankfurt am Main (DE); Christof Pflumm, Darmstadt (DE); Anja Jatsch, Frankfurt am Main (DE); Thomas Eberle, Landau (DE); Philipp Stoessel, Frankfurt am Main (DE)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 14/355,342

(22) PCT Filed: Oct. 11, 2012

(86) PCT No.: PCT/EP2012/004255
§ 371 (c)(1),
(2) Date: Apr. 30, 2014

(87) PCT Pub. No.: WO2013/064206
PCT Pub. Date: May 10, 2013

(65) Prior Publication Data
US 2014/0249308 A1 Sep. 4, 2014

(30) Foreign Application Priority Data
Nov. 1, 2011 (EP) .................................... 11008708

(51) Int. Cl.
| | | |
|---|---|---|
| C07D 251/00 | (2006.01) |
| H01L 51/00 | (2006.01) |
| C07D 471/06 | (2006.01) |
| C09K 11/06 | (2006.01) |
| C07D 401/14 | (2006.01) |
| C07D 405/14 | (2006.01) |
| C07D 221/10 | (2006.01) |
| C07D 221/18 | (2006.01) |
| C07D 221/20 | (2006.01) |
| C07D 401/04 | (2006.01) |
| C07D 401/10 | (2006.01) |
| C07D 405/04 | (2006.01) |
| C07D 405/10 | (2006.01) |
| C07D 413/10 | (2006.01) |
| C07D 417/04 | (2006.01) |
| C07D 471/04 | (2006.01) |
| C07D 471/14 | (2006.01) |
| C07D 471/22 | (2006.01) |
| C07D 491/04 | (2006.01) |
| C07D 491/06 | (2006.01) |
| C07D 491/22 | (2006.01) |
| C07D 495/04 | (2006.01) |
| C07D 495/06 | (2006.01) |
| C07D 495/22 | (2006.01) |
| H05B 33/10 | (2006.01) |

(52) U.S. Cl.
CPC .......... *H01L 51/0058* (2013.01); *C07D 221/10* (2013.01); *C07D 221/18* (2013.01); *C07D 221/20* (2013.01); *C07D 401/04* (2013.01); *C07D 401/10* (2013.01); *C07D 401/14* (2013.01); *C07D 405/04* (2013.01); *C07D 405/10* (2013.01); *C07D 405/14* (2013.01); *C07D 413/10* (2013.01); *C07D 417/04* (2013.01); *C07D 471/04* (2013.01); *C07D 471/06* (2013.01); *C07D 471/14* (2013.01); *C07D 471/22* (2013.01); *C07D 491/04* (2013.01); *C07D 491/06* (2013.01); *C07D 491/22* (2013.01); *C07D 495/04* (2013.01); *C07D 495/06* (2013.01); *C07D 495/22* (2013.01); *C09K 11/06* (2013.01); *H01L 51/0061* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/0094* (2013.01); *H05B 33/10* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1037* (2013.01); *C09K 2211/1044* (2013.01); *C09K 2211/1059* (2013.01); *C09K 2211/1088* (2013.01); *C09K 2211/1092* (2013.01)

(58) Field of Classification Search
None
See application file for complete search history.

(56) References Cited

U.S. PATENT DOCUMENTS

| | | |
|---|---|---|
| 6,004,971 A | 12/1999 | Grese et al. |
| 2007/0265296 A1 | 11/2007 | Dalton et al. |
| 2013/0012700 A1 | 1/2013 | Parham et al. |

FOREIGN PATENT DOCUMENTS

| | | |
|---|---|---|
| DE | 102010012738 A1 | 9/2011 |
| EP | 0761669 A2 | 3/1997 |
| EP | 2357177 A1 | 8/2011 |
| GR | 3035253 T3 | 4/2001 |

(Continued)

OTHER PUBLICATIONS

Ferraccioli, R. et al., J. Amer. Chem. Soc. (2006) vol. 128(3), 722-723.*

(Continued)

*Primary Examiner* — Heidi Reese
(74) *Attorney, Agent, or Firm* — Drinker Biddle & Reath LLP

(57) ABSTRACT

The present invention relates to electronic devices, in particular organic electroluminescent devices, comprising compounds of the formula (1), to the corresponding compounds, and to a process for the preparation of these compounds.

11 Claims, No Drawings

(56) References Cited

FOREIGN PATENT DOCUMENTS

| JP | 7244392 A | 9/1995 |
|---|---|---|
| JP | 11514347 A | 7/1999 |

OTHER PUBLICATIONS

Demeter, A., et al., "Dual Fluorescence and Intramolecular Charge Transfer with N-Phenylphenanthridinones", Journal of Physical Chemistry A, vol. 105, No. 19, (2001), pp. 4611-4621.

Demeter, A., et al., "Dual luminescence properties of differently benzo-fused N-phenylphenanthridinones", Photochemical and Photobiological Sciences, vol. 2, No. 3, (2003), pp. 273-281.

Donati, L., et al., "Solvent/Base Effects in the Selective Domino Synthesis of Phenanthridinones That Involve High-Valent Palladium Species: Experimental and Theoretical Studies", Chemistry European Journal, vol. 17, No. 45, (2011), pp. 12809-12819.

Gomez-Lor, B., et al., "Synthesis of a Triaza Analogue of Crushed-Fullerene by Intramolecular Palladium-Catalyzed Arylation", Organic Letters, vol. 6, No. 17, pp. 2993-2996.

Grese, T., et al., "Photochemical Synthesis of N-Arylbenzophenanthridine Selective Estrogen Receptor Modulators (SERMs)", Journal of Medicinal Chemistry, vol. 44, No. 17, (2001), pp. 2857-2860.

Hey, D.H., et al., "Internuclear Cyclisation. Part XIII. The Decomposition of Diazonium Salts prepared from N-o-Aminobenzoyldiphenylamines. A New Molecular Rearrangement.", Journal of the Chemical Society, (1959), pp. 1563-1572.

Li, B., et al., "One-pot synthesis of benzo[α]phenanthridin-5-ones by photoinduced cycloaddition of 3-chloroisoquinolin-1-ones with styrenes", Tetrahedron Letters, vol. 51, No. 29, (2010), pp. 3748-3751.

Wang, R., et al., "One-pot synthesis of benzo[f]quinolin-3-ones and benzo[α]phenanthridein-5-ones by the photoanuulation of 6-chloropyridin-2-ones and 3-chloroisoquinolin-1-ones to phenylacetylene", Organic and Biomolecular Chemistry, vol. 9, No. 16, (2011), pp. 5802-5808.

International Search report of PCT/EP2012/004255 mailed Jan. 30, 2013.

\* cited by examiner

ORGANIC ELECTROLUMINESCENT DEVICE

CROSS-REFERENCE TO RELATED APPLICATIONS

This application is a national stage application (under 35 U.S.C. §371) of PCT/EP2012/004255, filed Oct. 11, 2012, which claims benefit of European Application No. 11008708.7, filed Nov. 1, 2011, both of which are incorporated herein by reference in their entirely.

The present invention relates to electronic devices, in particular organic electroluminescent devices, to materials for use in electronic devices, in particular in organic electroluminescent devices, and to a process for the preparation of these materials The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organometallic complexes which exhibit phosphorescence instead of fluorescence. For quantum-mechanical reasons, an up to four-fold quantum and power efficiency is possible using organometallic compounds as phosphorescence emitters. In general, there is still a need for improvement, for example with respect to efficiency, operating voltage and lifetime, in the case of OLEDs, in particular also in the case of OLEDs which exhibit triplet emission (phosphorescence). This applies, in particular, to OLEDs which emit in the relatively short-wave region, for example green.

The properties of phosphorescent OLEDs are determined not only by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties. There is still a need for improvement in the case of these materials for fluorescent OLEDs too.

In accordance with the prior art, use is made, inter alia, of ketones (for example in accordance with WO 2004/093207 or WO 2010/006680) as matrix materials for phosphorescent emitters. However, there is still a need for improvement, in particular in relation to the efficiency and the lifetime of the device, on use of these matrix materials, as in the case of other matrix materials.

In accordance with the prior art, carbazole derivatives, for example in accordance with WO 2005/039246, US 2005/0069729, JP 2004/288381, EP 1205527 or WO 2008/086851, and indolocarbazole derivatives, for example in accordance with WO 2007/063754 or WO 2008/056746, are furthermore employed as matrix materials for phosphorescent emitters in organic electroluminescent devices. These are in some cases electrochemically unstable, which results in side reactions in the organic electroluminescent device. Further improvements are desirable here, likewise in relation to the efficiency, the lifetime and the thermal stability of the materials.

The object of the present invention is the provision of compounds which are suitable for use in a fluorescent or phosphorescent OLED, in particular a phosphorescent OLED, for example as matrix material or as hole-transport/electron-blocking material or exciton-blocking material or as electron-transport or hole-blocking material. In particular, it is the object of the present invention to provide matrix materials which are suitable for green-, red- and optionally also blue-phosphorescent OLEDs.

Surprisingly, it has been found that the compounds described in greater detail below achieve this object and result in improvements in the organic electroluminescent device, in particular with respect to the lifetime, the efficiency and/or the operating voltage. This applies, in particular, to red- and green-phosphorescent electroluminescent devices, especially on use of the compounds according to the invention as matrix material. The materials are furthermore distinguished by high oxidation stability in solution and by high temperature stability. The present invention therefore relates to electronic devices, in particular organic electroluminescent devices, which comprise compounds of this type.

The present invention relates to an electronic device comprising a compound of the formula (1),

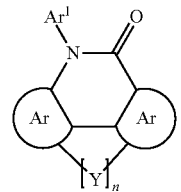

formula (1)

where the following applies to the symbols and indices used:

Ar is on each occurrence, identically or differently, an aryl or heteroaryl group having 5 to 13 aromatic ring atoms, which may be substituted by one or more radicals R;

$Ar^1$ is an aromatic or heteroaromatic ring system having 5 to 24 aromatic ring atoms, which may be substituted by one or more radicals R and which contains no aryl or heteroaryl groups having more than two aromatic six-membered rings condensed directly onto one another;

Y is —C(=O)—N($Ar^1$)—, —C(=O)—O—, —$CR^1$=$CR^1$—, —$CR^1$=N—, $C(R^1)_2$, $NR^1$, O, S, C(=O), C(=S), C(=$NR^1$), C(=C($R^1)_2$), $Si(R^1)_2$, $BR^1$, $PR^1$, P(=O)$R^1$, SO or $SO_2$;

R, $R^1$ is selected on each occurrence, identically or differently, from the group consisting of H, D, F, Cl, Br, I, CN, $NO_2$, $N(Ar^2)_2$, $N(R^2)_2$, C(=O)$Ar^2$, C(=O)$R^2$, P(=O) $(Ar^2)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent $CH_2$ groups may be replaced by $R^2C$=$CR^2$, C≡C, $Si(R^2)_2$, C=O, C=S, C=$NR^2$, P(=O)($R^2$), SO, $SO_2$, $NR^2$, O, S or $CONR^2$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^2$, an aryloxy or heteroaryloxy group having 5 to 60 aromatic ring atoms, which may be substituted by one or more radicals $R^2$, or a combination of these systems, where two or more adjacent substituents R or two or more adjacent substituents $R^1$ may optionally form a monocyclic or polycyclic, aliphatic, aromatic or heteroaromatic ring system, which may be substituted by one or more radicals $R^2$ and which contains no aryl or heteroaryl groups having more than two aromatic six-membered rings condensed directly onto one another; a radical R on $Ar^1$ may furthermore also form an aliphatic ring system with a radical R on Ar; with the proviso that an aryl or heteroaryl group having more than two aryl groups condensed directly onto one another is not formed by ring formation of the radicals R or $R^1$;

$Ar^2$ is on each occurrence, identically or differently, an aromatic or heteroaromatic ring system having 5-30 aromatic ring atoms, which may be substituted by one or more non-aromatic radicals $R^2$ and which contains no aryl or heteroaryl groups having more than two aromatic six-membered rings condensed directly onto one another; two radicals $Ar^2$ which are bonded to the same N atom or P atom may also be bridged to one another here by a single bond or a bridge selected from $N(R^2)$, $C(R^2)_2$ or O;

$R^2$ is selected from the group consisting of H, D, F, CN, an aliphatic hydrocarbon radical having 1 to 20 C atoms, an aromatic or hetero-aromatic ring system having 5 to 30 aromatic ring atoms, in which one or more H atoms may be replaced by D, F, Cl, Br, I or CN, where two or more adjacent substituents $R^2$ may form a mono- or polycyclic, aliphatic, aromatic or heteroaromatic ring system with one another;

n is on each occurrence, identically or differently, 0 or 1, where n=0 means that no group Y is present and instead a substituent R is bonded or a heteroatom of the group Ar is present in the positions on Ar in which Y is bonded in formula (1);

with the proviso that the radicals on Ar or $Ar^1$ do not contain a lactam group.

An electronic device in the sense of the present invention is a device which comprises at least one layer which comprises at least one organic compound. The component may, however, also comprise inorganic materials or also layers which are built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells (O-DSSC), organic optical detectors, organic photoreceptors, organic field-quench devices (O-FQDs), light-emitting electrochemical cells (LECs), organic laser diodes (O-lasers) and "organic plasmon emitting devices" (D. M. Koller et al., *Nature Photonics* 2008, 1-4), preferably organic electroluminescent devices (OLEDs) and particularly preferably phosphorescent OLEDs.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (anellated) aryl or heteroaryl group, for example naphthalene, anthracene, phenanthrene, quinoline, isoquinoline, etc. Aromatic groups which are linked to one another by a single bond, such as, for example, biphenyl, are, by contrast, not referred to as aryl or heteroaryl group, but instead as aromatic ring system.

An aromatic ring system in the sense of this invention contains 6 to 80 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be connected by a non-aromatic unit, such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are connected, for example, by a short alkyl group.

An aryl or heteroaryl group having not more than two aromatic six-membered rings condensed directly onto one another is taken to mean simple aryl or hetero-aryl groups, such as, for example, benzene or pyridine, or aryl or heteroaryl groups having precisely two aromatic six-membered rings condensed onto one another, such as, for example, naphthalene or quinoline. This is furthermore taken to mean heteroaryl groups in which aromatic five-membered rings and six-membered rings, but not aromatic six-membered rings, are condensed directly onto one another, such as, for example, carbazole, dibenzofuran, dibenzothiophene or benzimidazole.

For the purposes of the present invention, an aliphatic hydrocarbon radical or an alkyl group or an alkenyl or alkynyl group, which may contain 1 to 40 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methyl-butoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5-60 aromatic ring atoms, which may also in each case be substituted by the above-mentioned radicals $R^2$ or a hydrocarbon radical and which may be linked to the aromatic or heteroaromatic ring system via any desired positions, is taken to mean, in particular, groups derived from benzene, naphthalene, anthracene, phenanthrene, pyrene, benzanthracene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diaza-pyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combination of these systems.

Adjacent radicals R or $R^1$ in the sense of the present invention are taken to mean radicals which are bonded to carbon atoms which are bonded directly to one another, or radicals which are bonded to the same carbon atom.

In a preferred embodiment of the invention, Ar is selected, identically or differently on each occurrence, from an aryl or heteroaryl group having 6 aromatic ring atoms or a heteroaryl group having 5 aromatic ring atoms, each of which may be substituted by one or more radicals R. Two substituents R here may also form a further ring system with one another. In a preferred embodiment of the invention, Ar for n=0 is selected from the groups of the following formulae (2) to (5) and for n=1 is selected from the groups of the following formulae (6) to (8), with the proviso that for n=1, at least one group Ar stands for a group of the formula (6),

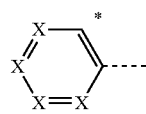
formula (2)

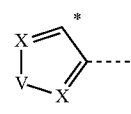
formula (3)

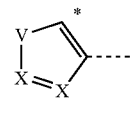
formula (4)

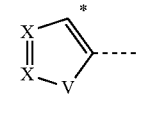
formula (5)

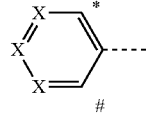
formula (6)

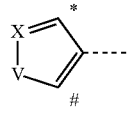
formula (7)

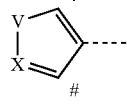
formula (8)

where the dashed bond indicates the link to the second group Ar, # indicates the position of the link to Y, * indicates the link to the nitrogen atom or the carbonyl group of the lactam and furthermore:

X is, identically or differently on each occurrence, CR or N; or two adjacent groups X in formula (2) or formula (6) stand for a group of the following formula (9) or (10),

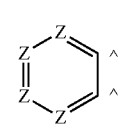
formula (9)

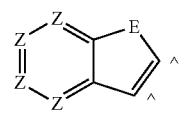
formula (10)

where E stands for NR, $CR_2$, O or S, Z stands, identically or differently on each occurrence, for CR or N and ^ indicate the corresponding adjacent groups X in formula (2) or formula (6);

V is NR, O or S.

Ar is particularly preferably selected, identically or differently on each occurrence, from the group consisting of benzene, pyridine, thiophene, furan, pyrrole, carbazole, fluorene, benzofuran, benzothiophene, dibenzofuran or dibenzothiophene, each of which may be substituted by one or more radicals R. Ar is very particularly preferably on each occurrence benzene, which may be substituted by one or more radicals R, i.e. very particularly preferably stands for a group of the formula (2) or formula (6) in which in each case all groups X stand for CR.

In a further preferred embodiment of the invention, both groups Ar stand for the same aryl or heteroaryl group. The two groups Ar here may be identically or differently substituted.

Preferred embodiments of the compounds of the formula (1) are the compounds of the following formulae (11) to (21),

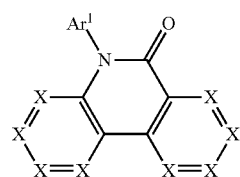
formula (11)

-continued formula (12)
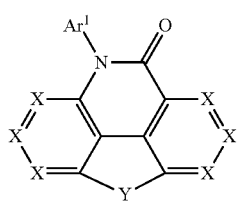

formula (13)
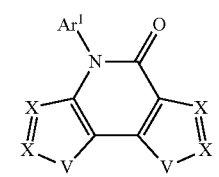

formula (14)
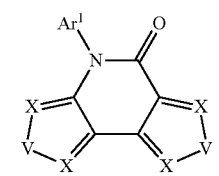

formula (15)
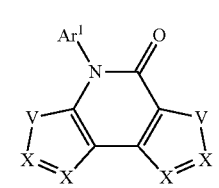

formula (16)
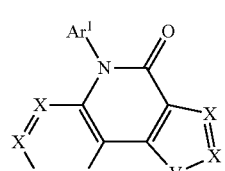

formula (17)
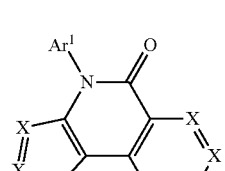

formula (18)
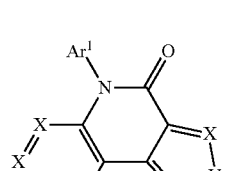

formula (19)
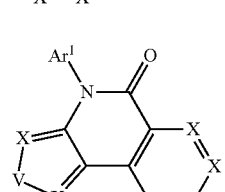

formula (20)
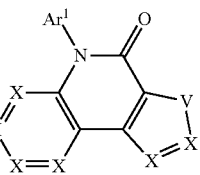

formula (21)
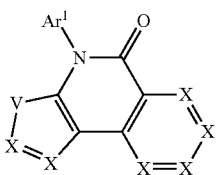

where the symbols used have the meanings given above.

Particular preference is given to the compounds of the above-mentioned formulae (11) and (12).

In a preferred embodiment of the invention, a maximum of one group X per ring stands for N and the other groups X stand, identically or differently on each occurrence, for CR. In a particularly preferred embodiment of the invention, all groups X stand, identically or differently on each occurrence, for CR.

Particular preference is therefore given to the compounds of the following formulae (11a) and (12a), formula (11a)
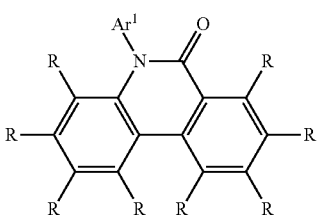

formula (12a)
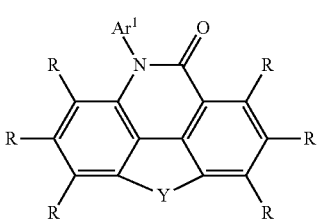

where the symbols used have the meanings given above.

Very particular preference is given to the compounds of the following formulae (11b), (11c), (11d), (12b), (12c) and (12d), formula (11b)
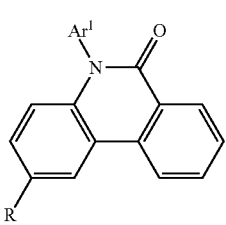

formula (11c)

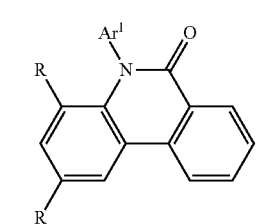

formula (11d)

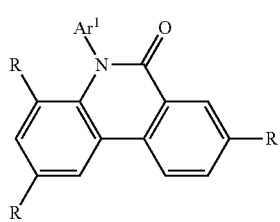

formula (12b)

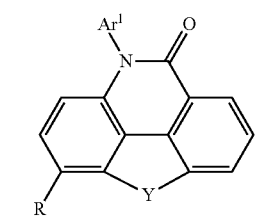

formula (12c)

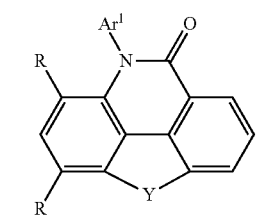

formula (12d)

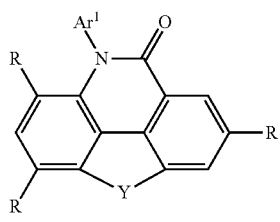

where the symbols used have the meanings given above.

As already described above, Ar¹ represents an aromatic or heteroaromatic ring system having 5 to 24 aromatic ring atoms, which may be substituted by one or more radicals R and which contains no aryl or heteroaryl groups having more than two aromatic six-membered rings condensed directly onto one another. Ar¹ and also the radicals R which are bonded to Ar¹ preferably contains absolutely no aromatic six-membered rings condensed directly onto one another.

Particularly preferred groups Ar¹ are selected from the group consisting of benzene, ortho-, meta- or para-biphenyl, ortho-, meta-, para- or branched terphenyl, linear or branched quaterphenyl, fluorene, in particular 2-fluorene, spirobifluorene, in particular 2-spirobifluorene, carbazole, in particular 2- or 3-carbazole, dibenzothiophene, in particular 1-, 2- or 3-dibenzothiophene, dibenzofuran, in particular 1-, 2- or 3-dibenzofuran, 1,3,5-triazine, pyridine, pyrimidine, indenocarbazole, bridged carbazole or indolocarbazole or combinations of two or three of these groups. These groups may each also be substituted by one or more radicals R.

In a preferred embodiment of the invention, the index n=0.

In a further preferred embodiment of the invention, the index n=1 and Y is selected from the group consisting of —C(=O)—N(Ar¹)—, —C(=O)—O—, C(=O), C(R¹)$_2$ or NR¹, particularly preferably —C(=O)—N(Ar¹)— or C(R¹)$_2$. This preference also applies to the above-mentioned compounds of the formula (12) or (12a) to (12d). The group Y may be bonded in both possible orientations here. This is illustrated diagrammatically below on a compound where Y=—C(=O)—N(Ar¹)—:

structure (A)

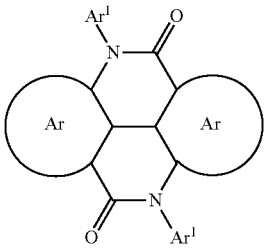

structure (B)

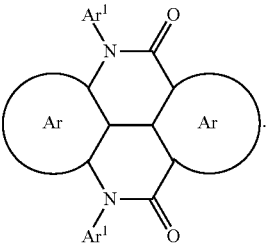

The orientation shown in structure (A), in which in each case a carbonyl group and a group NAr¹ is bonded to each group Ar, is the preferred orientation here.

If the group Y stands for a group —C(=O)—N(Ar¹)—, the group Ar¹ is then preferably selected from the groups Ar¹ mentioned as preferred above. In this case, the two groups Ar¹ in the molecule are particularly preferably selected identically.

In a preferred embodiment of the invention, R in the above-mentioned formulae is selected, identically or differently on each occurrence, from the group consisting of H, D, F, CN, N(Ar²)$_2$, C(=O)Ar², a straight-chain alkyl or alkoxy group having 1 to 10 C atoms or a branched or cyclic alkyl or alkoxy group having 3 to 10 C atoms or an alkenyl group having 2 to 10 C atoms, each of which may be substituted by one or more radicals R², where one or more non-adjacent CH$_2$ groups may be replaced by O and where one or more H atoms may be replaced by D or F, an aromatic or heteroaromatic ring system having 5 to 30 aromatic ring atoms, which may in each case be substituted by one or more radicals R², or an aryloxy or heteroaryloxy group having 5 to 30 aromatic ring atoms, which may be substituted by one or more radicals R².

In a particularly preferred embodiment of the invention, R in the above-mentioned formulae is selected, identically or differently on each occurrence, from the group consisting of H, a straight-chain alkyl group having 1 to 10 C atoms or a branched or cyclic alkyl group having 3 to 10 C atoms, each of which may be substituted by one or more radicals R², or an aromatic or heteroaromatic ring system having 5 to 18 aromatic ring atoms, which may in each case be substituted by one or more radicals R².

R especially preferably stands for an aromatic or heteroaromatic ring system having 5 to 18 aromatic ring atoms, which may in each case be substituted by one or more radicals R[2]. If R stands for an aromatic or heteroaromatic ring system, this preferably contains no aryl or heteroaryl groups in which more than two aromatic six-membered rings are condensed directly onto one another and particularly preferably contains absolutely no aryl or heteroaryl groups in which aromatic six-membered rings are condensed directly onto one another.

If R as substituent on the groups Ar stands for an aromatic or heteroaromatic ring system, this is particularly preferably selected from the group consisting of benzene, ortho-, meta- or para-biphenyl, ortho-, meta-, para- or branched terphenyl, linear or branched quaterphenyl, fluorene, in particular 2-fluorene, spirobifluorene, in particular 2-spirobifluorene, carbazole, in particular 2- or 3-carbazole or N-carbazole, dibenzothiophene, in particular 1-, 2- or 3-dibenzothiophene, dibenzofuran, in particular 1-, 2- or 3-dibenzofuran, 1,3,5-triazine, pyridine, pyrimidine or combinations of two or three of these groups. These groups may each also be substituted by one or more radicals R[2].

For compounds which are processed by vacuum evaporation, the alkyl groups preferably have not more than five C atoms, particularly preferably not more than 4 C atoms, very particularly preferably not more than 1 C atom. For compounds which are processed from solution, suitable compounds are also those which are substituted by alkyl groups having up to 10 C atoms or which are substituted by oligoarylene groups, for example ortho-, meta-, para- or branched terphenyl or quaterphenyl groups.

In a particularly preferred embodiment of the invention, the above-mentioned preferences occur simultaneously.

Examples of preferred compounds of the above-mentioned embodiments are the compounds of the following structures (1) to (201).

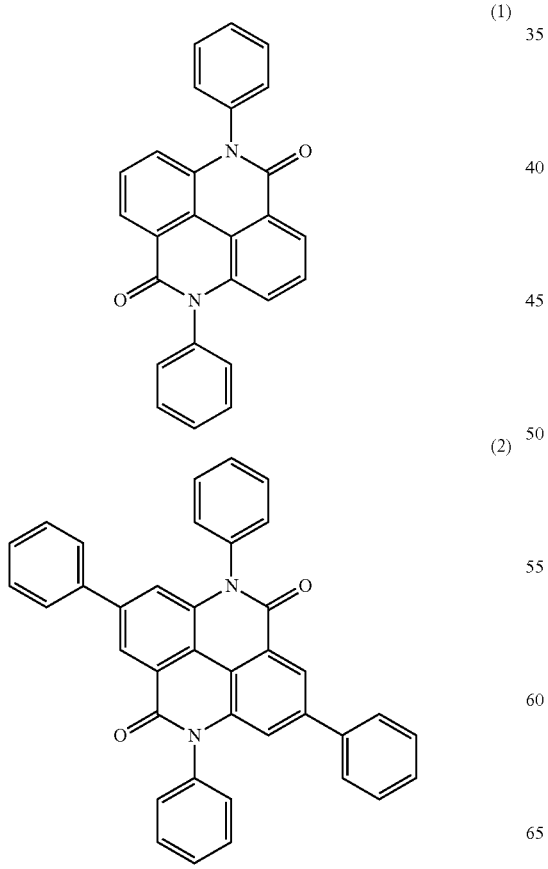

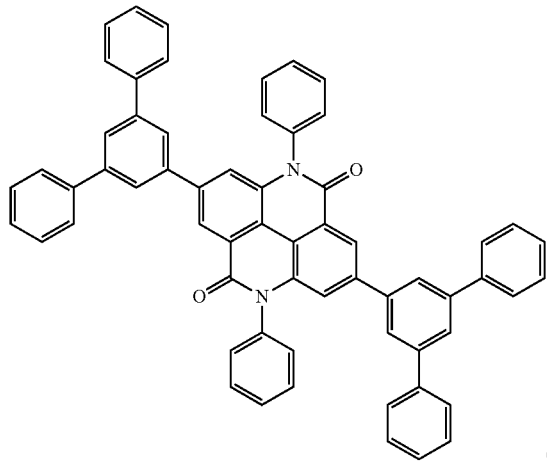

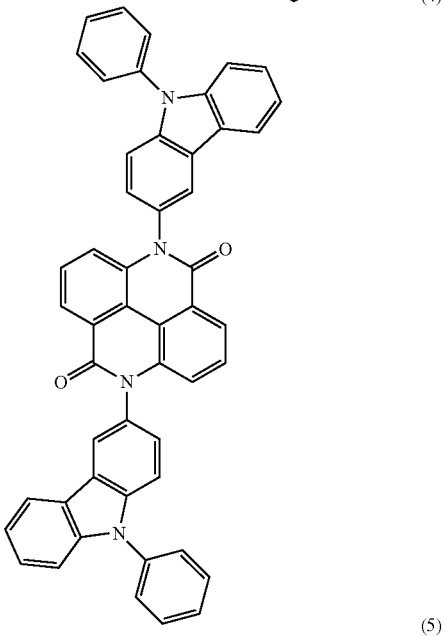

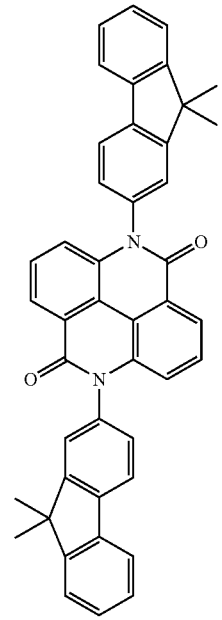

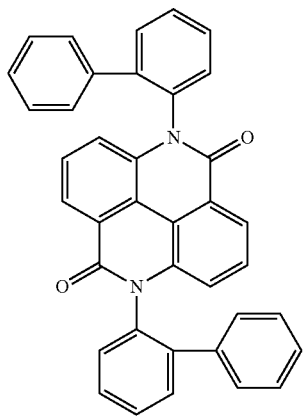
(6)
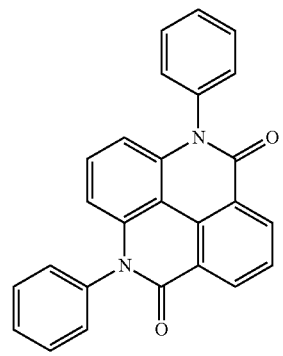
(7)
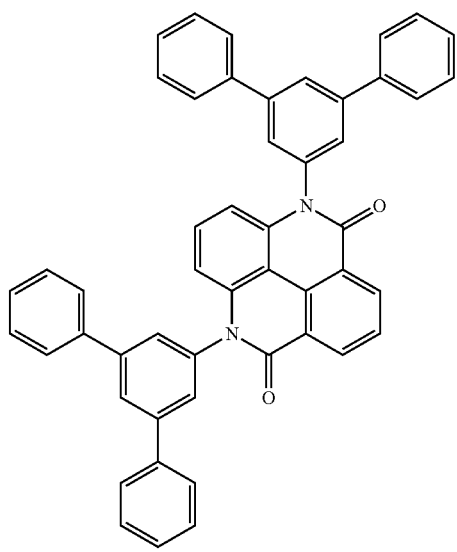
(8)
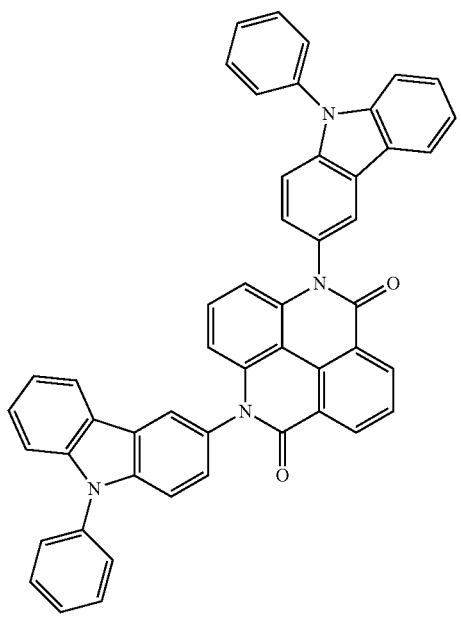
(9)
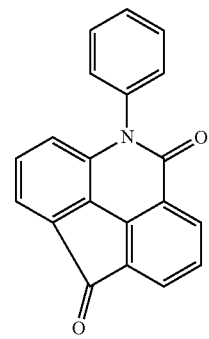
(10)
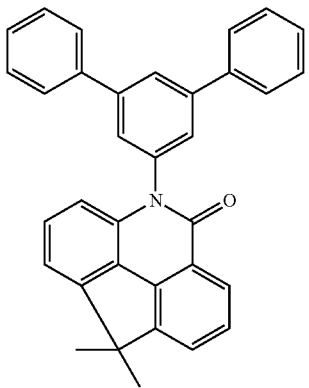
(11)

-continued
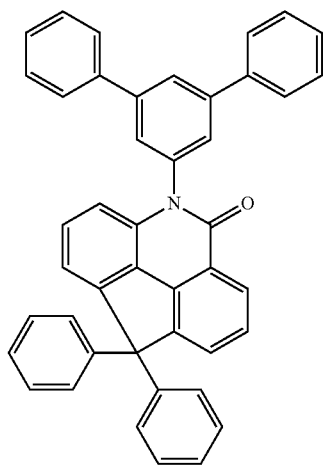
(12)
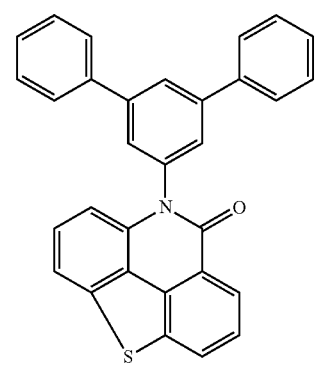
(13)
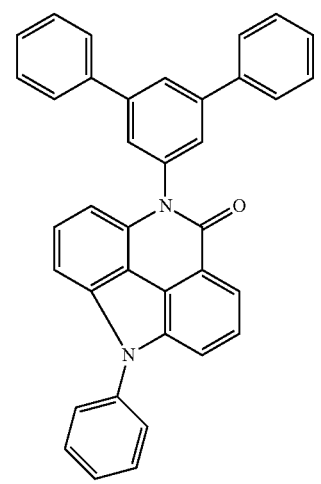
(14)
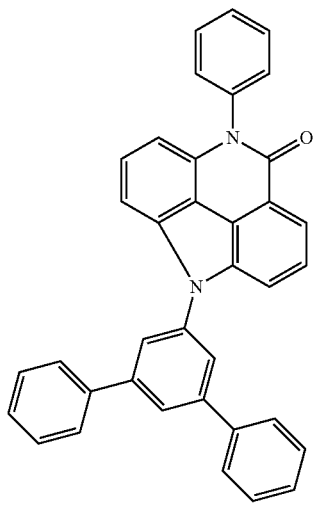
(15)
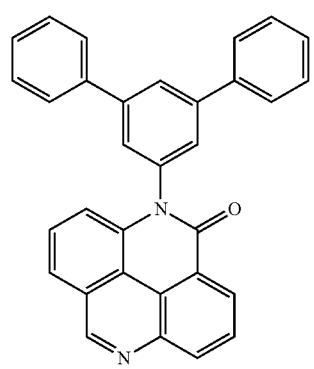
(16)
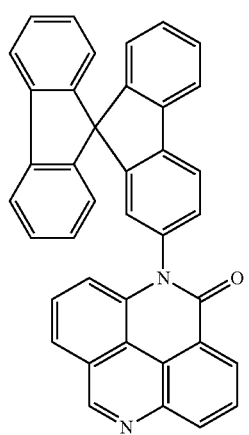
(17)

(18)
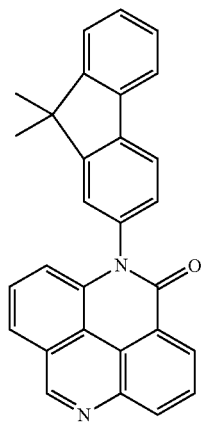
(19)
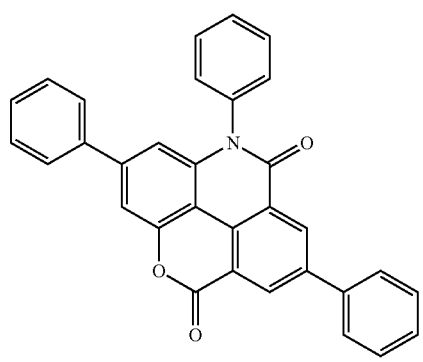
(20)
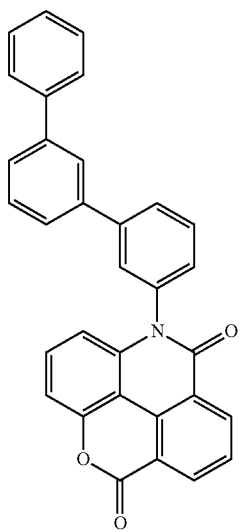
(21)
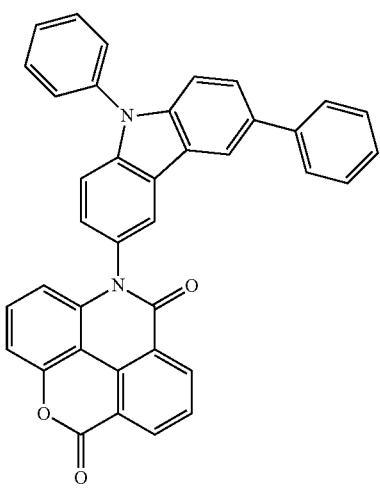
(22)
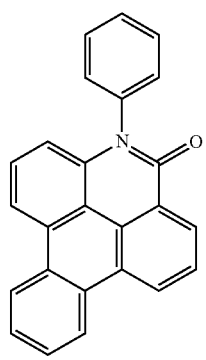
(23)
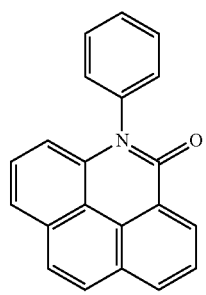
(24)
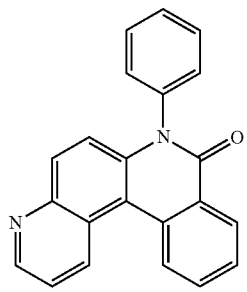

(25)
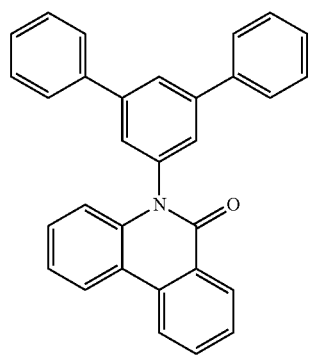
(26)
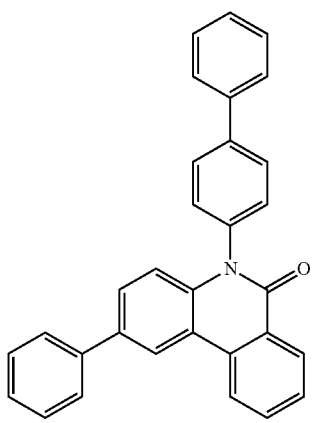
(27)
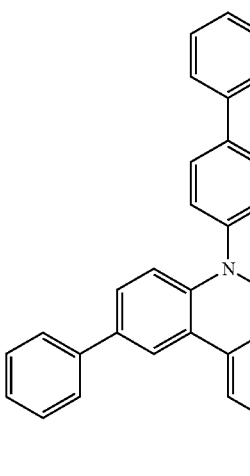
(28)
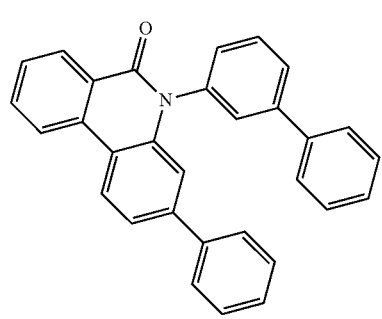
(29)
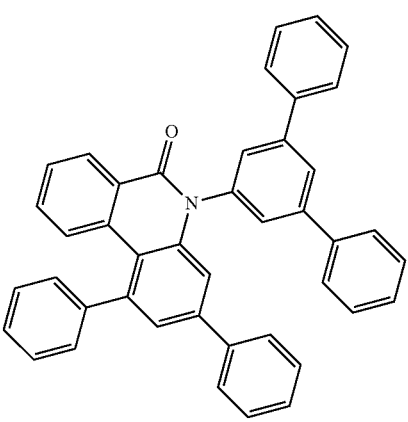
(30)
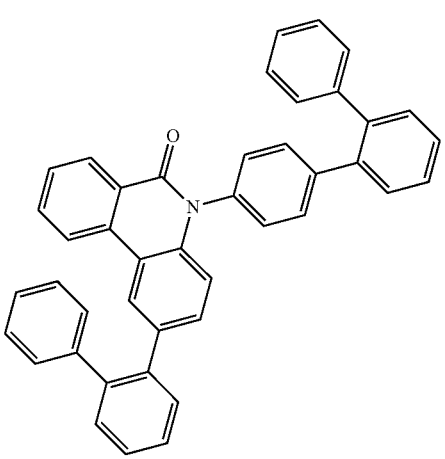
(31)
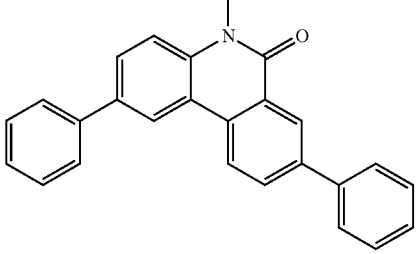

(32)
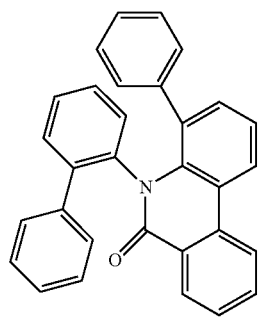
(33)
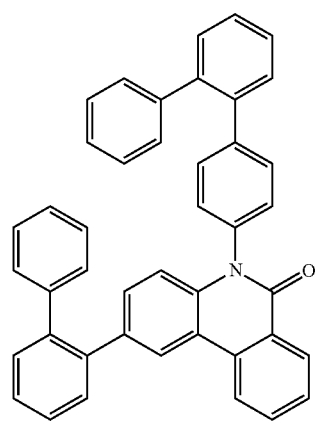
(34)
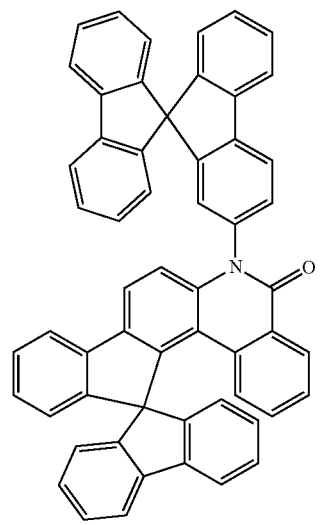
(35)
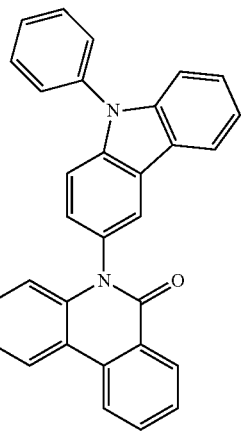
(36)
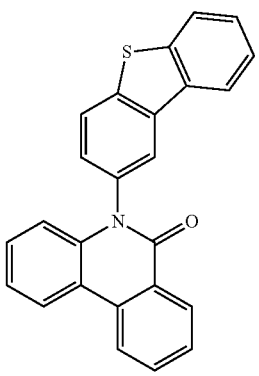
(37)
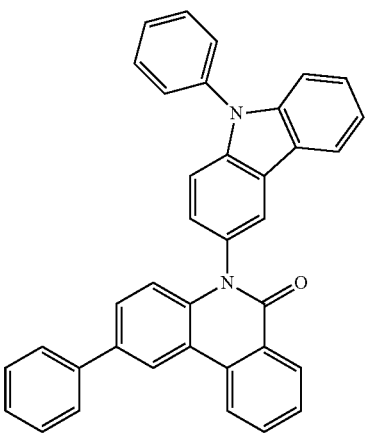

(38)
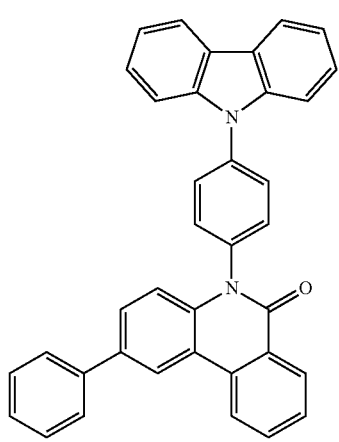
(39)
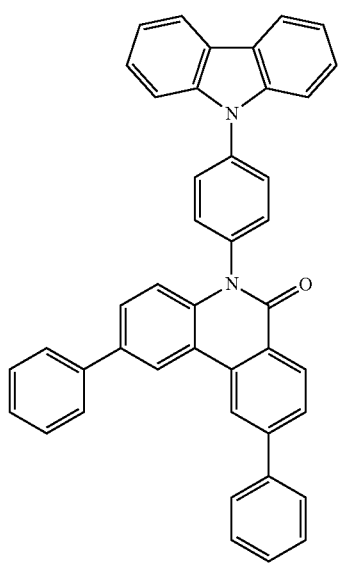
(40)
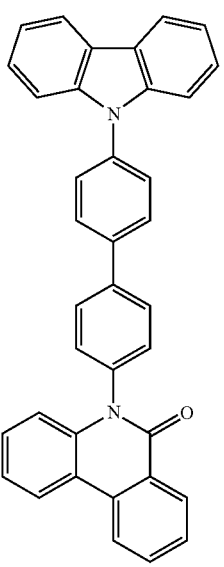
(41)
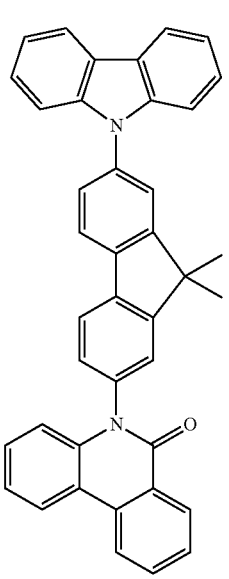
(42)
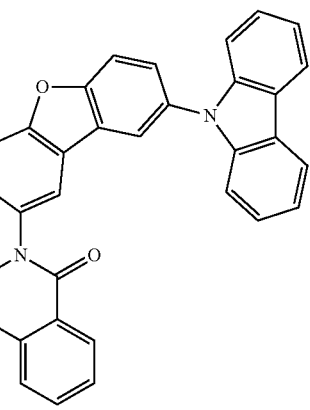
(43)
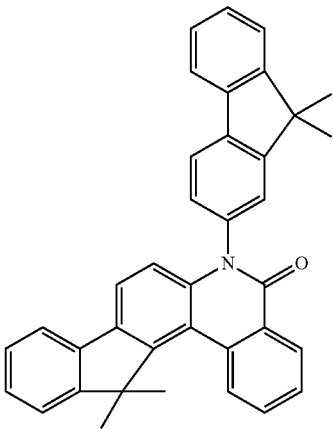

(44)
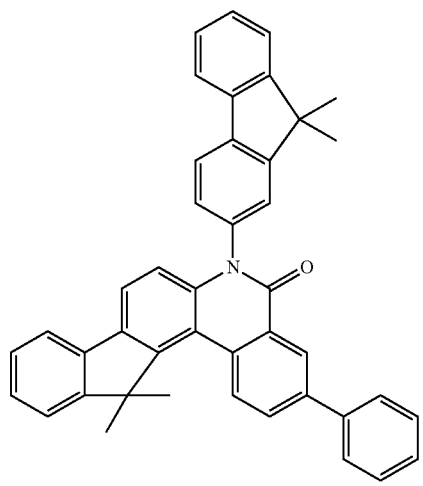
(45)
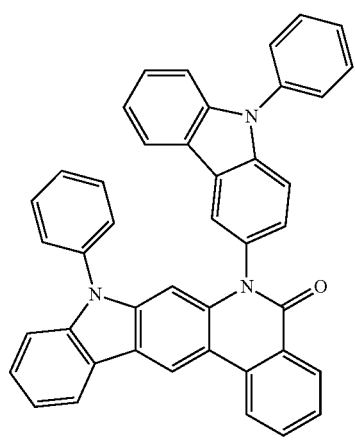
(46)
(47)
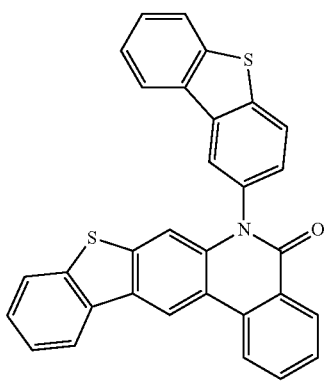
(48)
(49)
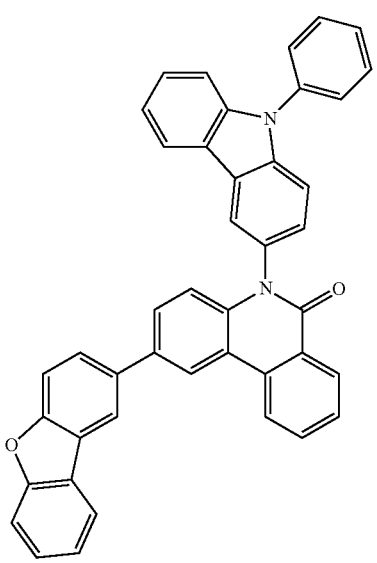

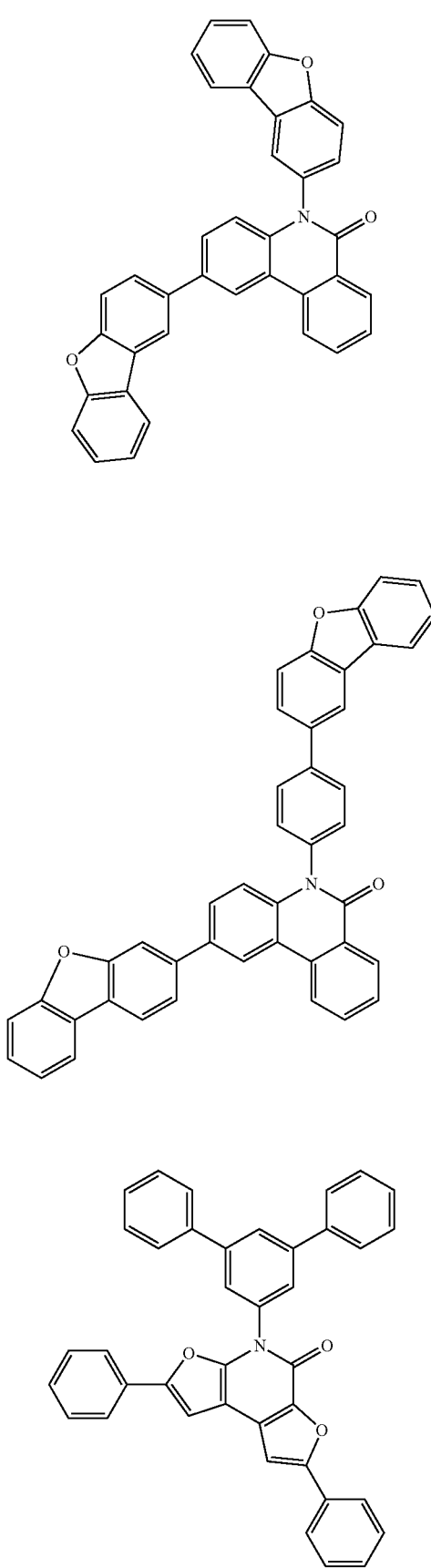
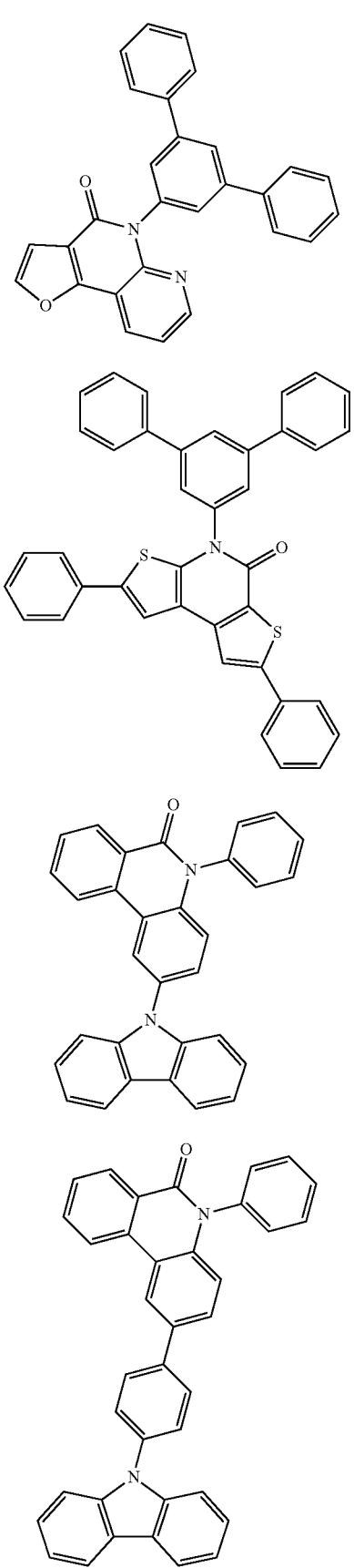

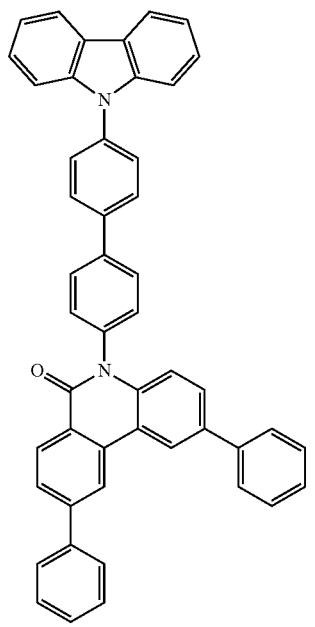
(57)
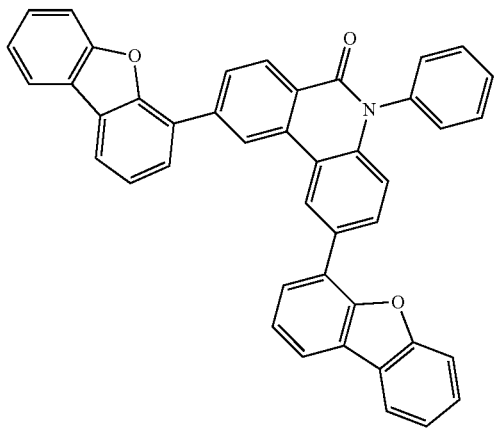
(58)
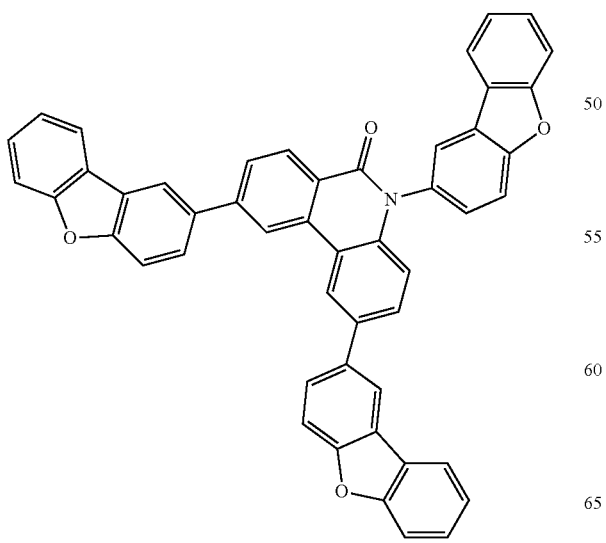
(59)
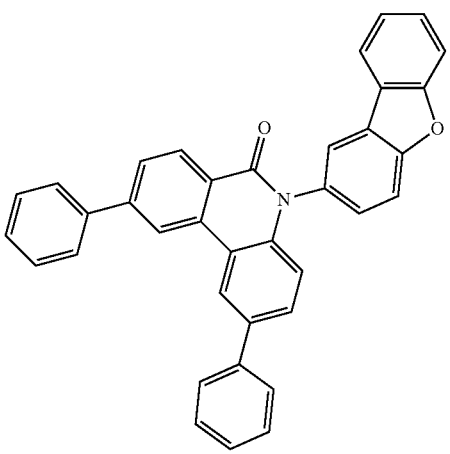
(60)
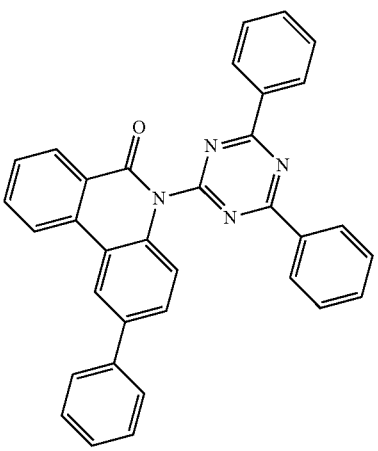
(61)
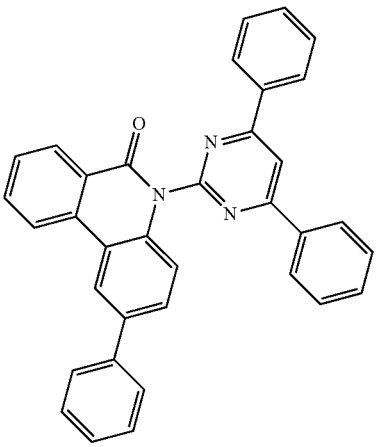
(62)

(63)
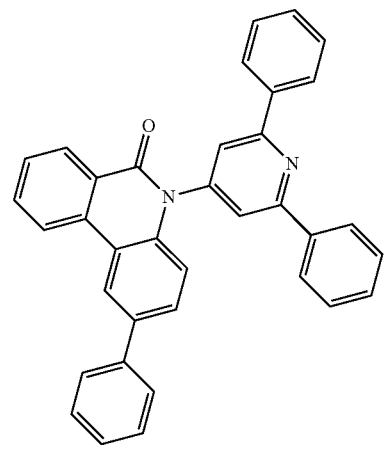
(64)
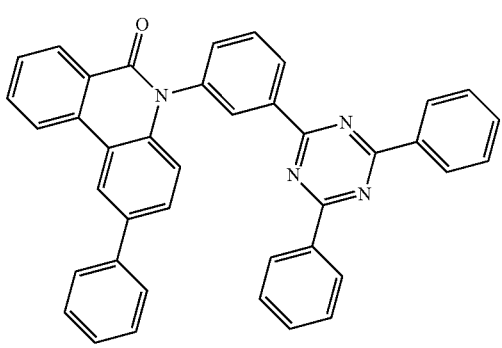
(65)
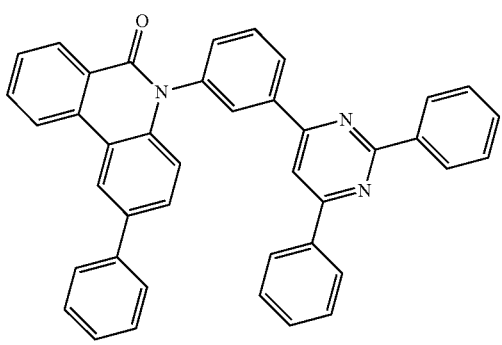
(66)
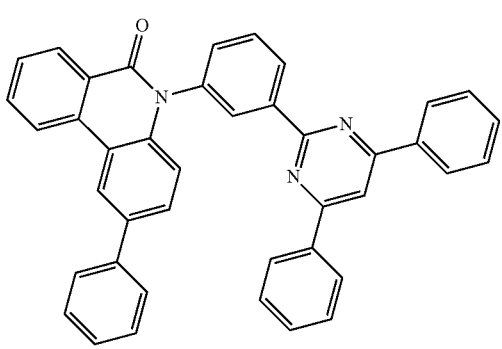
(67)
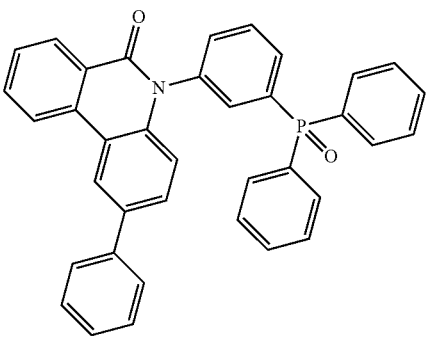
(68)
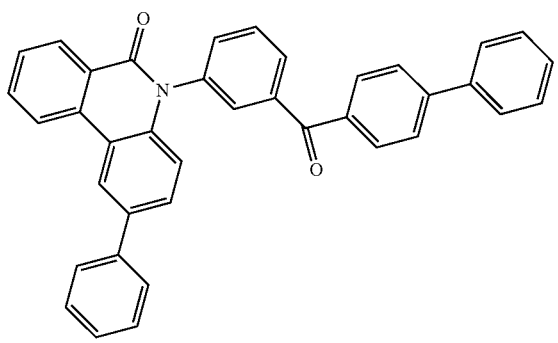
(69)
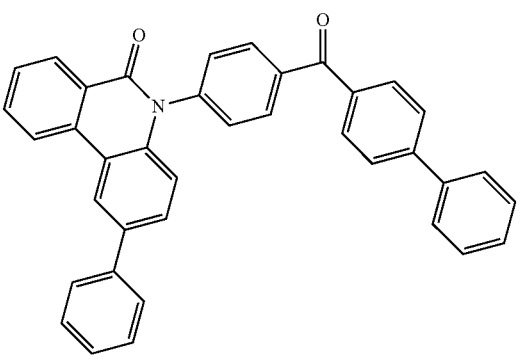
(70)
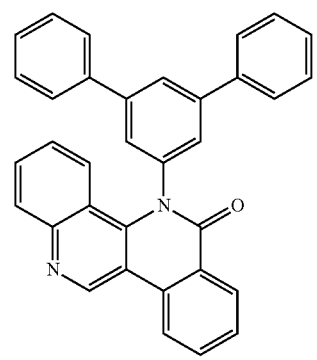

-continued
(71)
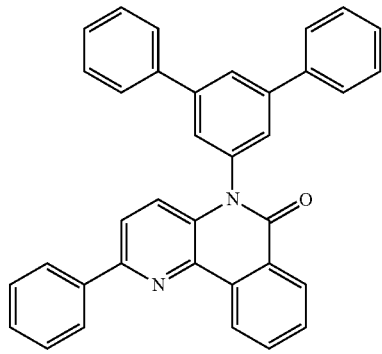
(72)
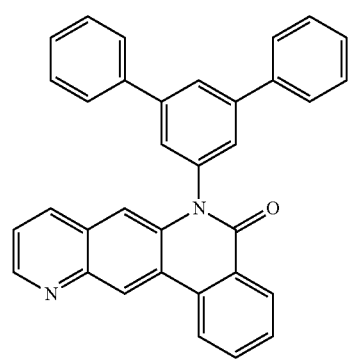
(73)
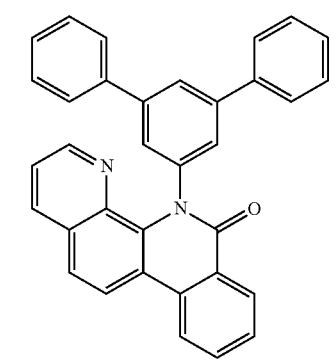
(74)
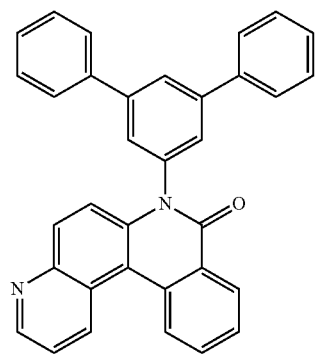
-continued
(75)
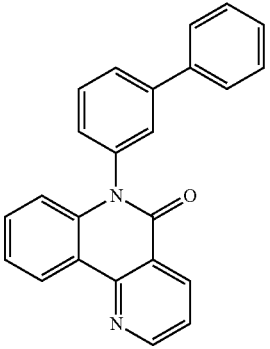
(76)
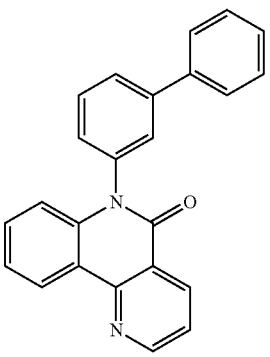
(77)
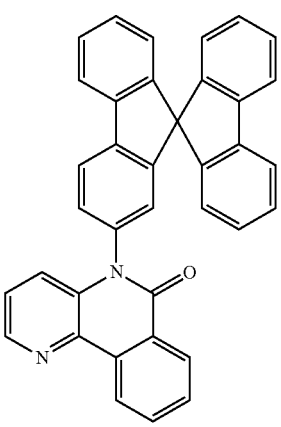
(78)
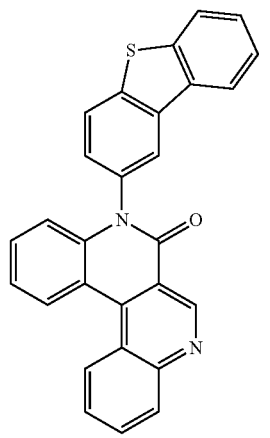

(79)
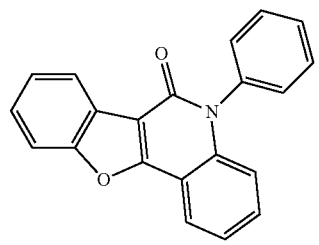
(80)
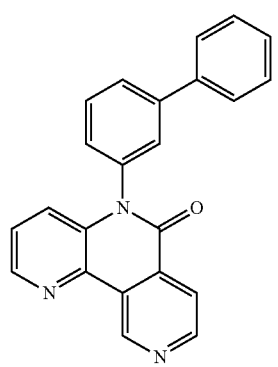
(81)
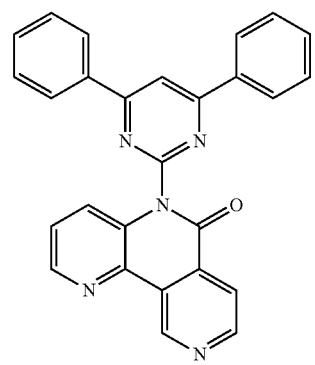
(82)
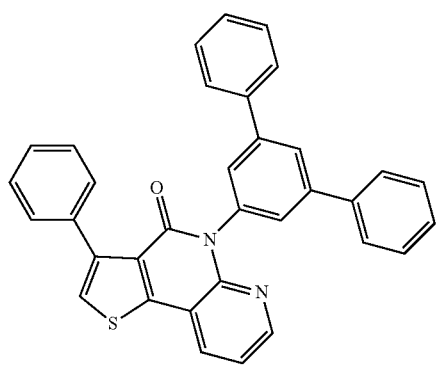
(83)
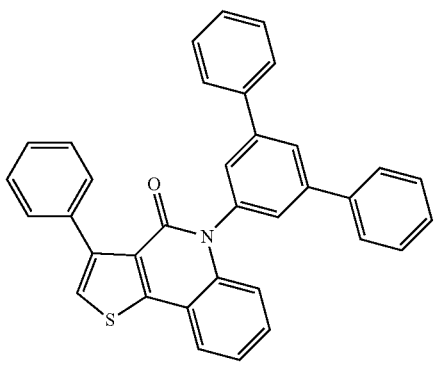
(84)
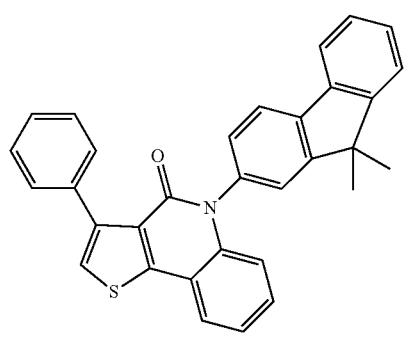
(85)
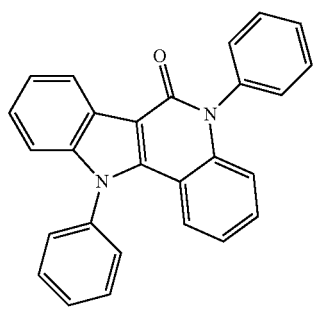
(86)
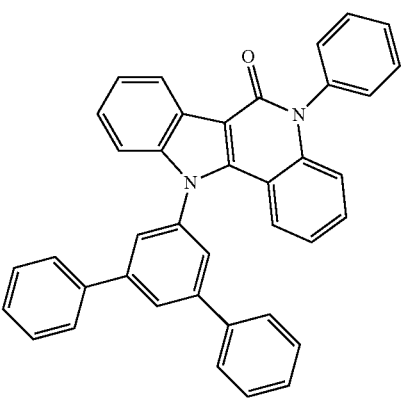

(87)
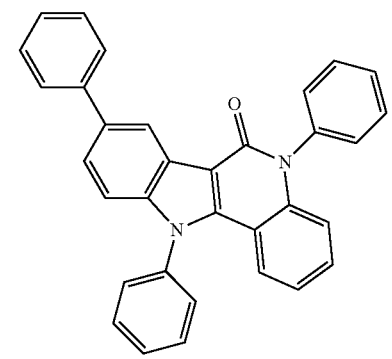
(88)
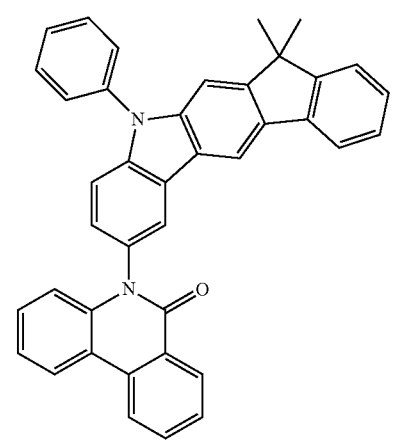
(89)
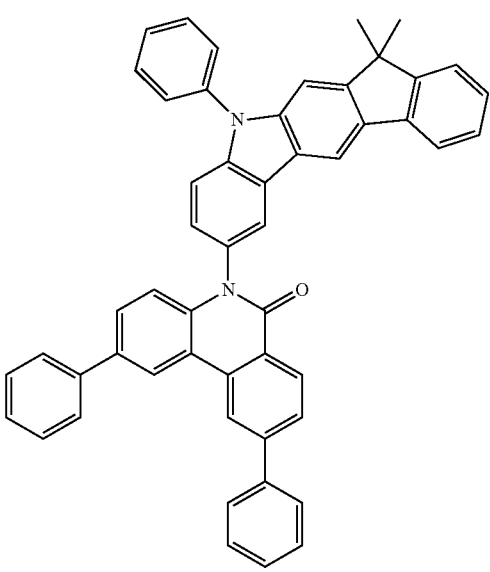
(90)
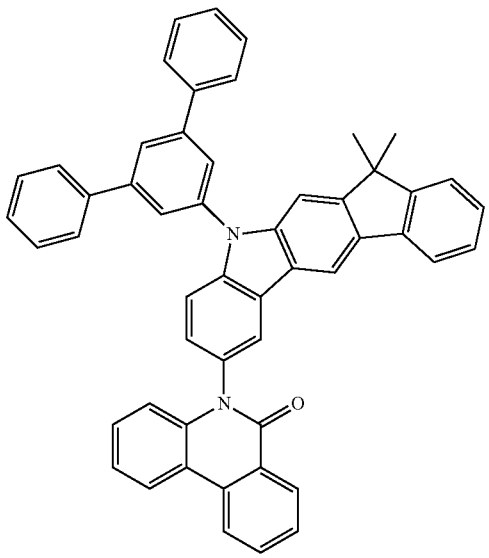
(91)
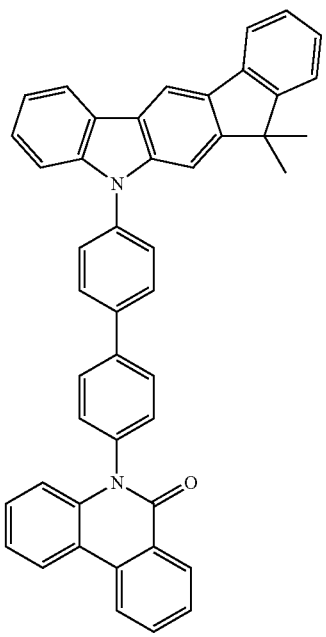
(92)
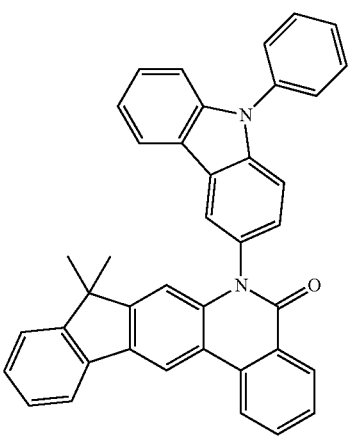

(93)
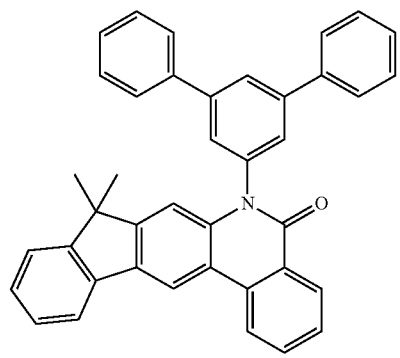
(94)
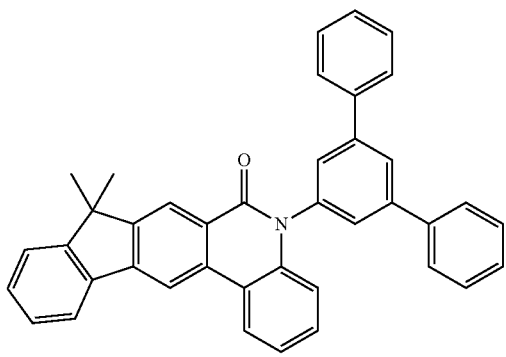
(95)
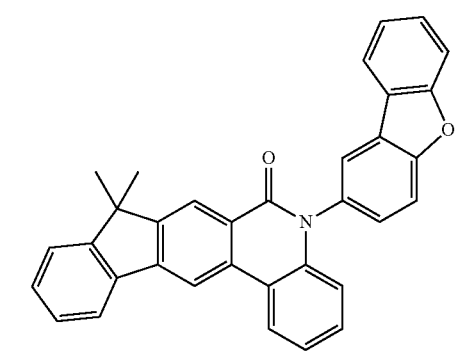
(96)
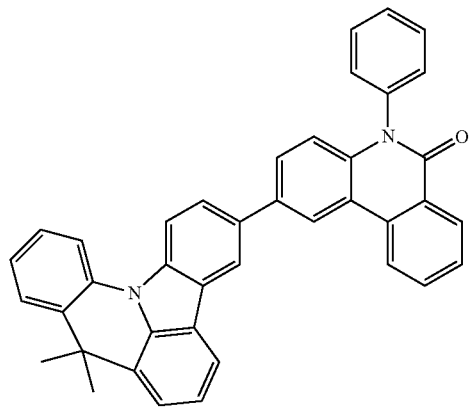
(97)
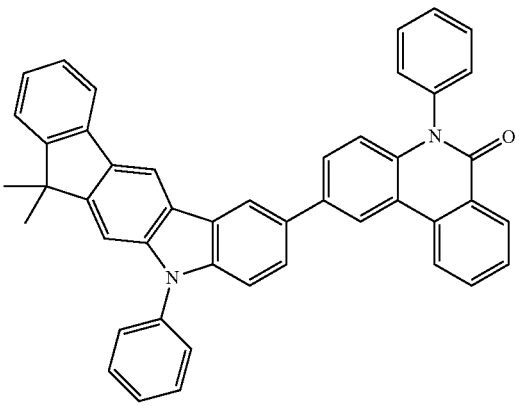
(98)
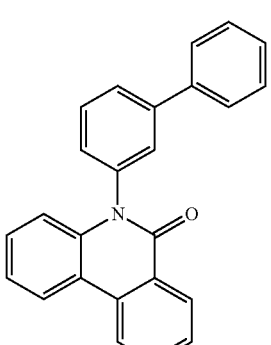
(99)
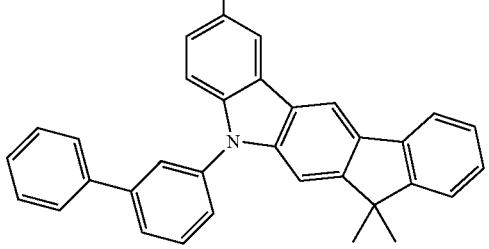
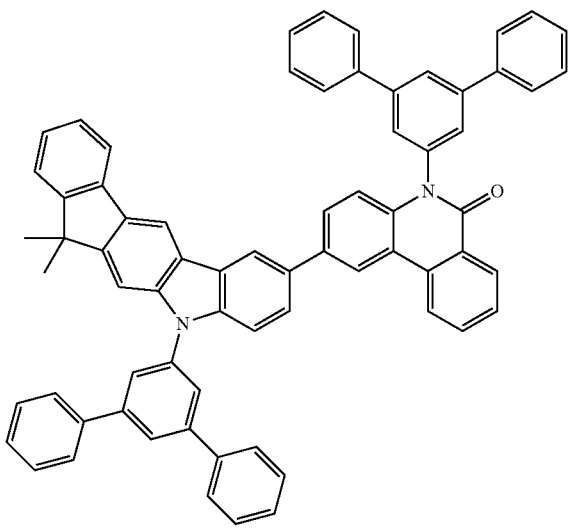

(100)
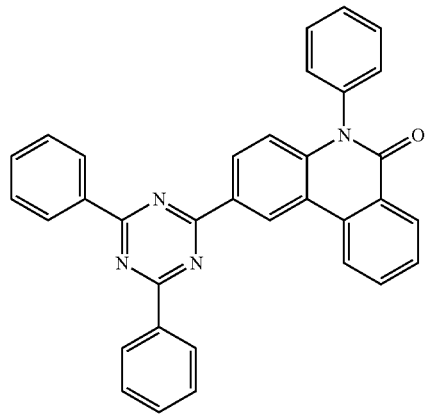
(101)
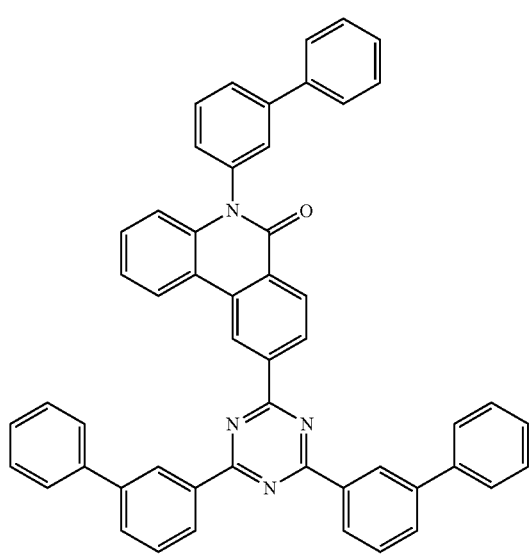
(102)
(103)
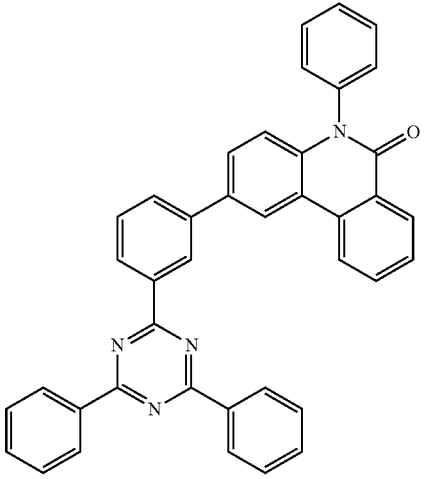
(104)
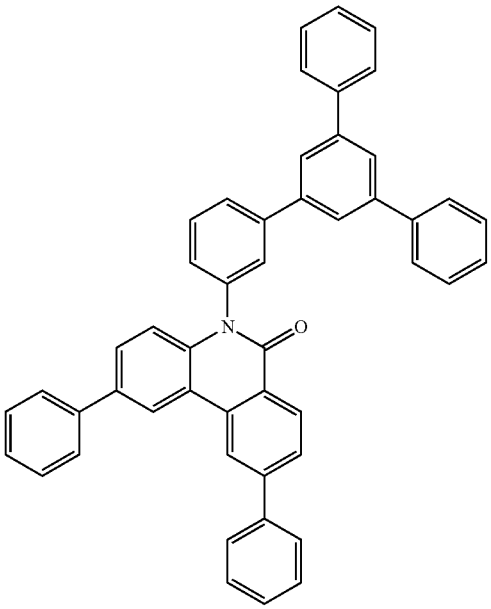
(105)
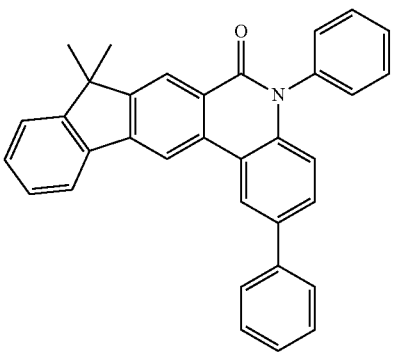

(106)
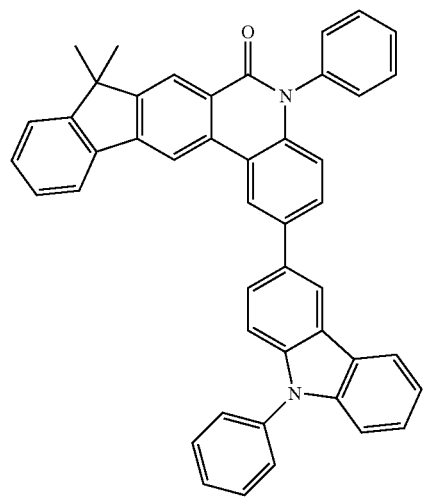
(109)
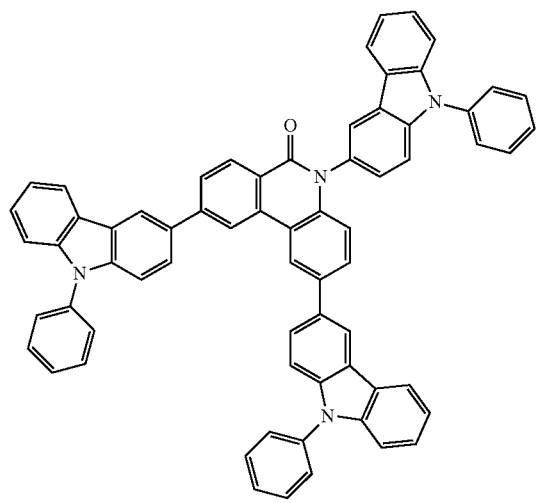
(107)
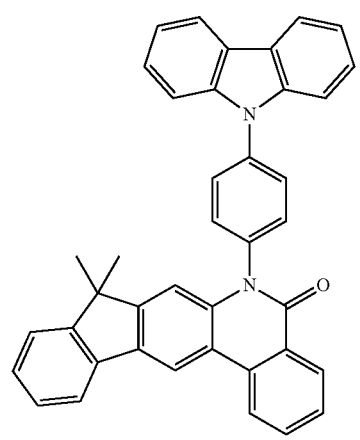
(110)
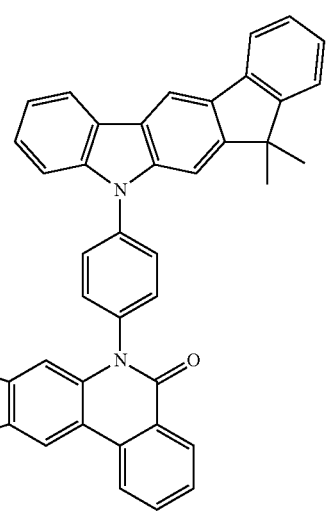
(108)
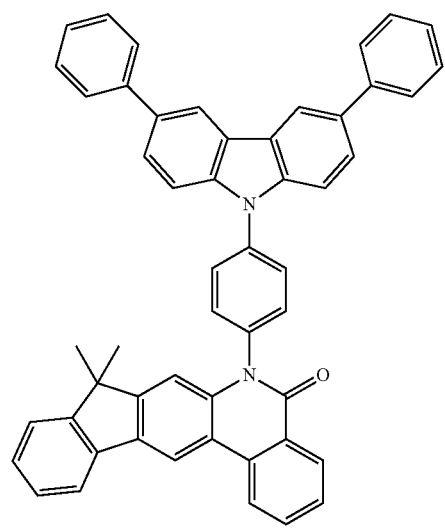
(111)
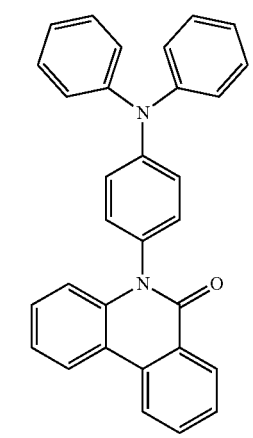

(112)
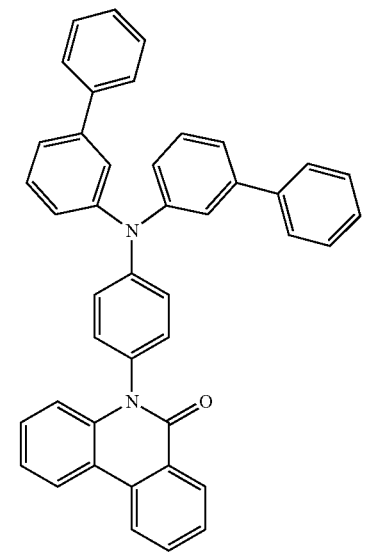
(113)
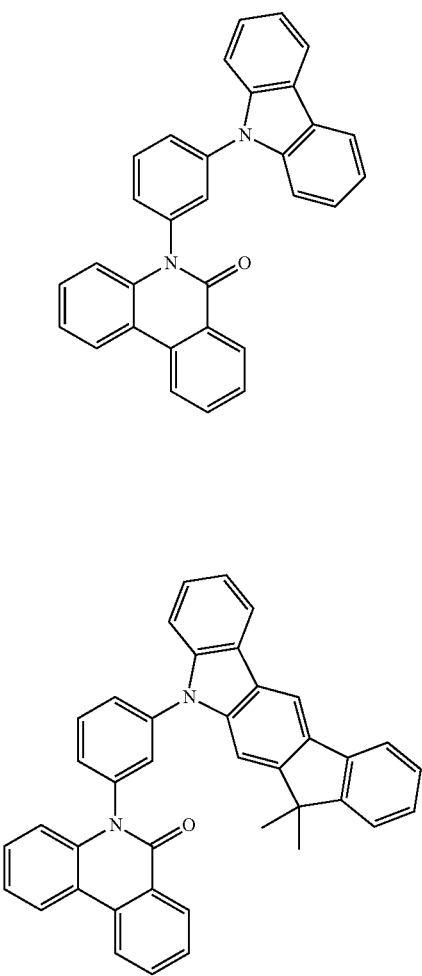
(114)
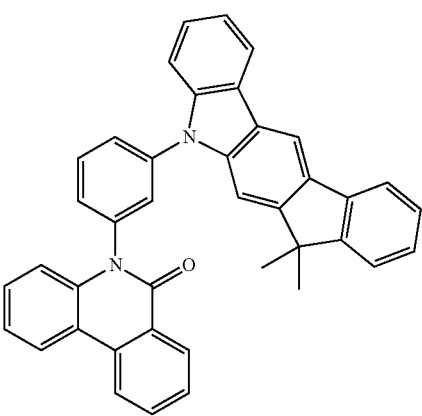
(115)
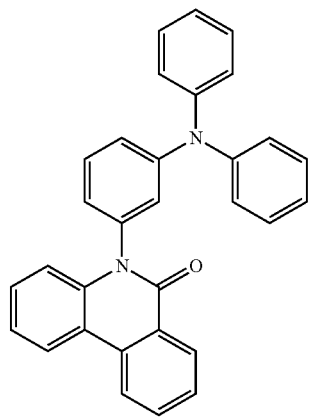
(116)
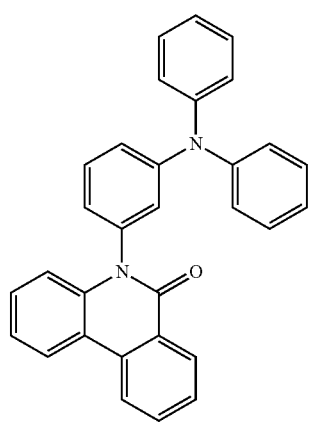
(117)
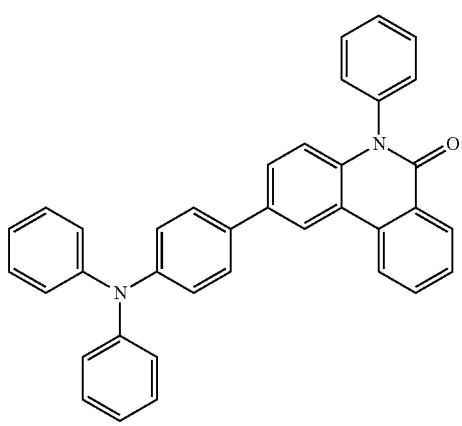
(118)
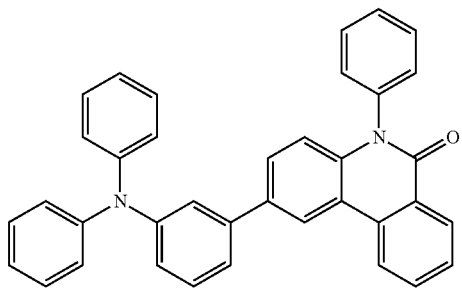

(119)
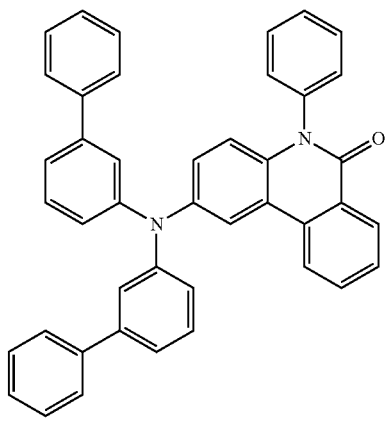
(120)
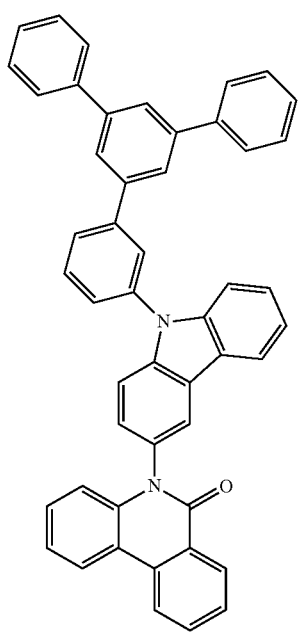
(121)
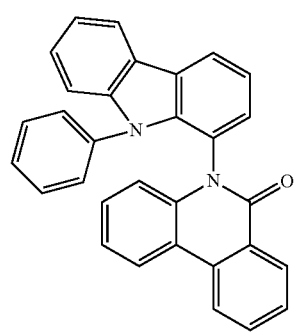
(122)
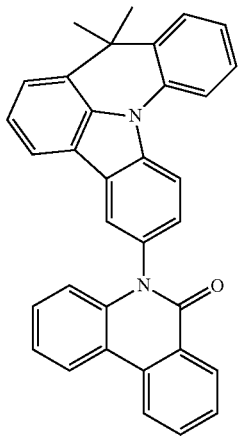
(123)
(124)
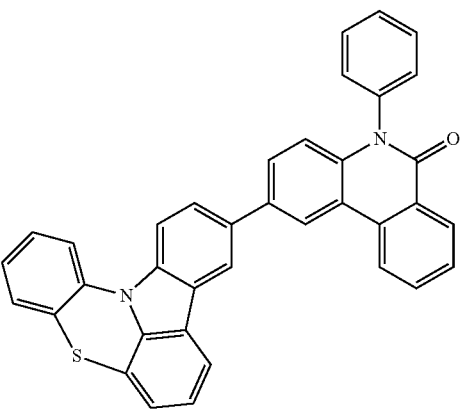

(125) 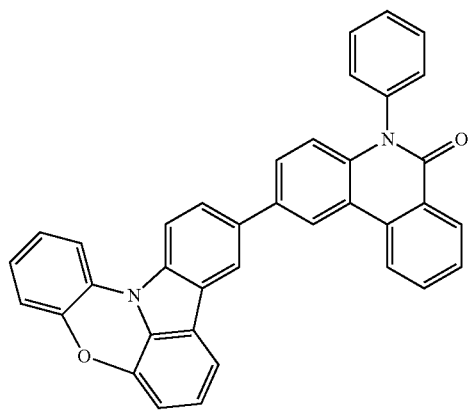
(126) 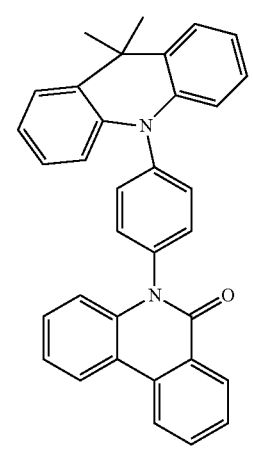
(127) 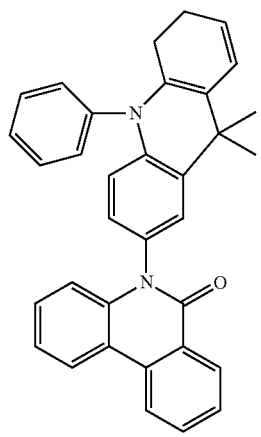
(128) 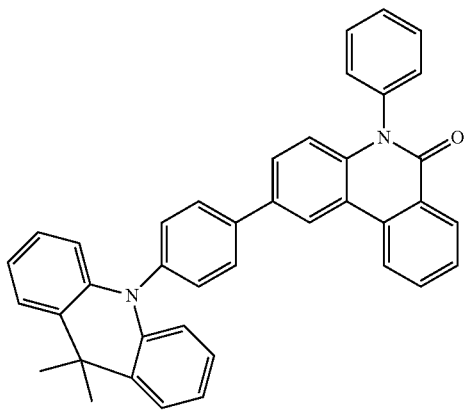
(129) 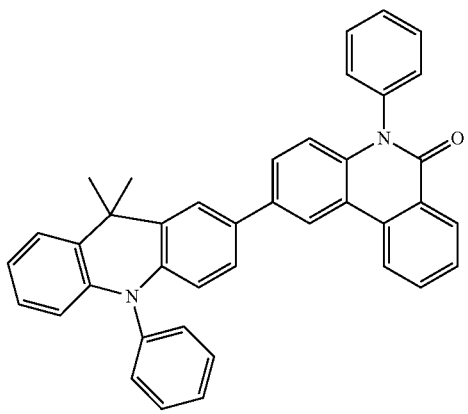
(130) 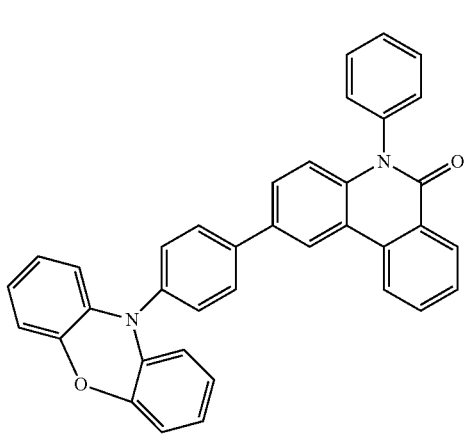
(131) 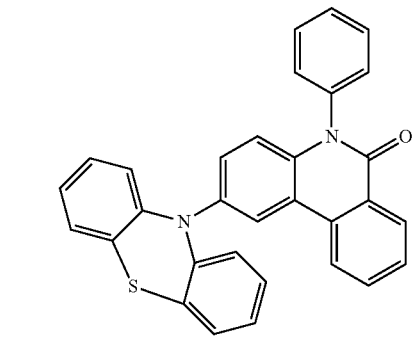

-continued
(132)
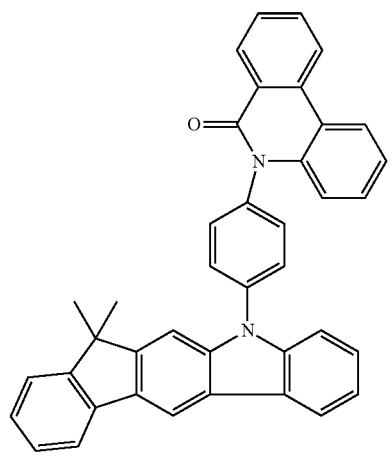
(133)
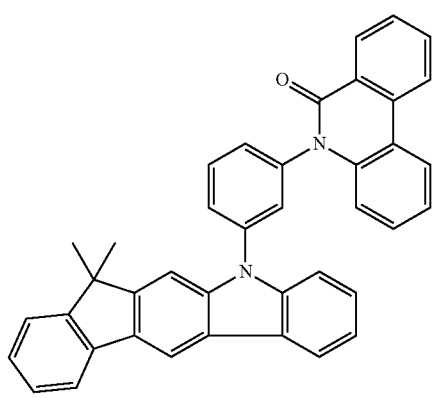
(134)
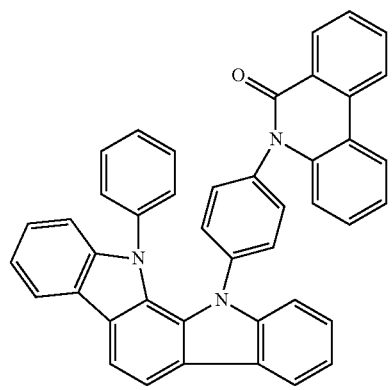
-continued
(135)
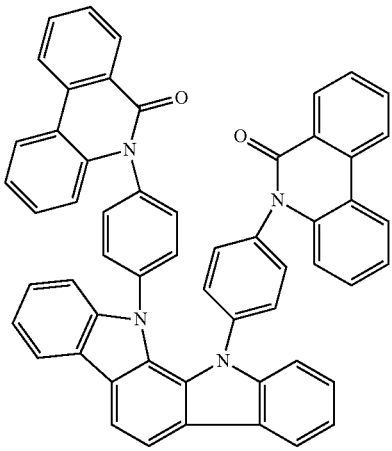
(136)
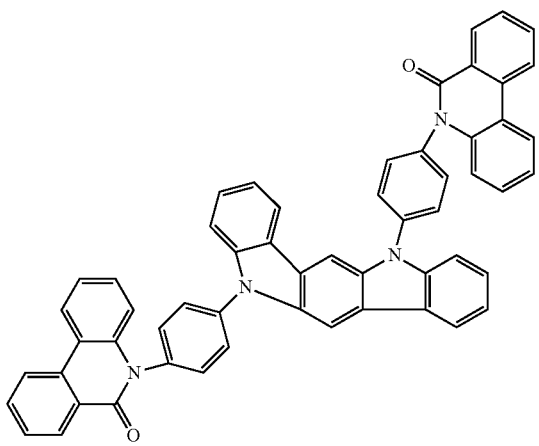
(137)
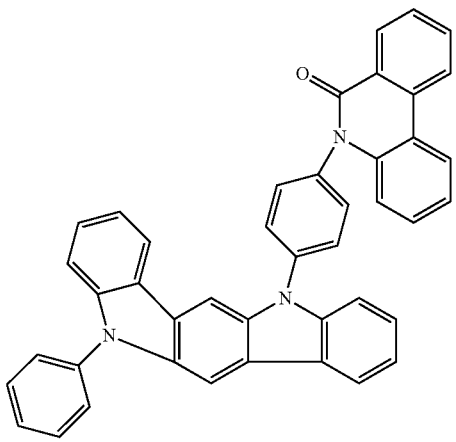

(138)
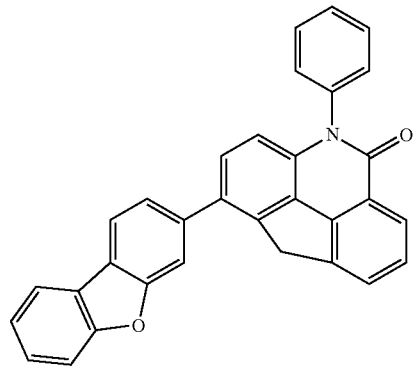
(139)
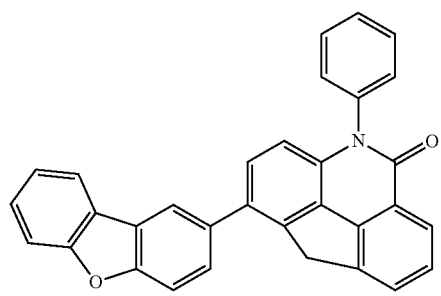
(140)
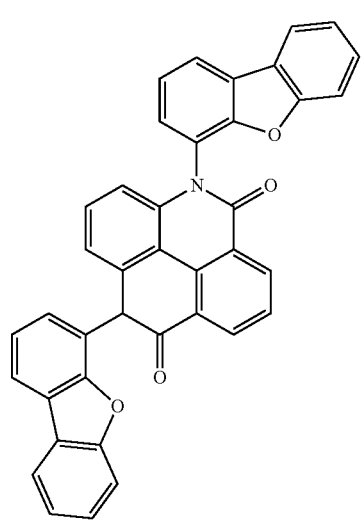
(141)
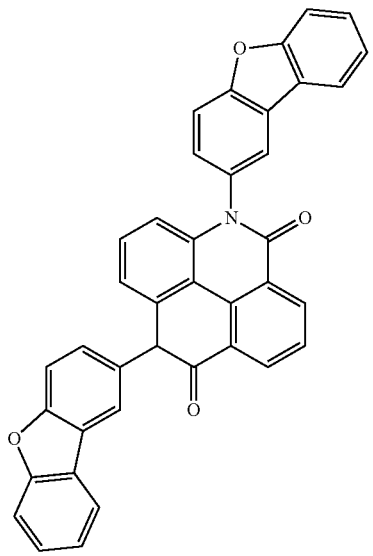
(142)
(143)
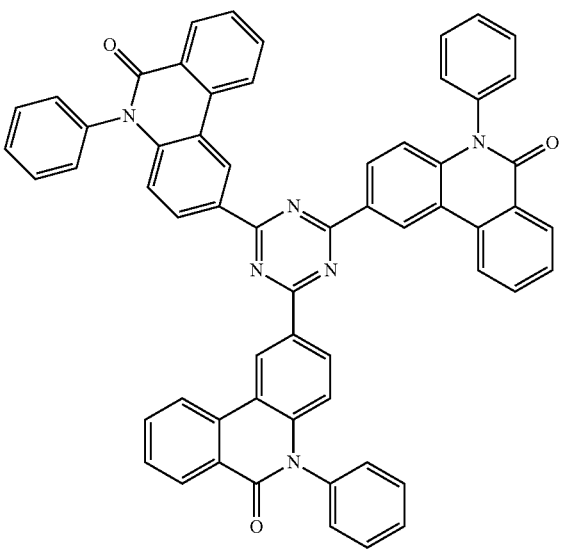

(144)
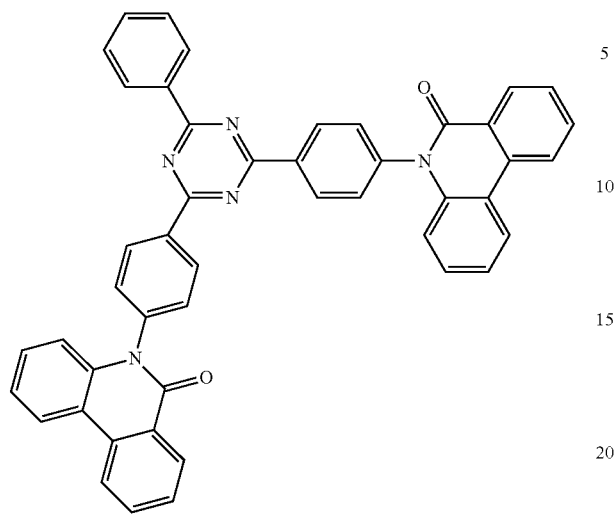
(145)
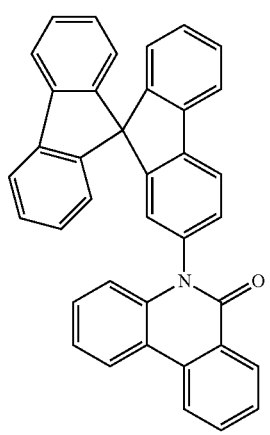
(146)
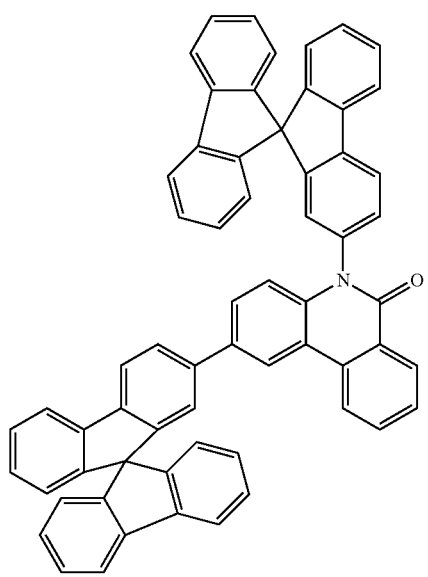
(147)
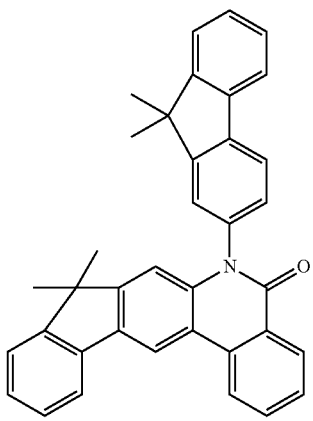
(148)
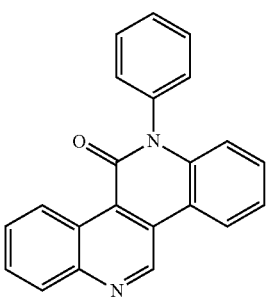
(149)
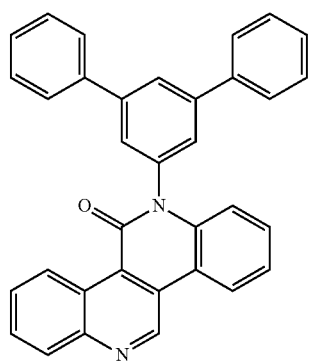
(150)
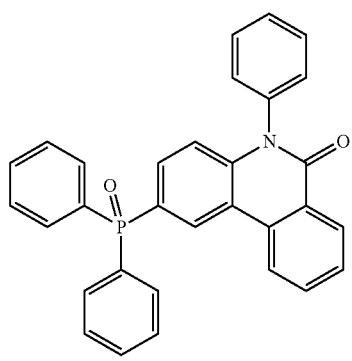

-continued
(151)
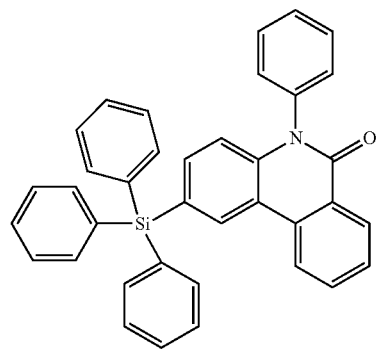
(152)
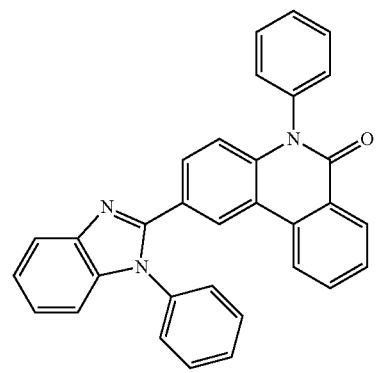
(153)
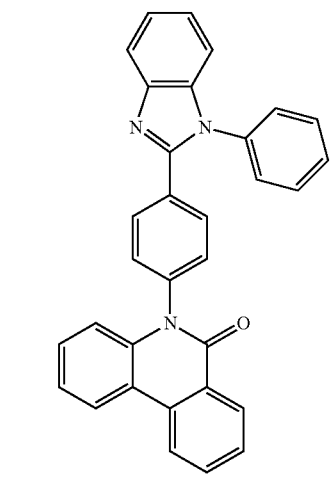
(154)
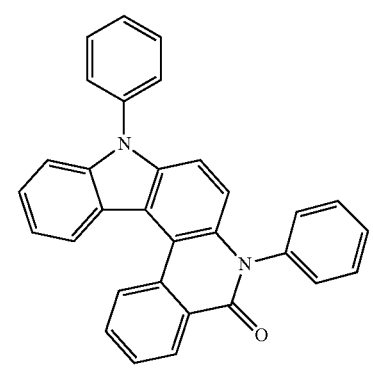
-continued
(155)
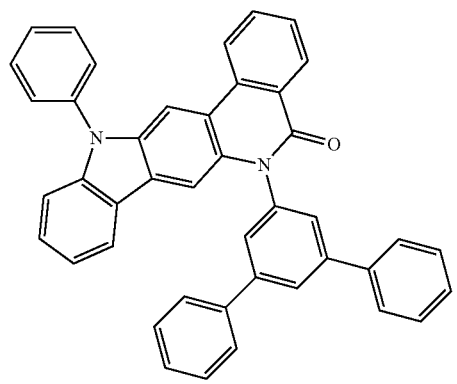
(156)
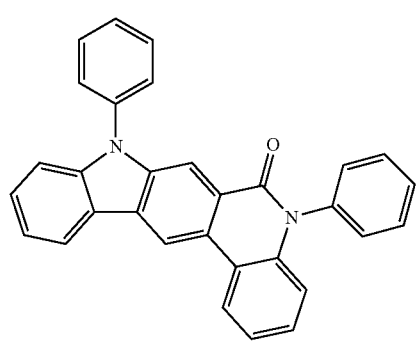
(157)
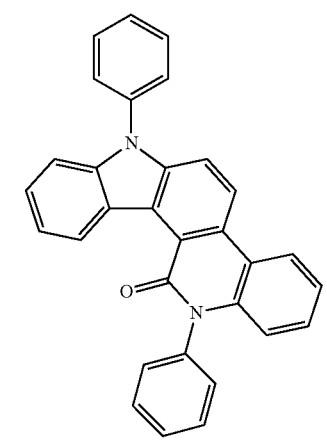
(158)
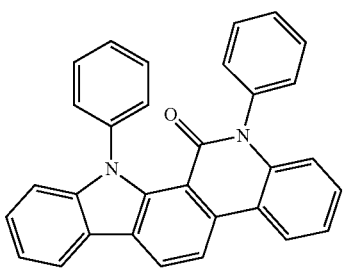

(159)
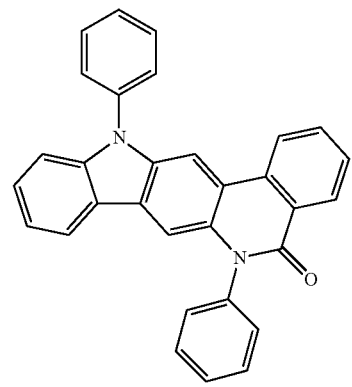
(160)
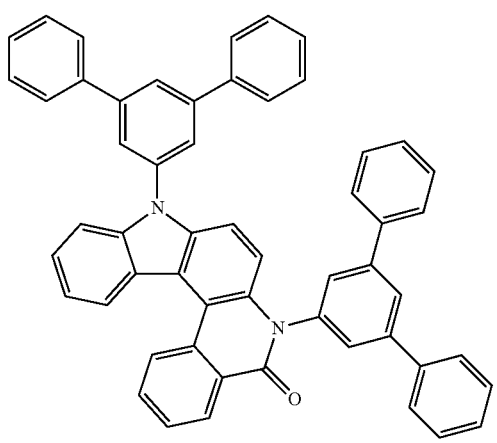
(161)
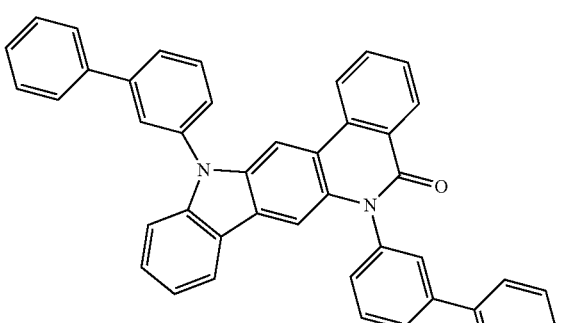
(162)
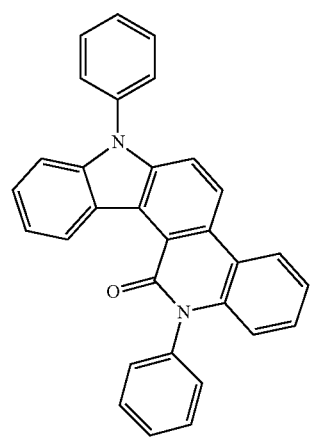
(163)
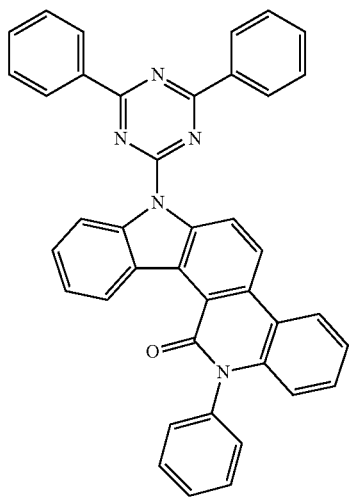
(164)
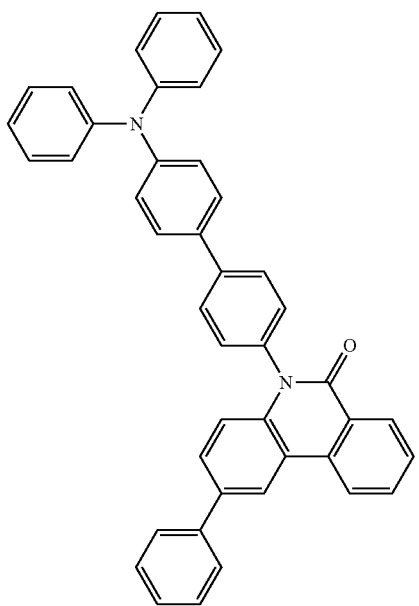

(165)
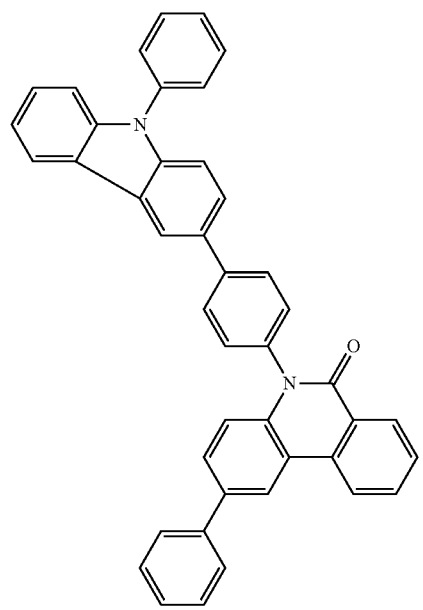
(167)
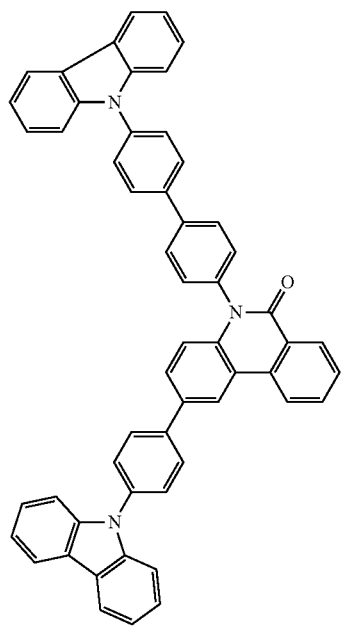
(166)
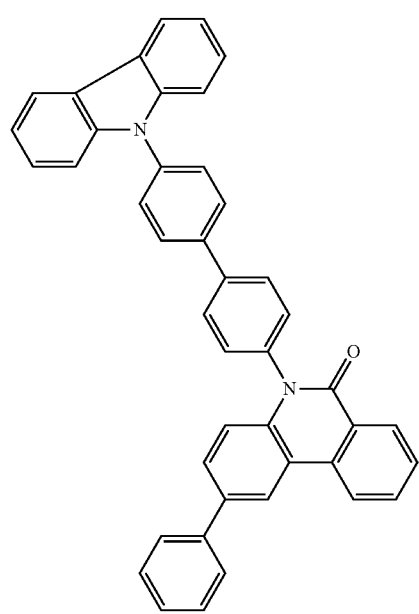
(168)
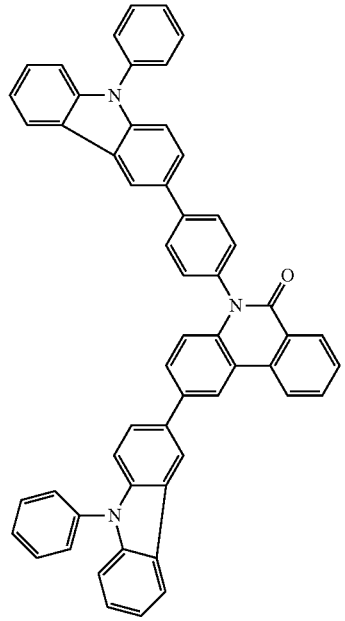

(169)
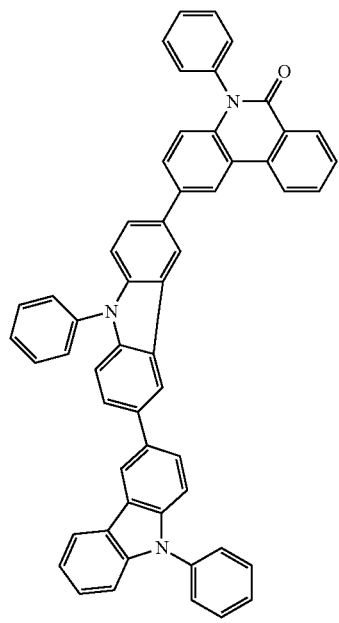
(170)
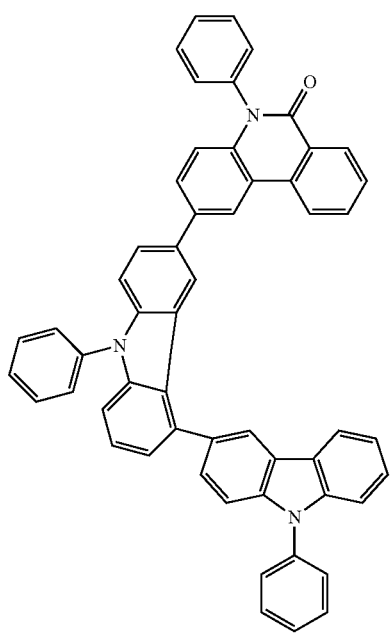
(171)
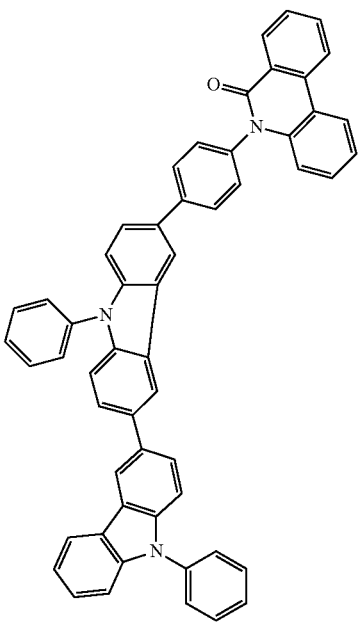
(172)
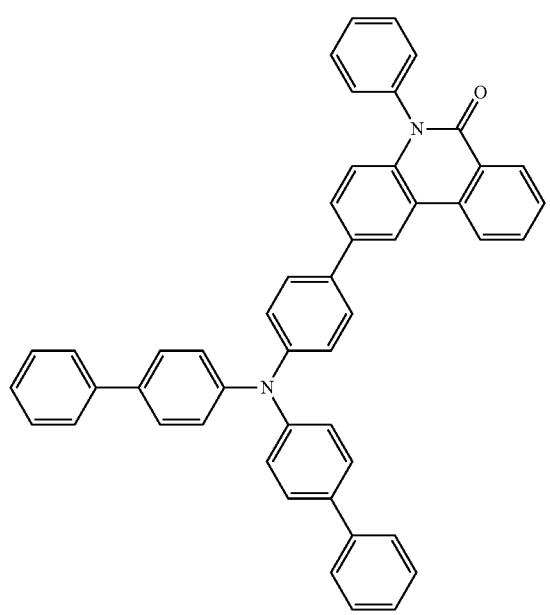

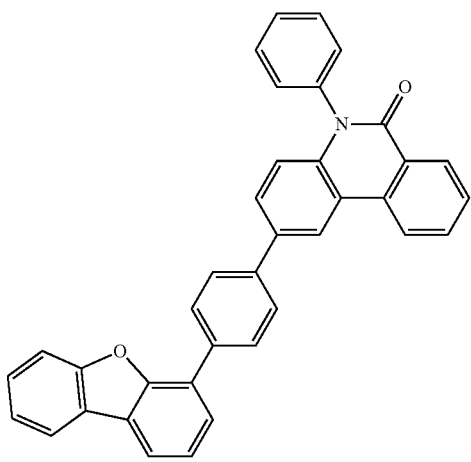
(173)
(174)
(175)
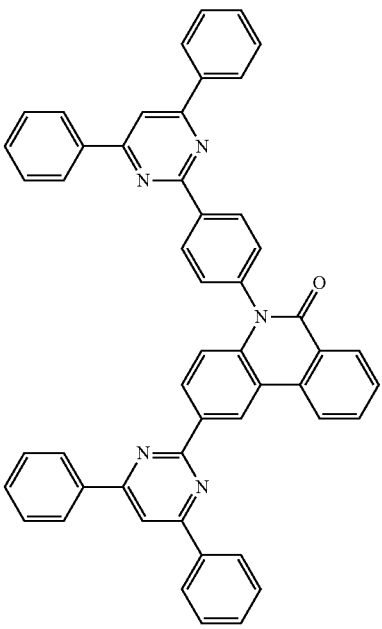
(176)
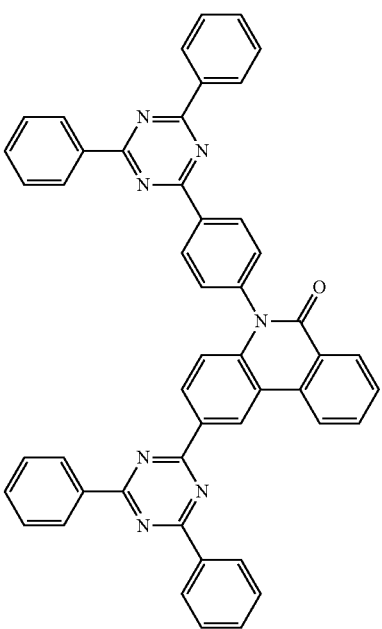
(177)

(178)
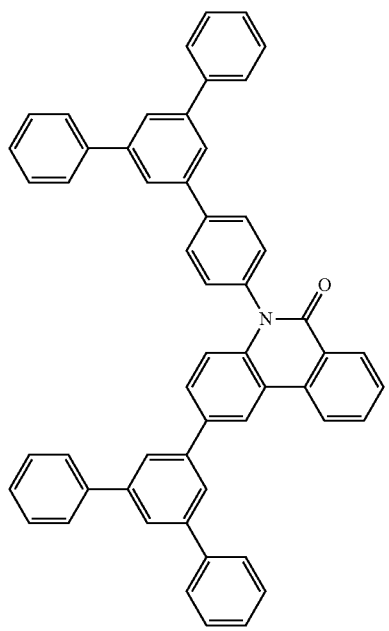
(179)
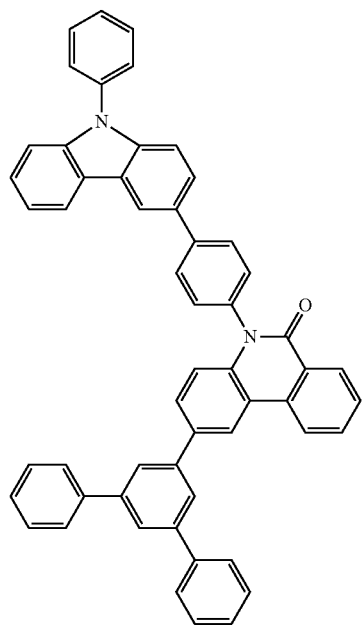
(180)
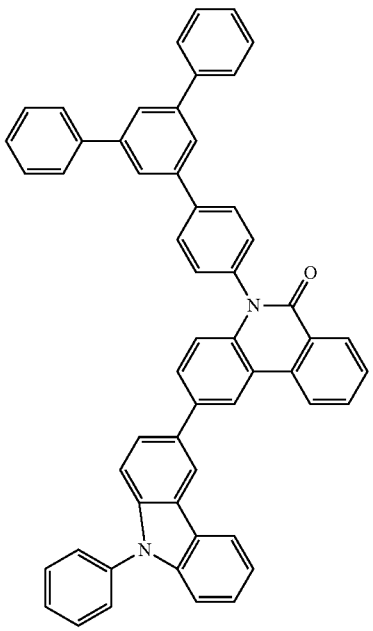
(181)
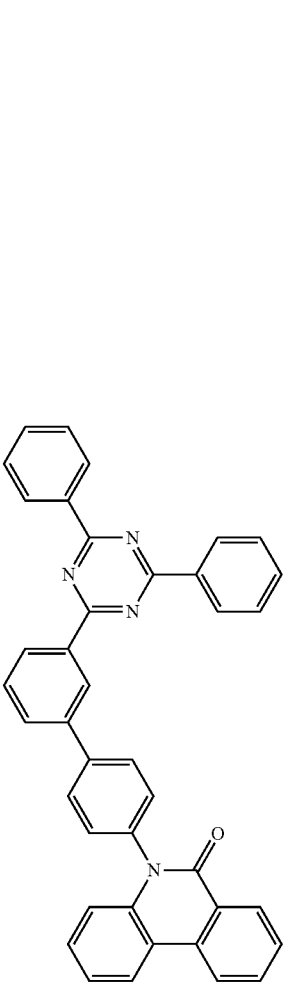

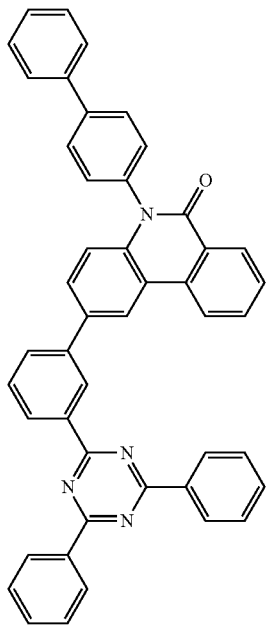
(182)
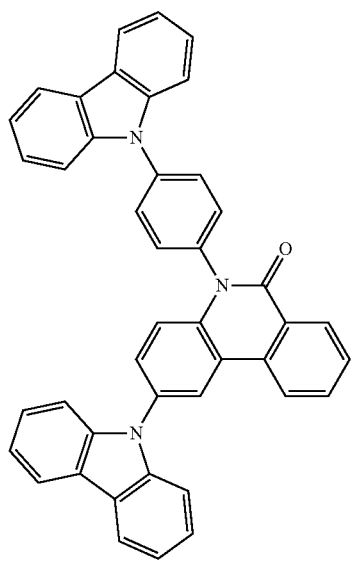
(184)
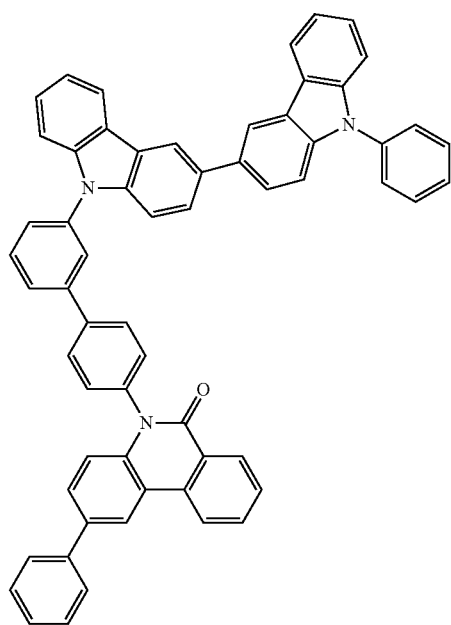
(183)
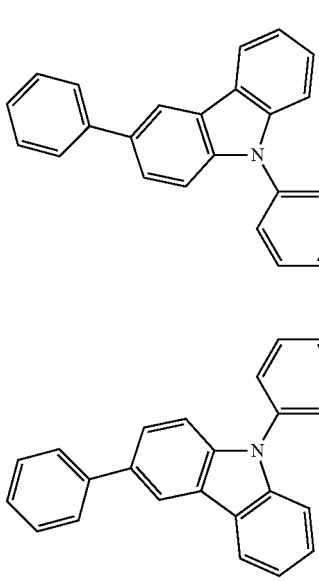
(185)

(186)
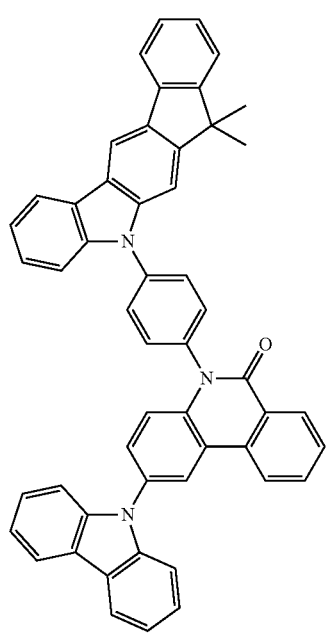
(187)
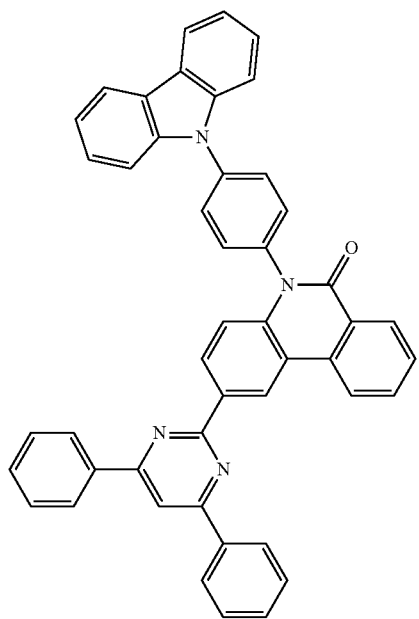
(188)
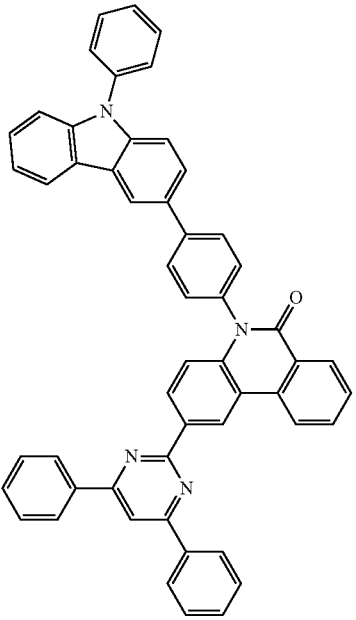
(189)
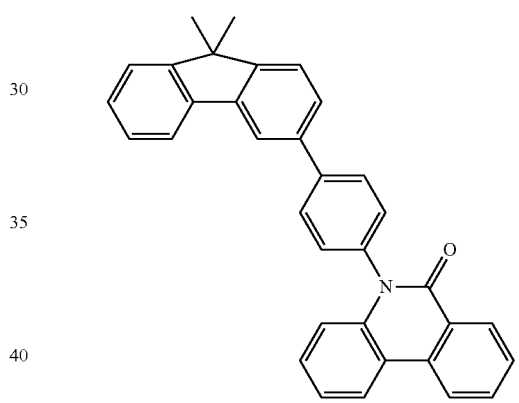
(190)
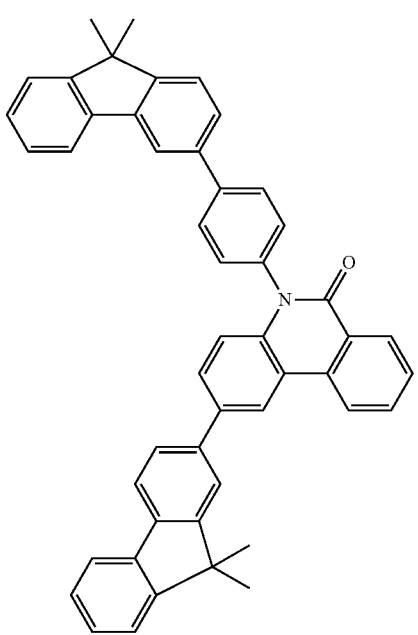

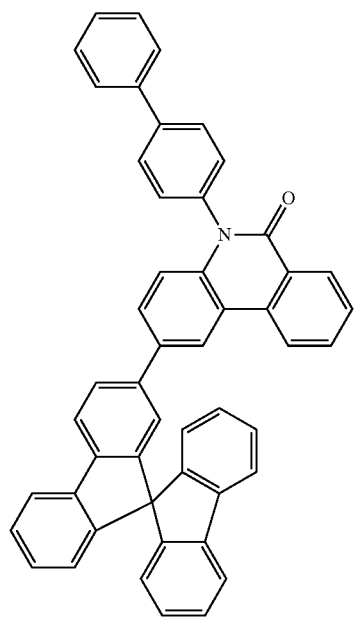
(191)
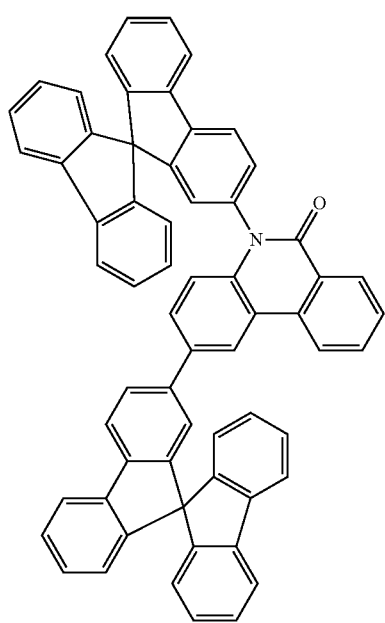
(192)
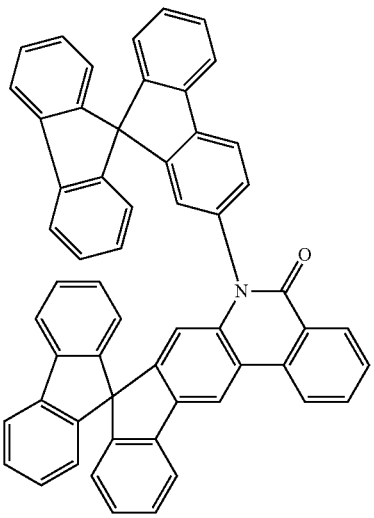
(193)
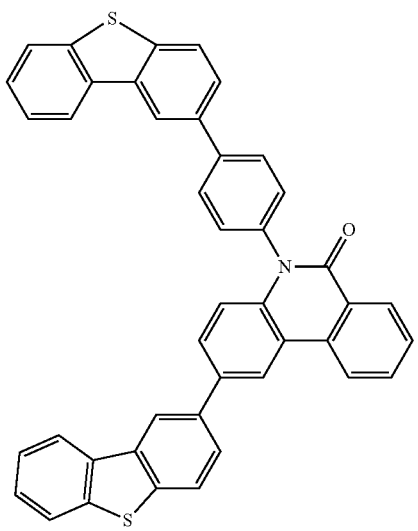
(194)
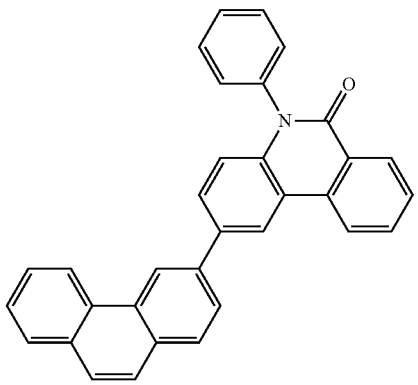
(195)

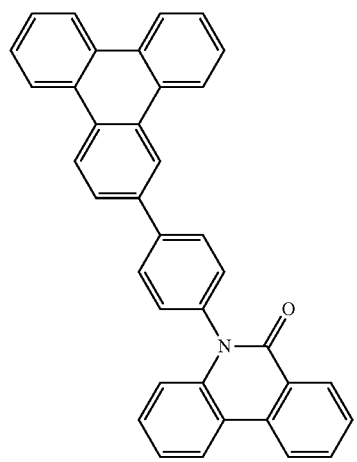
(196)
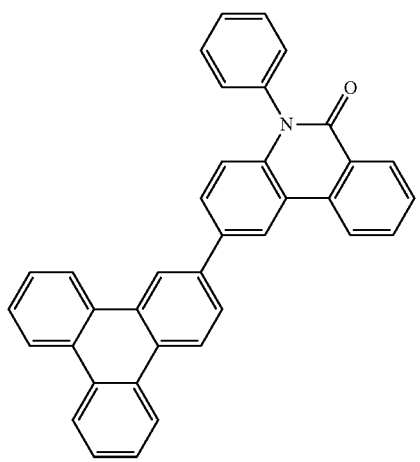
(197)
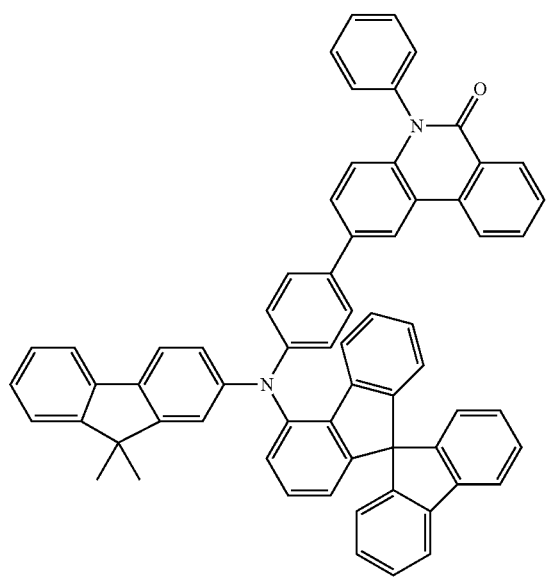
(198)
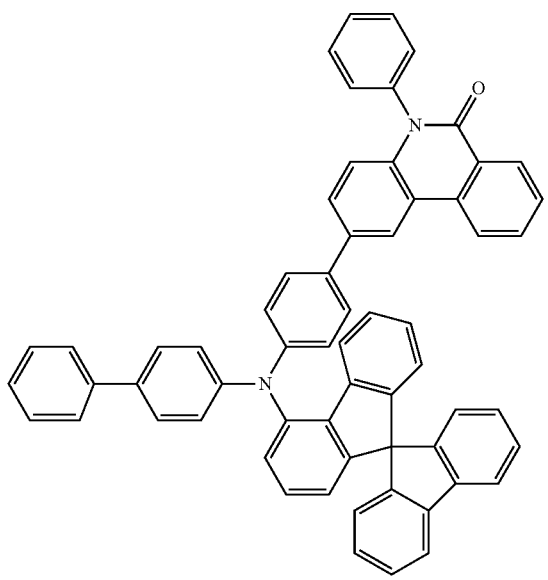
(199)
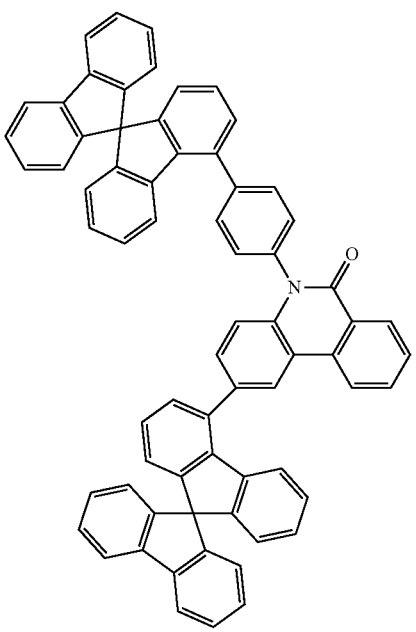
(200)

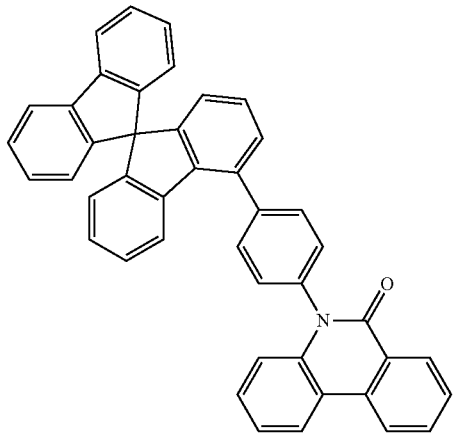

(201)

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be pointed out that each of these layers does not necessarily have to be present. The organic electroluminescent device may comprise one emitting layer, or it may comprise a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). Furthermore, white emission can preferably be generated through the use of a blue emission layer and an emission layer which emits red and green, where these two emission layers may be separated from one another by a charge-generation layer.

The compound of the formula (1) can be employed in different layers here, depending on the precise structure. Preference is given to an organic electroluminescent device comprising a compound of the formula (1) or the above-mentioned preferred embodiments as matrix material for fluorescent or phosphorescent emitters, in particular for phosphorescent emitters, and/or in a hole-blocking layer and/or in an electron-transport layer and/or in an electron-blocking or exciton-blocking layer and/or in a hole-transport layer, depending on the precise substitution.

In a further embodiment of the invention, the organic electroluminescent device comprises the compound of the formula (1) or the above-mentioned preferred embodiments in an optical coupling-out layer. An optical coupling-out layer here is taken to mean a layer which is not located between the anode and the cathode, but instead is applied to an electrode outside the actual device, for example between an electrode and a substrate, in order to improve the optical coupling-out.

In a preferred embodiment of the invention, the compound of the formula (1) or the above-mentioned preferred embodiments is employed as matrix material for a fluorescent or phosphorescent compound, in particular for a phosphorescent compound, in an emitting layer. The organic electroluminescent device here may comprise one emitting layer, or it may comprise a plurality of emitting layers, where at least one emitting layer comprises at least one compound of the formula (1) as matrix material.

If the compound of the formula (1) or the above-mentioned preferred embodiments is employed as matrix material for an emitting compound in an emitting layer, it is preferably employed in combination with one or more phosphorescent materials (triplet emitters). Phosphorescence in the sense of this invention is taken to mean the luminescence from an excited state having spin multiplicity >1, in particular from an excited triplet state. For the purposes of this application, all luminescent complexes with transition metals or lanthanides, in particular all iridium, platinum and copper complexes, are to be regarded as phosphorescent compounds.

The mixture of the compound of the formula (1) or the above-mentioned preferred embodiments and the emitting compound comprises between 99 and 1% by vol., preferably between 98 and 10% by vol., particularly preferably between 97 and 60% by vol., in particular between 95 and 80% by vol., of the compound of the formula (1) or the above-mentioned preferred embodiments, based on the entire mixture of emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture of emitter and matrix material. Depending on the choice of matrix material, a lower emitter concentration may also be preferred, as described, for example, in the unpublished application EP 11002816.4.

A further preferred embodiment of the present invention is the use of the compound of the formula (1) or the above-mentioned preferred embodiments as matrix material for a phosphorescent emitter in combination with a further matrix material. A further preferred embodiment of the present invention is the use of the compound of the formula (1) or in accordance with the preferred embodiments as matrix material for a phosphorescent emitter in combination with a further matrix material. Particularly suitable matrix materials which can be employed in combination with the compounds of the formula (1) or in accordance with the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109, WO 2011/000455 or the unpublished application EP 11007693.2, azacarbazole derivatives, for example in accordance with EP 1617710, EP 1617711, EP 1731584, JP 2005/347160, bipolar matrix materials, for example in accordance with WO 2007/137725, silanes, for example in accordance with WO 005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetra-azasilole derivatives, for example in accordance with WO 2010/054729, diaza-phosphole derivatives, for example in accordance with WO 2010/054730, bridged carbazole derivatives, for example in accordance with US 2009/0136779, WO 2010/050778, WO 2011/

042107, WO 2011/088877 or in accordance with the unpublished application EP 11003232.3, triphenylene derivatives, for example in accordance with the unpublished application DE 102010048608.6, or lactams, for example in accordance with the unpublished applications DE 102010012738.8 or DE 102010019306.2. A further phosphorescent emitter which emits at shorter wavelength than the actual emitter may likewise be present in the mixture as co-host.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as are used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

In a further preferred embodiment of the invention, the compound of the formula (1) or the above-mentioned preferred embodiments is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, LiQ (lithium hydroxyquinolinate).

In still a further preferred embodiment of the invention, the compound of the formula (1) or the above-mentioned preferred embodiments is employed in a hole-blocking layer. A hole-blocking layer is taken to mean a layer which is directly adjacent to an emitting layer on the cathode side.

It is furthermore possible to use the compound of the formula (1) or the above-mentioned preferred embodiments both in a hole-blocking layer or electron-transport layer and also as matrix in an emitting layer.

In still a further embodiment of the invention, the compound of the formula (1) or the above-mentioned preferred embodiments is employed in a hole-transport layer or in an electron-blocking layer or exciton-blocking layer.

In the further layers of the organic electroluminescent device according to the invention, all materials as are usually employed in accordance with the prior art can be used. The person skilled in the art will therefore be able, without inventive step, to employ all materials known for organic electroluminescent devices in combination with the compounds of the formula (1) according to the invention or the above-mentioned preferred embodiments.

Preference is furthermore given to an organic electroluminescent device, characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), ink-jet printing or nozzle printing. Soluble compounds, which are obtained, for example, by suitable substitution, are necessary for this purpose. These processes are also suitable, in particular, for oligomers, dendrimers and polymers.

Also possible are hybrid processes, in which, for example, one or more layers are applied from solution and one or more further layers are applied by vapour deposition.

These processes are generally known to the person skilled in the art and can be applied by him without inventive step to organic electroluminescent devices comprising the compounds according to the invention.

The present invention furthermore relates to the compounds of the following formula (1') mentioned as preferred above,

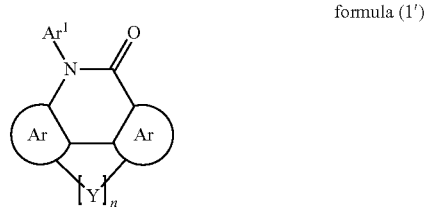

formula (1')

where the following applies to the symbols and indices used:
Ar is on each occurrence, identically or differently, an aryl or heteroaryl group having 5 to 13 aromatic ring atoms, which may be substituted by one or more radicals R;
Ar¹ is an aromatic or heteroaromatic ring system having 5 to 24 aromatic ring atoms, which may be substituted by one or more radicals R and which contains no aryl or heteroaryl groups having more than two aromatic six-membered rings condensed directly onto one another;

Y is —C(=O)—N(Ar¹)—, —C(=O)—O—, —CR¹=CR¹—, —CR¹=N—, C(R¹)₂, NR¹, O, S, C(=O), C(=S), C(=NR¹), C(=C(R¹)₂), Si(R¹)₂, BR¹, PR¹, P(=O)R¹, SO or SO₂;

R, R¹ is selected on each occurrence, identically or differently, from the group consisting of H, D, F, I, N(Ar²)₂, C(=O)Ar², C(=O)R², P(=O)(Ar²)₂, a straight-chain alkyl group having 1 to 40 C atoms or a branched or cyclic alkyl group having 3 to 40 C atoms or an alkenyl or alkynyl group having 2 to 40 C atoms, each of which may be substituted by one or more radicals R², where one or more non-adjacent CH₂ groups may be replaced by R²C=CR², C≡C, Si(R²)₂, C=O, C=S, C=NR², P(=O)(R²), SO, SO₂, S or CONR² and where one or more H atoms may be replaced by D, F, Cl, Br, I, CN or NO₂, an aromatic or heteroaromatic ring system having 5 to 60 aromatic ring atoms, which may in each case be substituted by one or more radicals R², an aryloxy or heteroaryloxy group having 5 to 60 aromatic ring atoms, which may be substituted by one or more radicals R², or a combination of these systems, where two or more adjacent substituents R or two or more adjacent substituents R¹ may optionally form a monocyclic or polycyclic, aliphatic, aromatic or heteroaromatic ring system, which may be substituted by one or more radicals R²; a radical R on Ar¹ may furthermore also form an aliphatic ring system with a radical R on Ar; with the proviso that an aryl or heteroaryl group having more than two aryl groups condensed directly onto one another is not formed by ring formation of the radicals R or R¹;

Ar² is on each occurrence, identically or differently, an aromatic or heteroaromatic ring system having 5-30 aromatic ring atoms, which may be substituted by one or more non-aromatic radicals R²; two radicals Ar² which are bonded to the same N atom or P atom may also be bridged to one another here by a single bond or a bridge selected from N(R²), C(R²)₂ or O;

R² is selected from the group consisting of H, D, F, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents R³ may form a mono- or polycyclic, aliphatic, aromatic or heteroaromatic ring system with one another;

n is on each occurrence, identically or differently, 0 or 1, where n=1 means that no group Y is present and instead a substituent R is bonded or a heteroatom of the group Ar is present in the positions on Ar in which Y is bonded in formula (1);

with the proviso that the radicals on Ar or Ar¹ do not contain a lactam group;

the following compounds are excluded from the invention:

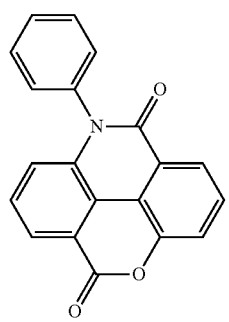

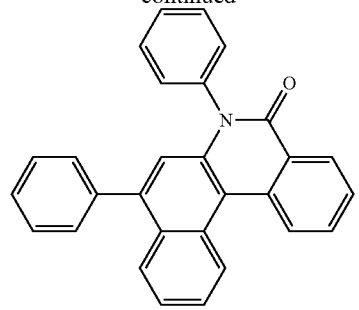

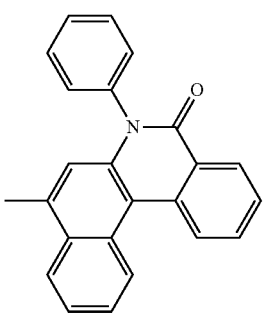
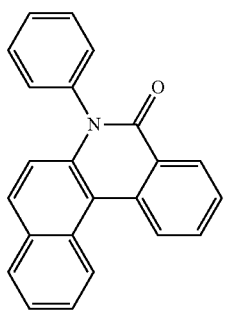

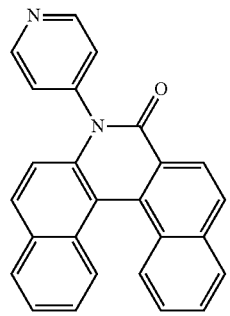
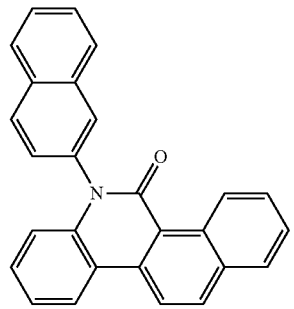

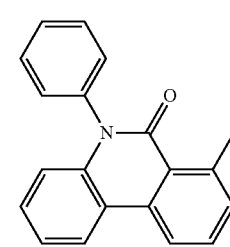
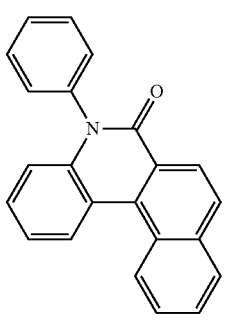

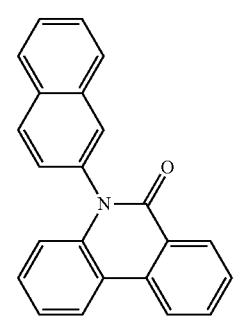
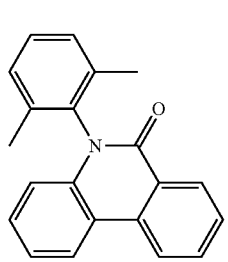

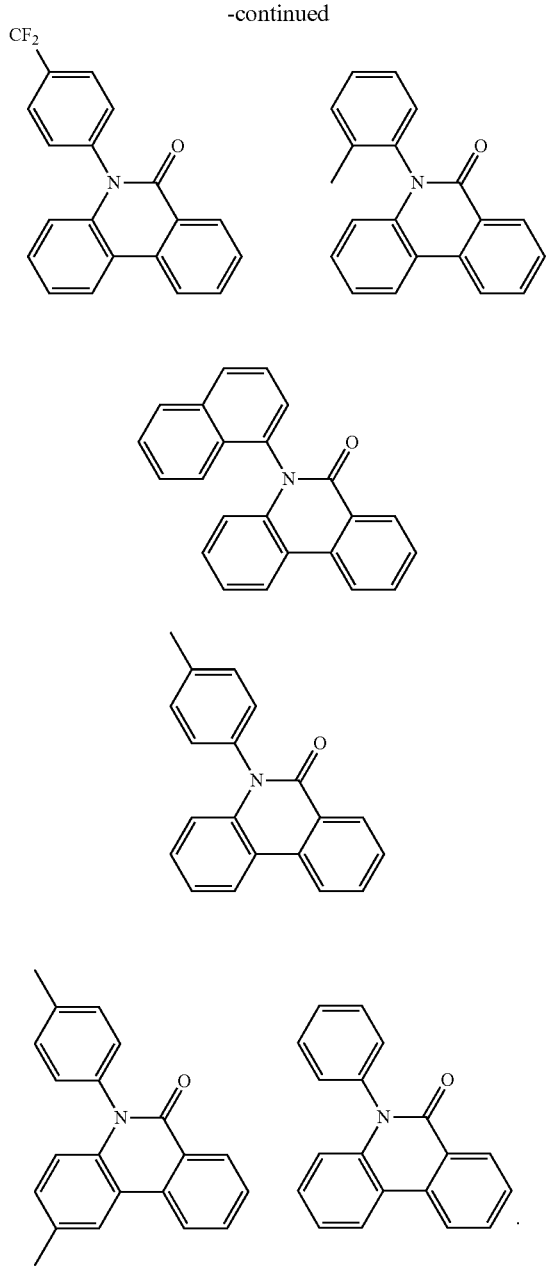

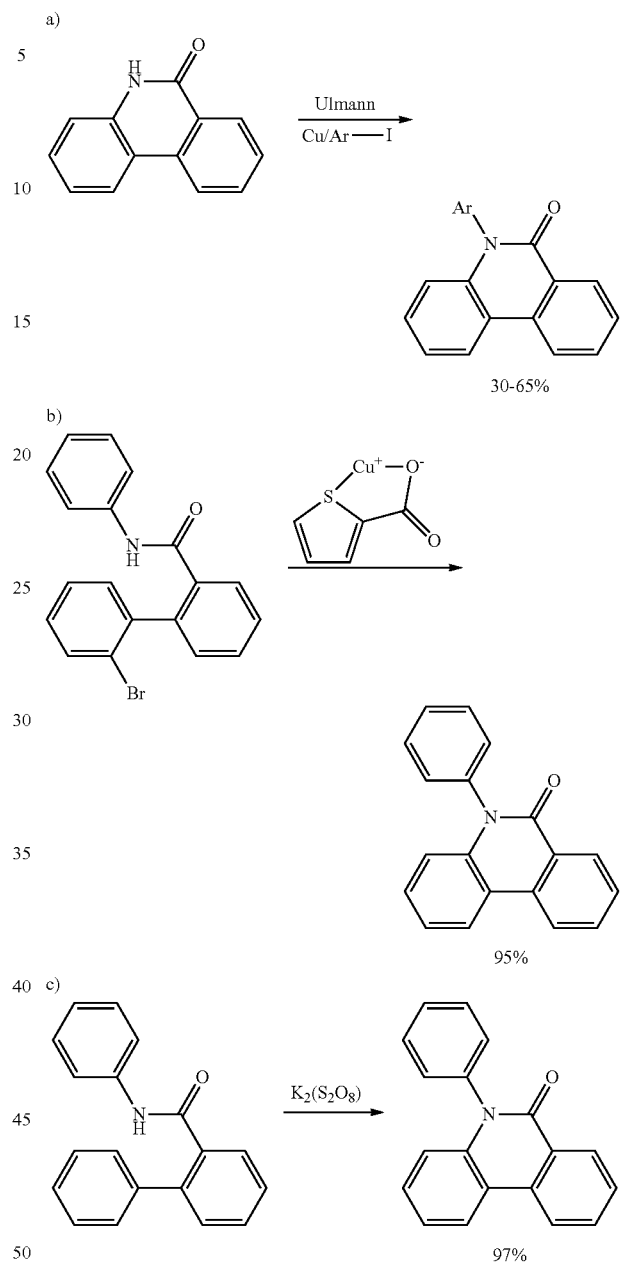

The same preferences as indicated above for the compounds of the formula (1) apply to the compounds of the formula (1') according to the invention.

The compounds of the formula (1) or (1') or the preferred embodiments can be prepared by synthesis steps known to the person skilled in the art, as depicted diagrammatically in Scheme 1 to 3.

The literature discloses a process for the synthesis of aryl-substituted lactams from the lactam which is unsubstituted on the nitrogen using an aryl iodide (for example in accordance with WO 2007/062230; Scheme 1a) by Ullmann coupling. Further literature-known syntheses start from the corresponding amide, which is cyclised to the lactam (for example Chemistry—An Asian Journal 2010, 5(9), 2113-2123; Organic Reactions (Hoboken, N.J., United States), 48, 1996; Scheme 1b and 1c).

The synthesis of the compounds by a novel synthesis route which gives high yields is described below, as depicted in Scheme 2 and 3. In these processes, the nitrogen of an unsubstituted lactam is not substituted or an amide is not functionalised to a lactam, but instead a ring-closure reaction takes place between two aryl groups, where one of the aryl groups is bonded to the carbonyl group of an amide and the other aryl group is bonded to the nitrogen of an amide. The cyclisation here can be carried out either with palladium catalysis (Scheme 2) or by a free-radical mechanism with catalysis of a tin hydride (Scheme 3). Furthermore, both synthesis methods can be carried out both on the amine, which is then oxidised to the lactam in a subsequent step, as depicted in Scheme 2, or they can be carried out on the amide, as depicted in Scheme 3. Very good yields are obtained in the ring-closure reaction for both reaction types.

Scheme 2:
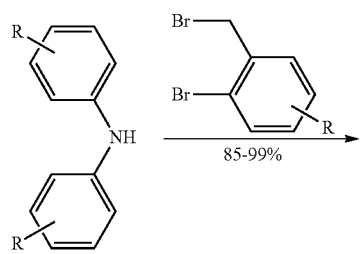
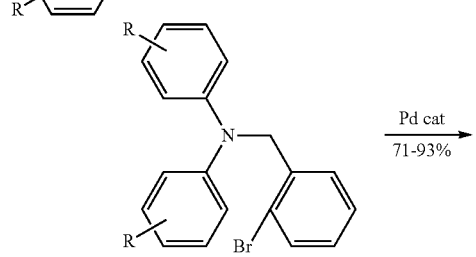
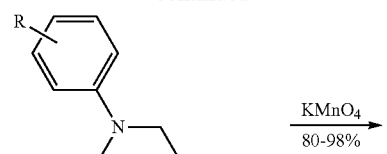
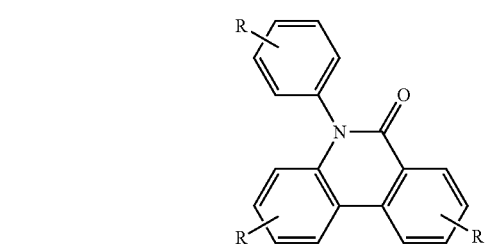
Scheme 3:
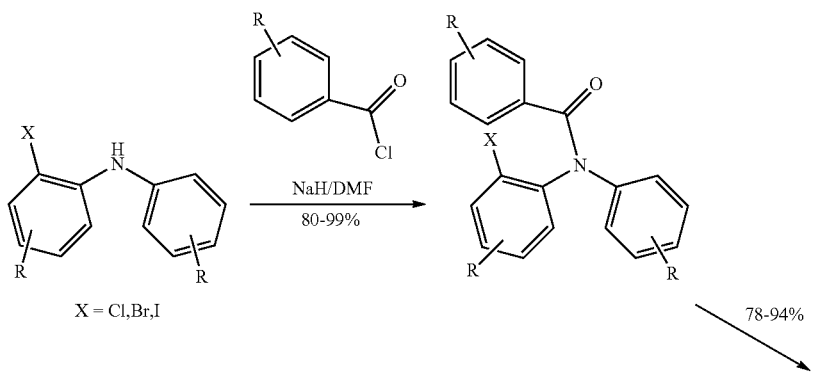
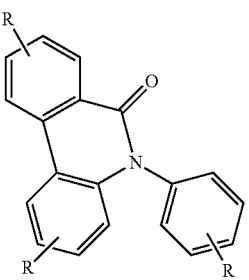
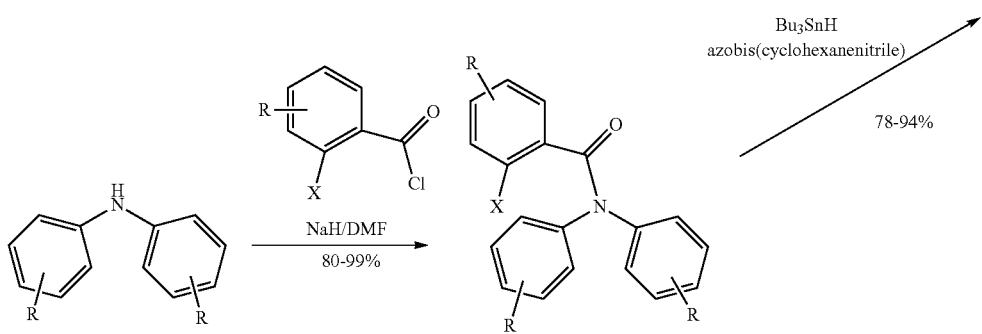

A method for the functionalisation of the compounds according to the invention by halogenation, for example bromination using NBS, followed by a metal-catalysed coupling reaction, for example a Suzuki coupling or a Hartwig-Buchwald coupling, is depicted in Scheme 4.

Scheme 4:
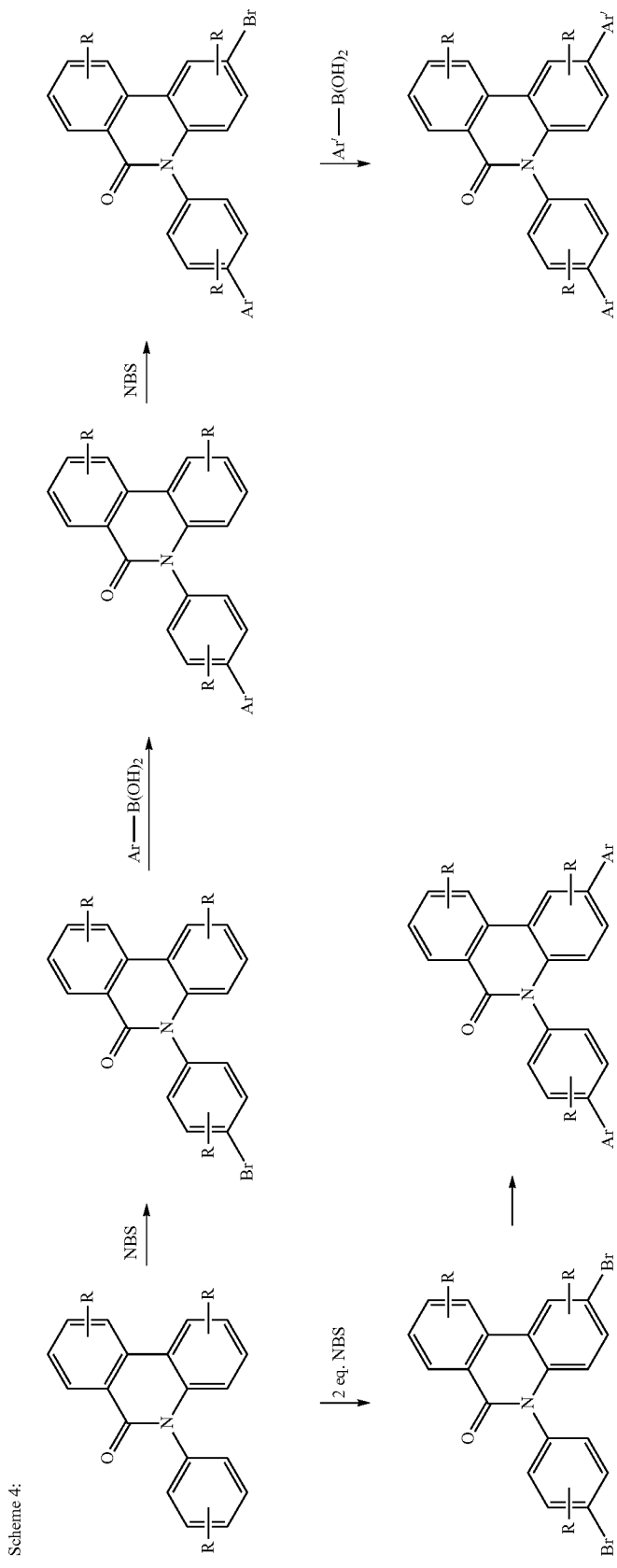

The present invention furthermore relates to a process for the preparation of a compound of the formula (1'), comprising:
a) bond formation between the nitrogen of a lactam and Ar¹; or
b) bond formation between the nitrogen of an amide and Ar; or
c) bond formation between the two groups Ar which are linked to one another via an amide group; or
d) bond formation between the two groups Ar which are linked to one another via a methyleneamine group, followed by an oxidation to the corresponding lactam.

The present invention furthermore relates to the use of the above-mentioned compounds of the formula (1') according to the invention in an electronic device, in particular in an organic electroluminescent device.

The compounds according to the invention and the organic electroluminescent devices according to the invention are distinguished by one or more of the following surprising advantages over the prior art:
1. The compounds according to the invention or compounds of the formula (1) or the above-mentioned preferred embodiments, employed as matrix material for fluorescent or phosphorescent emitters, result in very high efficiencies and in long lifetimes. This applies, in particular, if the compounds are employed as matrix material for a red- or green-phosphorescent emitter.
2. The compounds according to the invention have high thermal stability.
3. The compounds according to the invention, employed in organic electro-luminescent devices, result in high efficiencies and in steep current/voltage curves with low use voltages.
4. Also when used as electron-transport material, the compounds according to the invention result in very good properties in relation to the efficiency, the lifetime and the operating voltage of organic electroluminescent devices.
5. The compounds of the formula (1) can be synthesised simply and in high yield.

These above-mentioned advantages are not accompanied by an impairment of the other electronic properties.

The invention is explained in greater detail by the following examples without wishing to restrict it thereby. The person skilled in the art will be able to carry out the invention throughout the range disclosed on the basis of the descriptions and prepare further compounds according to the invention without inventive step and use them in electronic devices or use the process according to the invention.

EXAMPLES

The following syntheses are carried out, unless indicated otherwise, under a protective-gas atmosphere. The starting materials can be purchased from ALDRICH or ABCR (palladium(II) acetate, tri-o-tolylphosphine, inorganics, solvents). The numbers in the case of the literature-known starting materials are the CAS numbers.

Example 1

2-Bromo-N,N-bis(biphenyl)benzenemethanamine

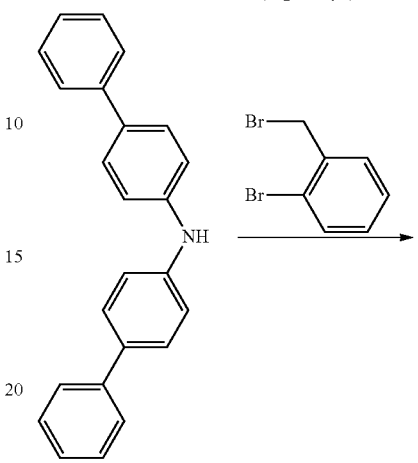

9.7 g (0.243 mol) of 60% NaH in mineral oil are dissolved in 500 ml of dimethylformamide under protective atmosphere. 60 g (0.106 mol) of N,N-bis(4-biphenyl)amine are dissolved in 500 ml of DMF and added dropwise to the reaction mixture. After 1 h at room temperature, a solution of 60.6 (242 mmol) of 2-bromobenzyl bromide in 500 ml of DMF is added dropwise. The reaction mixture is stirred at room temperature for 1 h. After this time, the reaction mixture is poured onto ice and extracted three times with dichloromethane. The combined organic phases are dried over $Na_2SO_4$ and evaporated. The residue is extracted with hot toluene and recrystallised from toluene/n-heptane. The yield is 80 g (93%).

The following compounds are obtained analogously:

| Ex. | Starting material 1 | Starting material 2 |
|---|---|---|
| 1a | 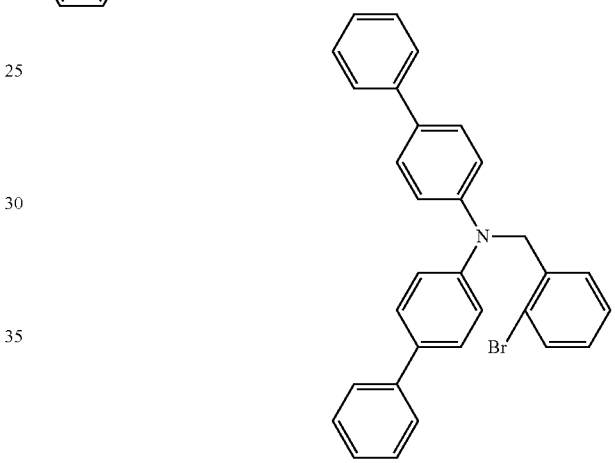 | |

1303969-38-1

3433-80-5

| | | |
|---|---|---|
| 1b | 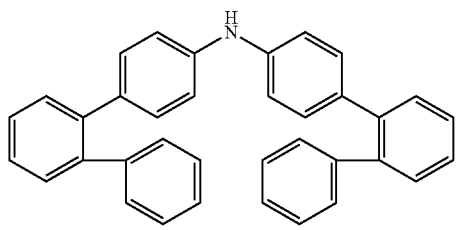 1222634-01-6 | 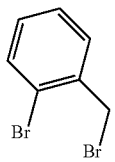 3433-80-5 |
| 1c | 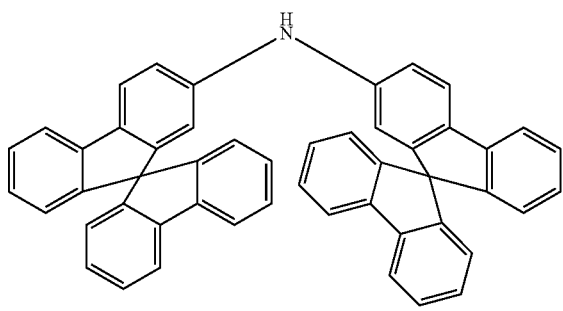 932731-04-9 | 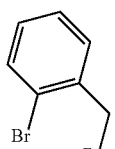 3433-80-5 |
| 1d | 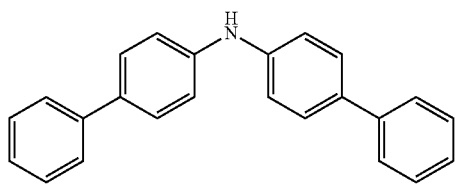 [SMILES: c1ccc(-c2ccc(Nc3ccc(-c4ccccc4)cc3)cc2)cc1] | 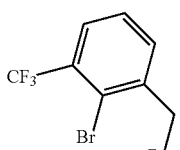 1214372-35-6 |
| 1e | 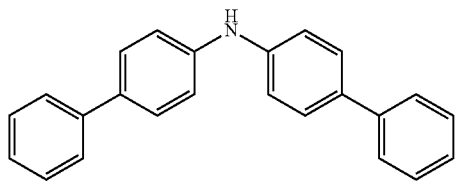 [SMILES: c1ccc(-c2ccc(Nc3ccc(-c4ccccc4)cc3)cc2)cc1] | 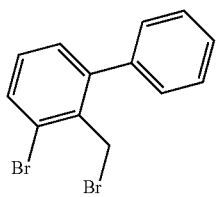 172976-02-2 |
| 1f | 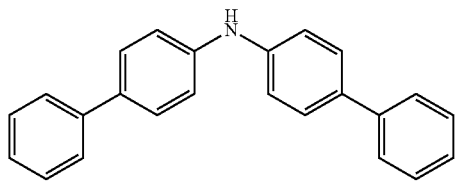 [SMILES: c1ccc(-c2ccc(Nc3ccc(-c4ccccc4)cc3)cc2)cc1] | 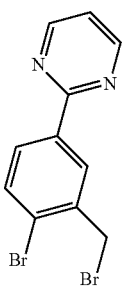 202805-71-8 |

| | | |
|---|---|---|
| 1g | 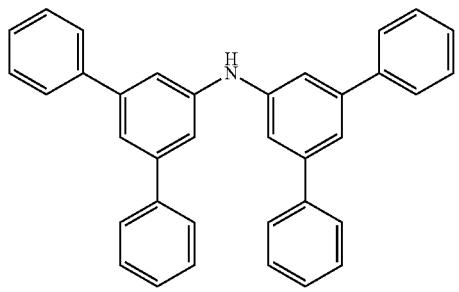<br>1290039-78-9 | 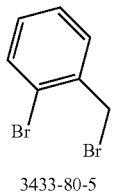<br>3433-80-5 |
| 1h | 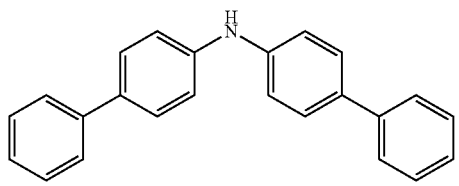 [SMILES: c1ccc(-c2ccc(Nc3ccc(-c4ccccc4)cc3)cc2)cc1]<br> | 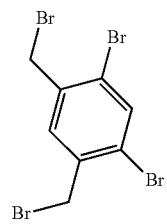<br>35510-03-3 |
| 1i | 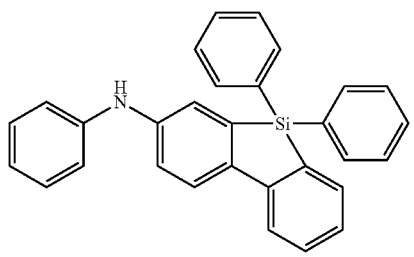<br>860465-15-2 | 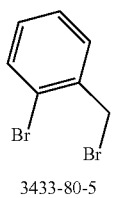<br>3433-80-5 |
| 1j | 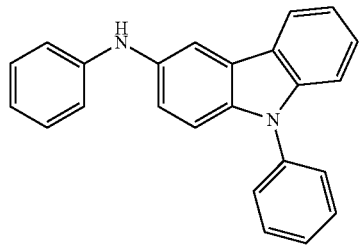<br>894791-43-6 | 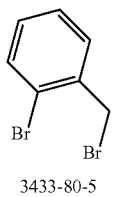<br>3433-80-5 |
| 1k | 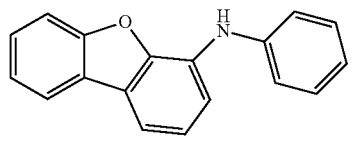<br>743453-07-8 | 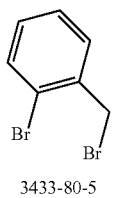<br>3433-80-5 |
| 1l | 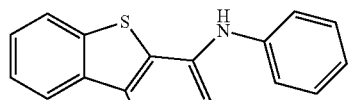<br>1300028-91-4 | 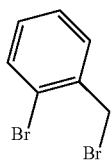<br>3433-80-5 |

-continued
| Ex. | Product | Yield |
|---|---|---|
| 1a | 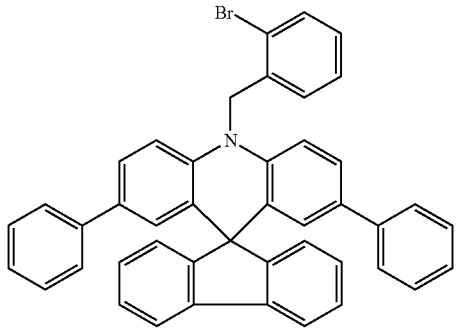 [SMILES: Brc1ccccc1CN1c2ccc(-c3ccccc3)cc2C2(c3ccccc3-c3ccccc32)c2cc(-c3ccccc3)ccc21] | 88% |
| 1b | 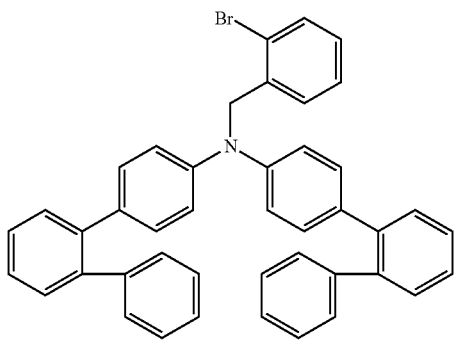 [SMILES: Brc1ccccc1CN(c1ccc(-c2ccccc2-c2ccccc2)cc1)c1ccc(-c2ccccc2-c2ccccc2)cc1] | 87% |
| 1c | 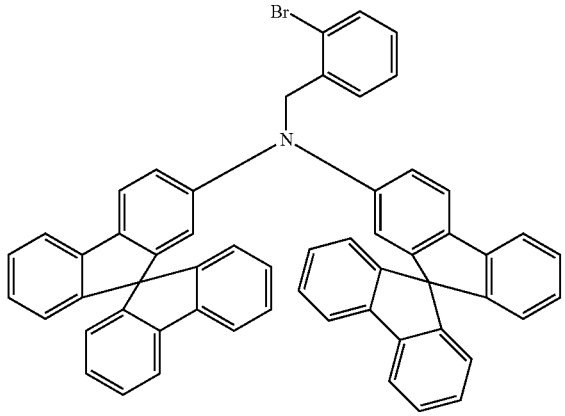 [SMILES: Brc1ccccc1CN(c1ccc2c(c1)C1(c3ccccc3-c3ccccc31)c1ccccc1-2)c1ccc2c(c1)C1(c3ccccc3-c3ccccc31)c1ccccc1-2] | 91% |
| 1d | 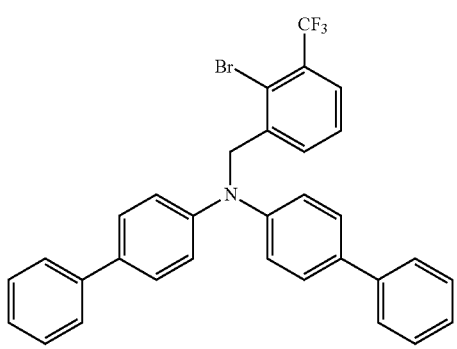 [SMILES: FC(F)(F)c1cccc(CN(c2ccc(-c3ccccc3)cc2)c2ccc(-c3ccccc3)cc2)c1Br] | 90% |

-continued
| | | |
|---|---|---|
| 1e | 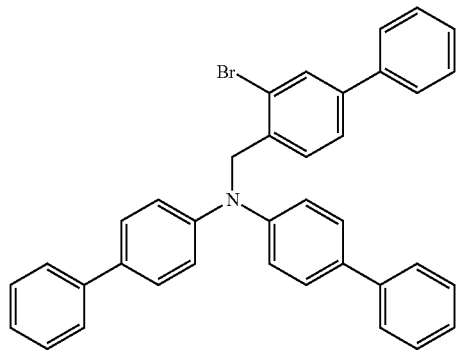 [SMILES: Brc1cc(-c2ccccc2)ccc1CN(c1ccc(-c2ccccc2)cc1)c1ccc(-c2ccccc2)cc1] | 93% |
| 1f | 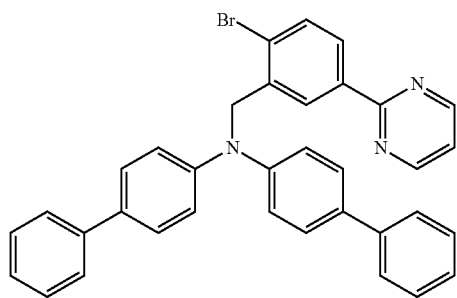 [SMILES: Brc1ccc(-c2ncccn2)cc1CN(c1ccc(-c2ccccc2)cc1)c1ccc(-c2ccccc2)cc1] | 82% |
| 1g | 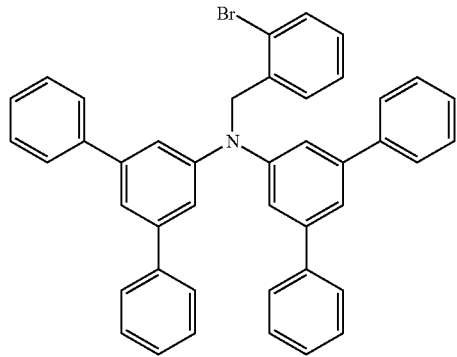 [SMILES: Brc1ccccc1CN(c1cc(-c2ccccc2)cc(-c2ccccc2)c1)c1cc(-c2ccccc2)cc(-c2ccccc2)c1] | 87% |
| 1h | 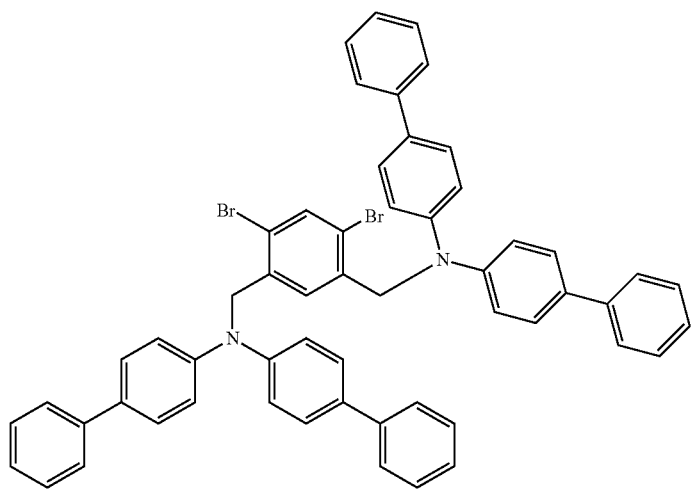 [SMILES: Brc1cc(Br)c(CN(c2ccc(-c3ccccc3)cc2)c2ccc(-c3ccccc3)cc2)cc1CN(c1ccc(-c2ccccc2)cc1)c1ccc(-c2ccccc2)cc1] | 79% |

| | | |
|---|---|---|
| 1i | 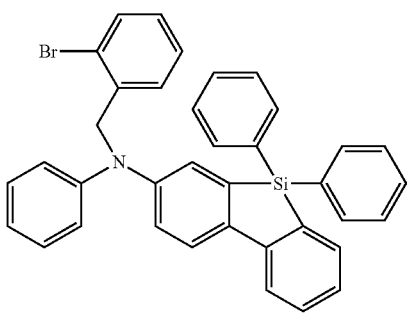 [SMILES: Brc1ccccc1CN(c1ccccc1)c1ccc2c(c1)[Si](c1ccccc1)(c1ccccc1)c1ccccc1-2] | 79% |
| 1j | 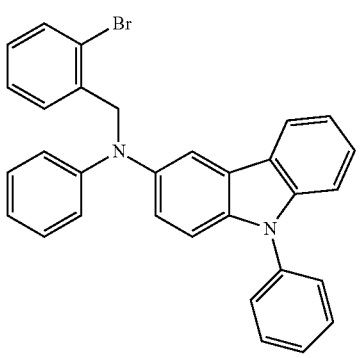 [SMILES: Brc1ccccc1CN(c1ccccc1)c1ccc2c(c1)c1ccccc1n2-c1ccccc1] | 89% |
| 1k | 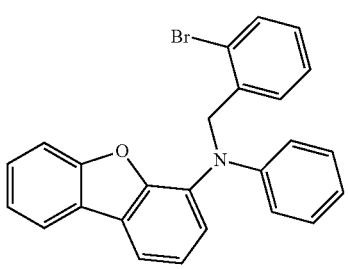 | 84% |
| 1l | 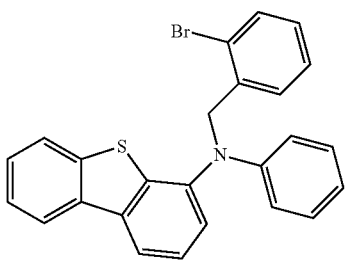 [SMILES: Brc1ccccc1CN(c1ccccc1)c1cccc2c1sc1ccccc12] | 86% |

Example 2

5-Biphenyl-4-yl-2-phenyl-5,6-dihydrophenanthridine

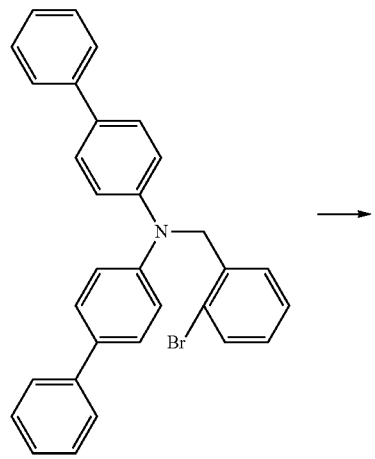 → 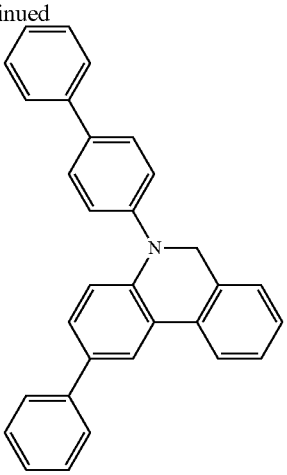

47 g (0.158 mol) of 2-bromo-N,N-bisbiphenylbenzenemethanamine are dissolved in 500 ml of dimethylformamide under protective atmosphere. 17.3 g (0.075 mol) of benzyltrimethylammonium bromide and 31.28 g (0.226 mol) of potassium carbonate are added to this solution. 5.08 g (0.022 mol) of Pd(OAc)$_2$ is subsequently added under protective gas, and the mixture is stirred at 120° C. for 9 h. After this time, the reaction mixture is cooled to room temperature and extracted with dichloromethane. The combined organic phases are dried over Na$_2$SO$_4$ and evaporated. The residue is recrystallised from n-heptane. The yield is 51 g (84%).

The following compounds are obtained analogously:

| Ex. | Starting material 1 | Product | Yield |
|---|---|---|---|
| 2a | 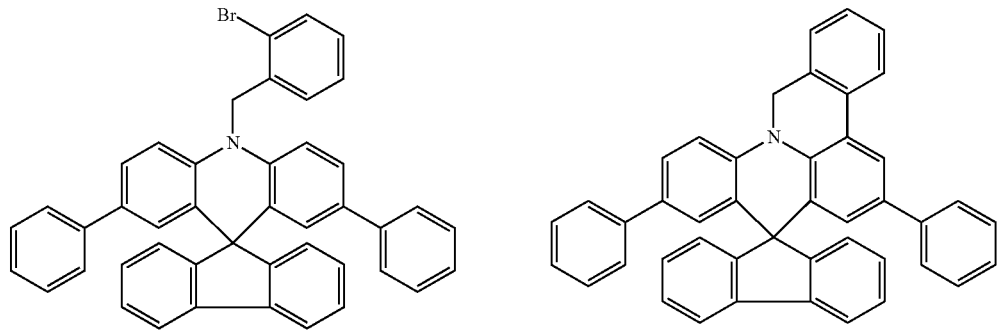 | | 83% |
| 2b | 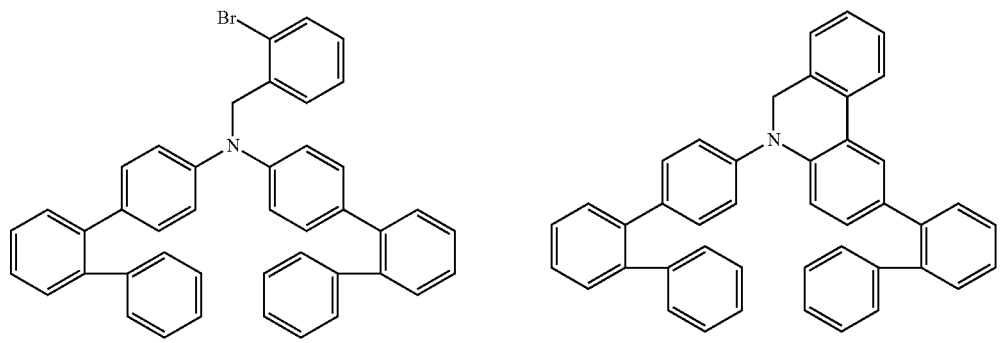 | | 82% |

-continued
| Starting Ex. material 1 | Product | Yield |
|---|---|---|
| 2c | 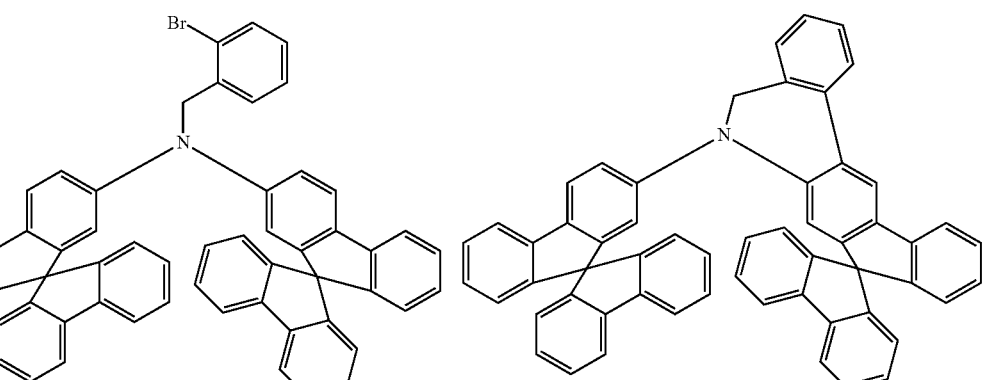 | 80% |
| 2d | 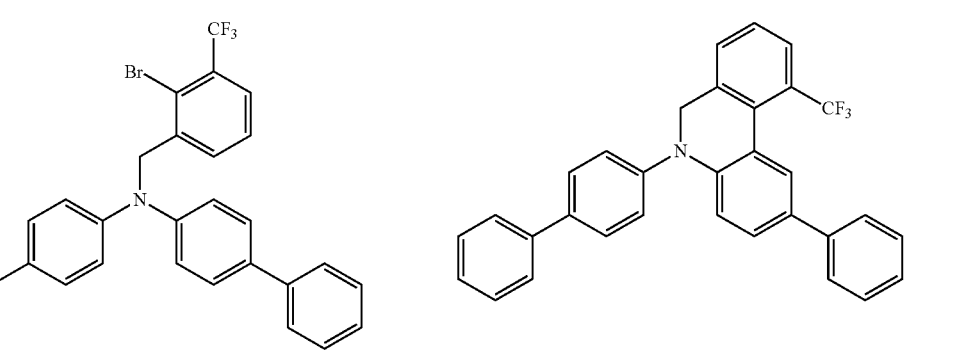 | 78% |
| 2e | 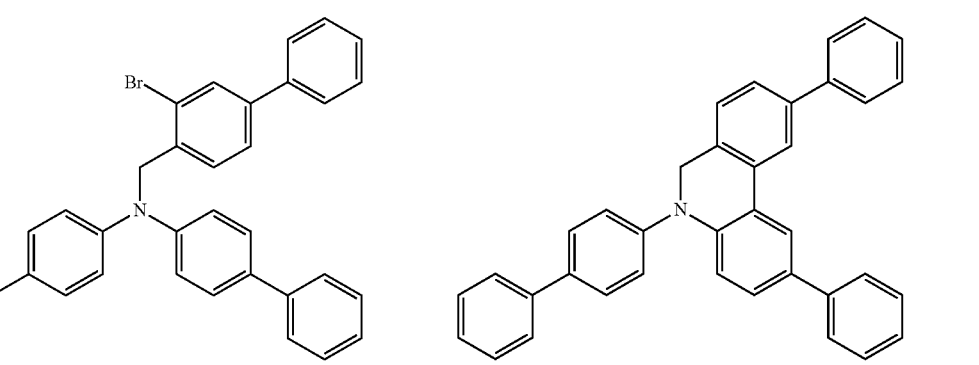 | 90% |
| 2f | 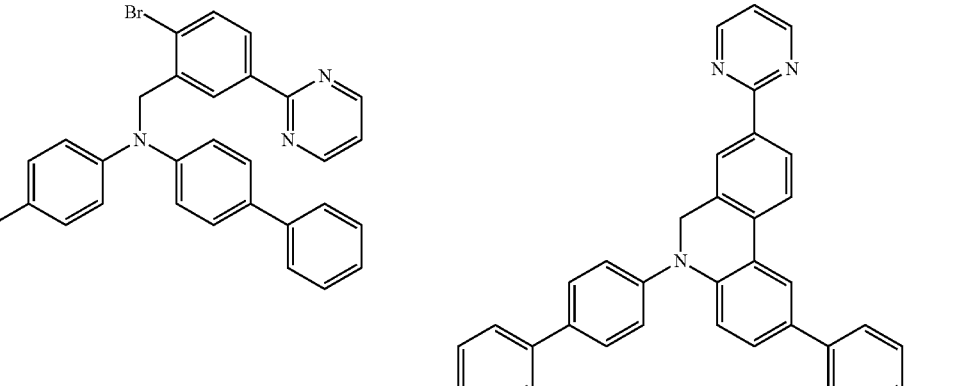 | 69% |

-continued

| Starting Ex. material 1 | Product | Yield |
|---|---|---|
| 2g | | 67% |
| 2h | | 71% |
| 2i | | 77% |

-continued

| Starting Ex. material 1 | Product | Yield |
|---|---|---|
| 2j 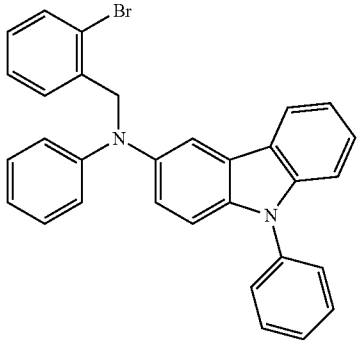 [SMILES: Brc1ccccc1CN(c1ccccc1)c1ccc2c(c1)c1ccccc1n2-c1ccccc1] | 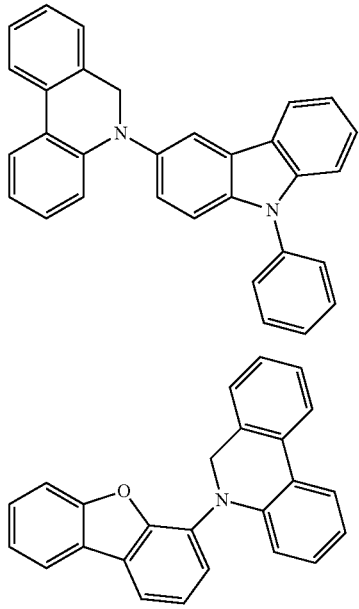 | 60% |
| 2k 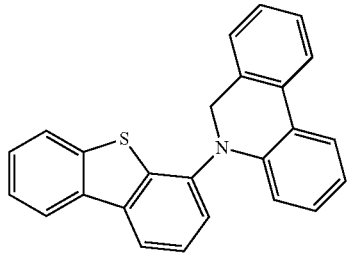 [SMILES: c1ccc2c(c1)CN(c1cccc3c1sc1ccccc13)c1ccccc1-2] | 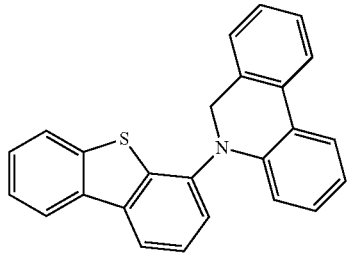 [SMILES: c1ccc2c(c1)CN(c1cccc3c1sc1ccccc13)c1ccccc1-2] | 53% |
| 2l 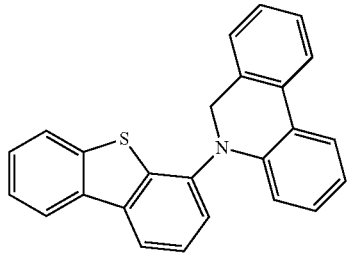 [SMILES: c1ccc2c(c1)CN(c1cccc3c1sc1ccccc13)c1ccccc1-2] | 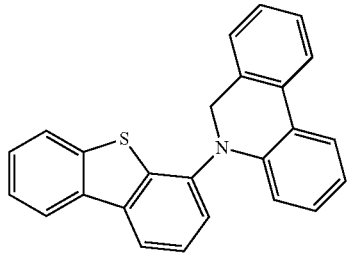 [SMILES: c1ccc2c(c1)CN(c1cccc3c1sc1ccccc13)c1ccccc1-2] | 55% |

Example 3

5-Biphenyl-4-yl-2-phenyl-6(5H)-phenanthridinone

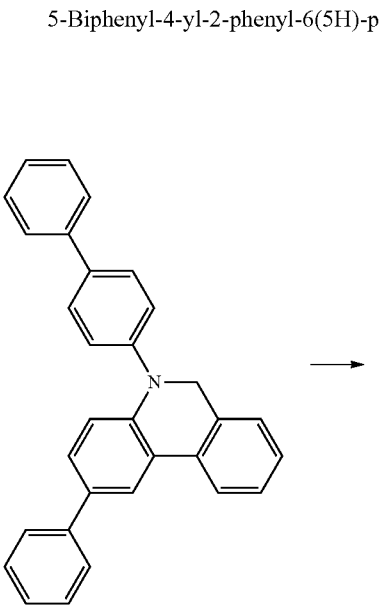

→

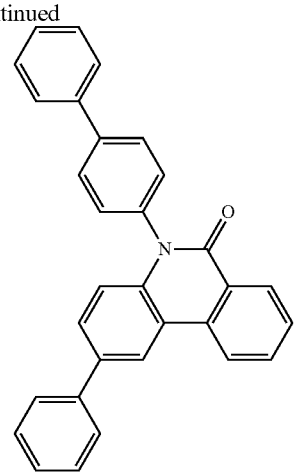

16 g (0.039 mol) of 5-biphenyl-4-yl-2-phenyl-5,6-dihydrophenanthridine are dissolved in 300 ml of dichloromethane. and 62.13 g (0.393 mol) of potassium permanganate are added in portions to this solution, and the mixture is stirred at room temperature for two days. After this time, the remaining potassium permanganate is filtered off, the solution is evaporated and purified by chromatography (eluent: heptane/dichloromethane, 5:1). The residue is recrystallised from n-heptane. The yield is 14 g (88%).

The following compounds are obtained analogously:

| Ex. | Starting material 1 | Product | Yield |
|---|---|---|---|
| 3a | | | 83% |
| 3b | | | 82% |
| 3c | | | 80% |
| 3d | | | 78% |

-continued
| Ex. | Starting material 1 | Product | Yield |
|---|---|---|---|
| 3e | 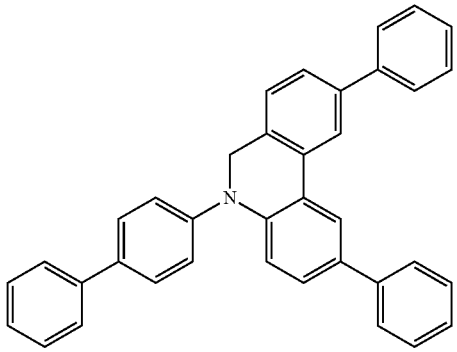 [SMILES: c1ccc(-c2ccc(N3Cc4ccc(-c5ccccc5)cc4-c4cc(-c5ccccc5)ccc43)cc2)cc1] | | 90% |
| 3f | 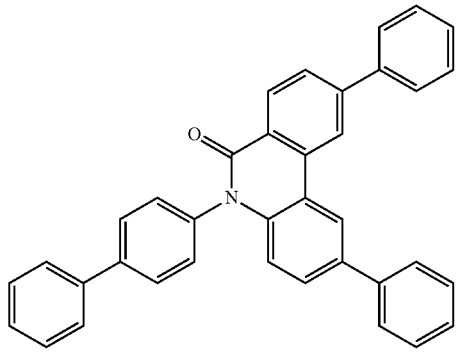 [SMILES: O=c1c2ccc(-c3ccccc3)cc2c2cc(-c3ccccc3)ccc2n1-c1ccc(-c2ccccc2)cc1] | | 69% |
| 3g | 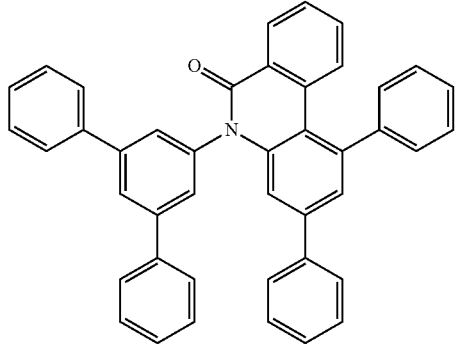 [SMILES: O=c1c2ccccc2c2c(-c3ccccc3)cc(-c3ccccc3)cc2n1-c1cc(-c2ccccc2)cc(-c2ccccc2)c1] | | 67% |

| Ex. | Starting material 1 | Product | Yield |
|---|---|---|---|
| 3h | 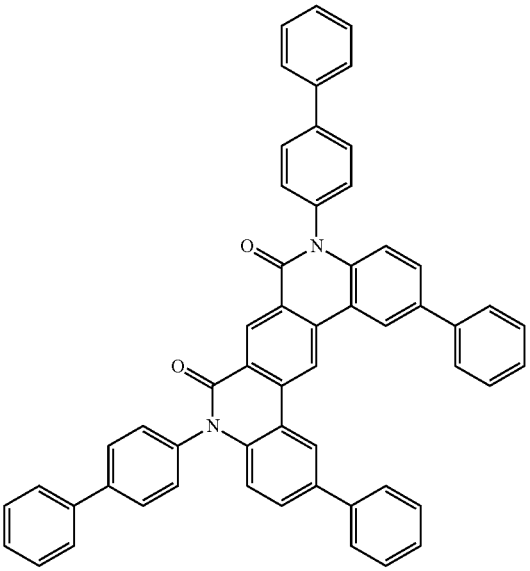 [SMILES: O=c1c2cc3c(=O)n(-c4ccc(-c5ccccc5)cc4)c4ccc(-c5ccccc5)cc4c3cc2c2cc(-c3ccccc3)ccc2n1-c1ccc(-c2ccccc2)cc1] | | 71% |
| 3i | 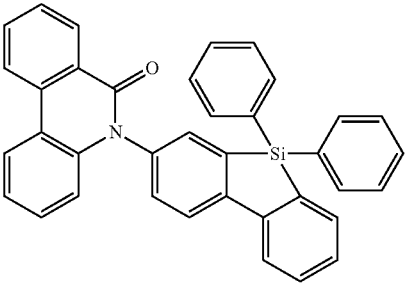 [SMILES: O=c1c2ccccc2c2ccccc2n1-c1ccc2c(c1)[Si](c1ccccc1)(c1ccccc1)c1ccccc1-2] | | 77% |
| 3j | 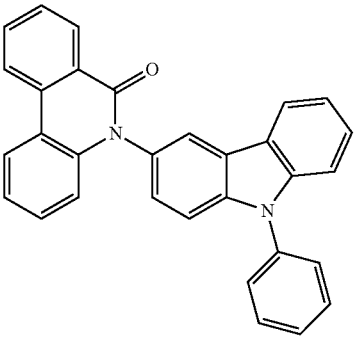 [SMILES: O=c1c2ccccc2c2ccccc2n1-c1ccc2c(c1)c1ccccc1n2-c1ccccc1] | | 72% |
| 3k | 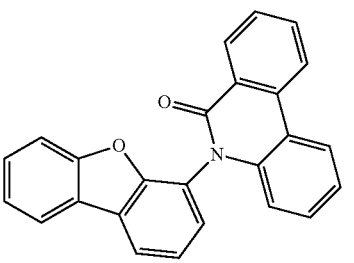 [SMILES: O=c1c2ccccc2c2ccccc2n1-c1cccc2c1oc1ccccc12] | | 78% |

| Ex. | Starting material 1 | Product | Yield |
|---|---|---|---|
| 31 | 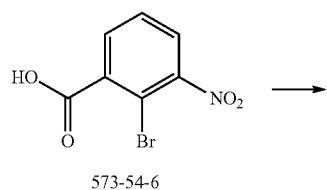 | 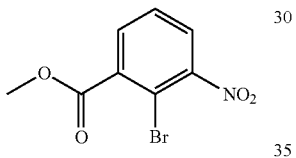 | 76% |

Example 4

Methyl 2-bromo-3-nitrobenzoate

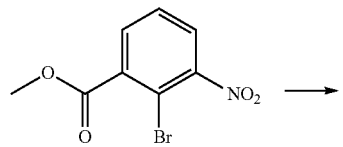

573-54-6

100 g (406 mmol) of 2-bromo-3-nitrobenzoic acid, 22 g (609 mmol) of conc. HCl and 1 l of methanol are heated under reflux for 24 h. After cooling, the precipitated solid is filtered off with suction, washed with water and ethanol and dried. The residue is recrystallised from ethanol. Yield: 94.6 g (363 mmol), 89.5% of theory.

Example 5

1,1'-Biphenyl-6,6'-dinitro-2,2'-dimethylcarboxylic acid ester

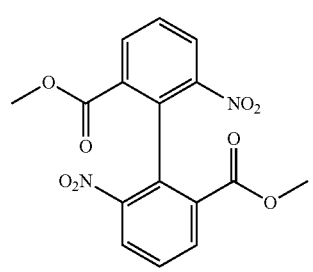

1 l of DMF is added to 84 g (323 mmol) of methyl 2-bromo-3-nitrobenzoate and 61.5 g (969 mmol) of copper powder, and the mixture is stirred at 120° C. for 1 h. The batch is cooled, and the copper is filtered off. The solution is diluted with water, extracted twice with ethyl acetate, the combined organic phases are dried over Na$_2$SO$_4$ and evaporated in a rotary evaporator. The residue is recrystallised from methanol. The yield is 47.4 g (131.5 mmol) 81.5% of theory.

Example 6

1,1'-Biphenyl-6,6'-dinitro-2,2'-carboxylic acid

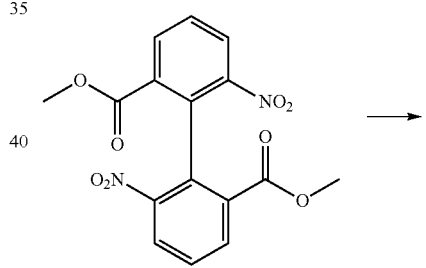

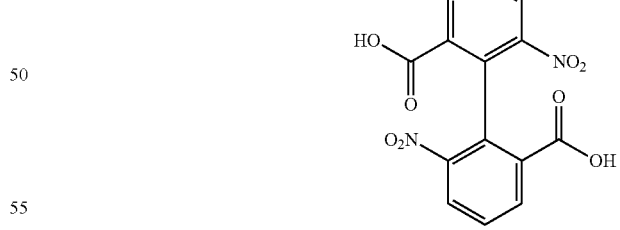

100 ml of water and 100 ml of ethanol are added to 42 g (116 5 mmol) of 1,1'-biphenyl-6,6'-dinitro-2,2'-dimethylcarboxylic acid ester and 21 g (524 mmol) of NaOH, and the mixture is stirred at 90° C. for 2 h. The batch is cooled, rendered acidic using 5M HCl and stirred for 30 min. The precipitated solid filtered off with suction. The residue is recrystallised from heptane. Yield: 33.6 g (332.2 mmol), 86% of theory.

119

Example 7

Pyrido[2,3,4,5-lmn]phenanthridine-5,10-dione

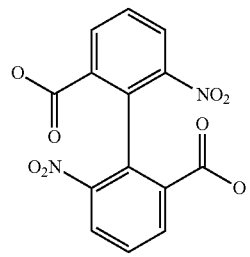

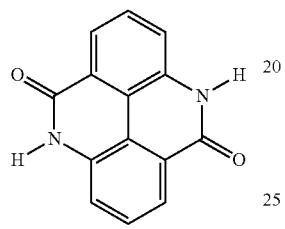

40 g (129 mmol) of 11,1'-biphenyl-6,6'-dinitro-2,2'-carboxylic acid and 50 g (931 mmol) of iron powder are stirred at 80° C. with 500 ml of acetic acid for 12 h. The batch is cooled, and the precipitated solid is filtered off with suction. The residue is recrystallised from DMF. Yield: 19 g (84.3 mmol), 70% of theory.

120

Example 8

4,9 Dihenyl-4,9-dihydropyrido[2,3,4,5-lmn]phenanthridine-5,10-dione

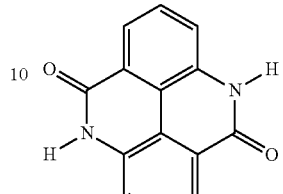

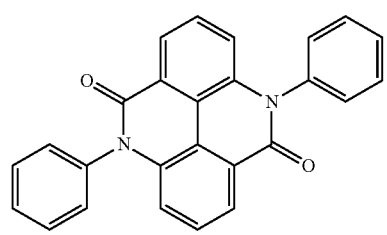

23 g (100 mmol) of pyrido[2,3,4,5-lmn]phenanthridine-5,10-dione and 61.2 g (300 mmol) of 4-iodobenzene and 2.3 g (20 mmol) of L-proline are stirred at 150° C. in 100 ml for 30 h The solution is diluted with water and extracted twice with ethyl acetate, the combined organic phases are dried over $Na_2SO_4$ and evaporated in a rotary evaporator. The residue is purified by chromatography (EtOAc/hexane: 2/3). The yield is 20 g (52 mmol), 55% of theory.

The following compounds are obtained analogously:

| Ex. | Starting material 1 | Starting material 1 | Product | Yield |
|---|---|---|---|---|
| 8a | | | | 57% |
| 8b | | | | 56% |

Example 9

6-[1,1';3',1"]-Terphenyl-5'-yl-6H-benzo[c][2,6]naphthyridin-5-one

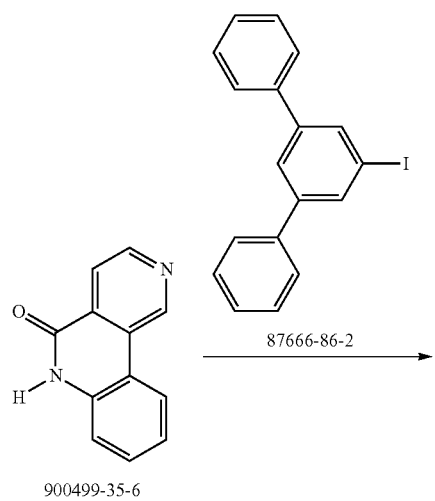

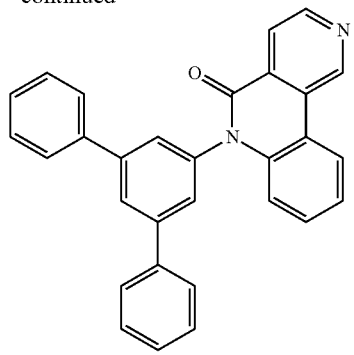

19.6 g (100 mmol) of benzo[c]-2,6-napthyridinone, 106 g (300 mmol) of 5'-iodo-[1,1';3',1"]terphenyl and 2.3 g (20 mmol) of L-proline are stirred at 150° C. in 100 ml for 30 h The solution is diluted with water, extracted twice with ethyl acetate, the combined organic phases are dried over Na$_2$SO$_4$ and evaporated in a rotary evaporator. The residue is purified by chromatography (EtOAc/hexane: 2/3). The yield is 25 g (59 mmol) 60% of theory.

The following compounds are obtained analogously:

| Ex. | Starting material 1 | Starting material 1 | Product | Yield |
|---|---|---|---|---|
| 9a | 1017606-34-6 | 87666-86-2 | | 56% |
| 9b | 164261-68-1 | | | 54 |

-continued
| Ex. | Starting material 1 | Starting material 1 | Product | Yield |
|---|---|---|---|---|
| 9c | 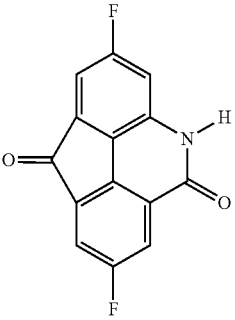<br>391248-47-8 | 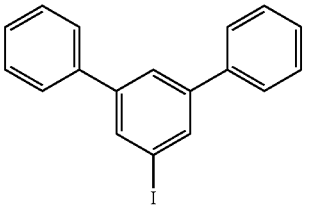 [SMILES: Ic1cc(-c2ccccc2)cc(-c2ccccc2)c1] | 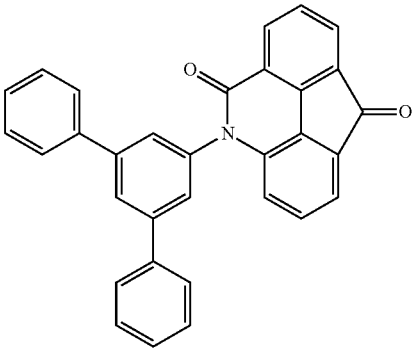 [SMILES: O=c1c2cccc3c(=O)n(-c4cc(-c5ccccc5)cc(-c5ccccc5)c4)c4cccc1c4c23] | 58% |
| 9d | 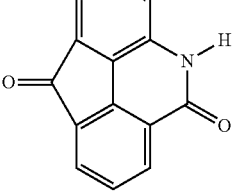<br>61479-80-9 | 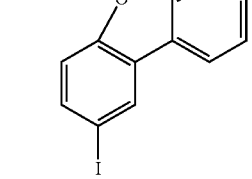 | 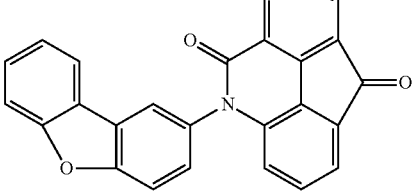 | 53% |
| 9e | 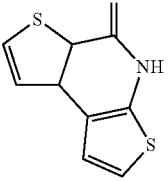<br>40197-38-4 | 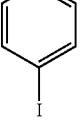 | 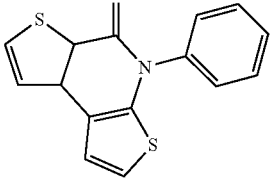 | 59% |
| 9f | 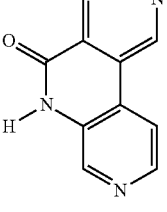<br>1186039-92-8 | 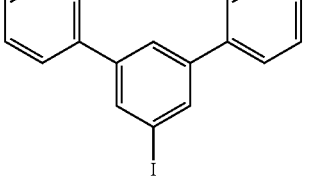 | 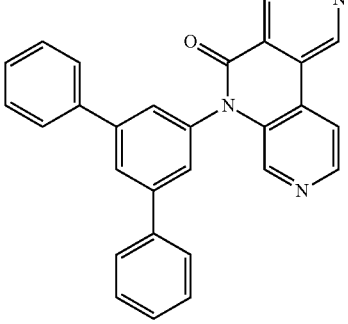 | 62% |
| 9g | 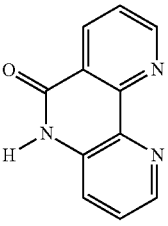<br>851066-63-2 | 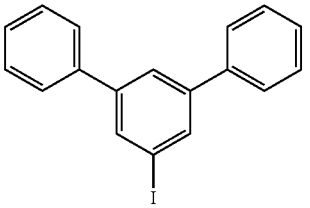 [SMILES: Ic1cc(-c2ccccc2)cc(-c2ccccc2)c1] | 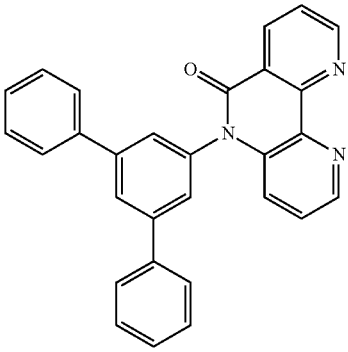 [SMILES: O=c1c2cccnc2c2ncccc2n1-c1cc(-c2ccccc2)cc(-c2ccccc2)c1] | 63% |

Example 10

2-(2-Bromobenzyl)diphenylamine

Example 11

5-Phenyl-5,6-dihydrophenanthridine

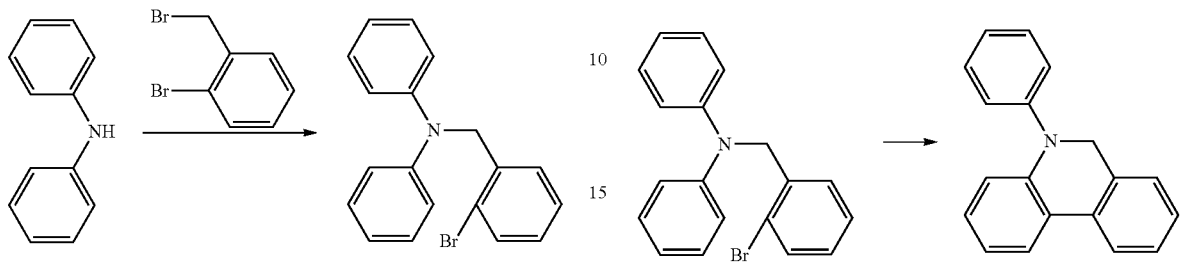

12 g (0.307 mol) of NaH (60% in mineral oil) are dissolved in 600 ml of dimethylformamide under protective atmosphere. 40 g (0.263 mol) of N,N-diphenylamine are dissolved in 600 ml of DMF and added dropwise to the reaction mixture. After 1 h at room temperature, a solution of 98.7 (395 mmol) of 2-bromobenzyl bromide in 500 ml of DMF is added dropwise. The reaction mixture is stirred at room temperature for 1 h, then poured onto ice and extracted three times with dichloromethane. The combined organic phases are dried over $Na_2SO_4$ and evaporated. The residue is extracted with hot toluene and recrystallised from toluene/n-heptane. The yield is 71 g (89%).

The following compounds are obtained analogously:

10 g (0.295 mol) of (2-bromobenzyl)diphenylamine are dissolved in 500 ml of dimethylformamide under protective atmosphere. 3.4 g (0.075 mol) of benzyltrimethylammonium bromide and 6.1 g (0.443 mol) of potassium carbonate are added to this solution. 0.99 g (0.004 mol) of $Pd(OAC)_2$ is subsequently added under protective gas, and the mixture is stirred at 120° C. for 9 h. After this time, the reaction mixture is cooled to room temperature and extracted with dichloromethane. The combined organic phases are dried over $Na_2SO_4$ and evaporated. The residue is recrystallised from n-heptane. The yield is 6 g (80%).

The following compounds are obtained analogously:

| Ex. | Starting material 1 | Starting material 2 | Product | Yield |
|---|---|---|---|---|
| 10a | 1205-39-6 | 3433-80-5 | | 85% |
| 10b | | 172976-02-2 | | 91% |

| Ex. | Starting material 1 | Product | Yield |
|---|---|---|---|
| 11a | | | 79% |
| 11b | | | 80% |

Example 12

5-Phenyl-5H-phenanthridin-6-one

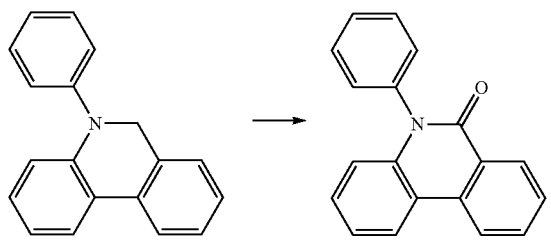 [SMILES: c1ccc(N2Cc3ccccc3-c3ccccc32)cc1 ; O=c1c2ccccc2c2ccccc2n1-c1ccccc1]

10 g (0.039 mol) of 5-phenyl-5,6-dihydrophenanthridine are dissolved in 300 ml of dichloromethane. 62.13 g (0.393 mol) of potassium permangenate are added in portions to this solution, and the mixture is stirred at room temperature for two days. After this time, the remaining potassium permanganate is filtered off, the solution is evaporated and purified by chromatography (eluent: heptane/dichloromethane, 5:1). The residue is recrystallised from n-heptane. The yield is 8.2 g (80%).

The following compounds are obtained analogously:

| Ex. | Starting material 1 | Product | Yield |
|---|---|---|---|
| 12a | | | 83% |
| 12b | | | 82% |

Example 13

5-(4-Bromophenyl)-5H-phenanthridin-6-one

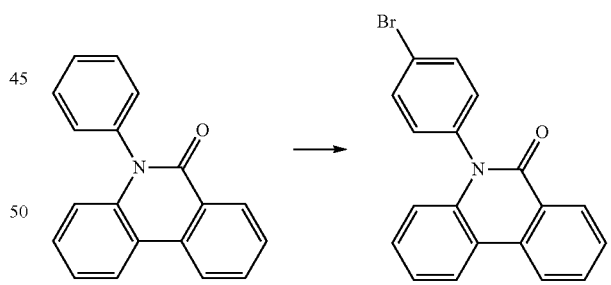

6.0 g (22.2 mmol) of 5-phenyl-5H-phenanthridin-6-one are initially introduced in 150 ml of $CH_2Cl_2$. A solution of 4 g (22.5 mmol) of NBS in 100 ml of acetonitrile is subsequently added dropwise at −15° C. with exclusion of light, the mixture is allowed to come to room temperature and is stirred at this temperature for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane and filtered off with suction. Yield: 7.4 g (21 mmol), 80% of theory, purity according to $^1$H-NMR about 96%.

The following compounds are obtained analogously:

| Ex. | Starting material 1 | Product 1 | Yield |
|---|---|---|---|
| 13a | 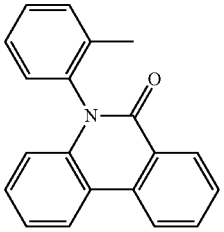 [SMILES: Cc1ccccc1-n1c(=O)c2ccccc2c2ccccc21] | 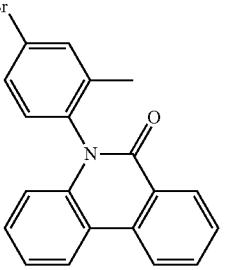 | 65% |
| 13b | 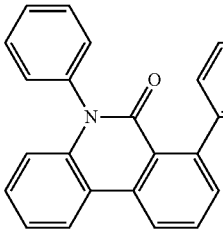 | 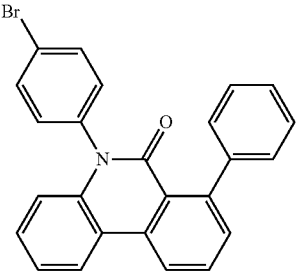 [SMILES: O=c1c2c(-c3ccccc3)cccc2c2ccccc2n1-c1ccc(Br)cc1] | 83% |
The following compounds are obtained analogously with 2 equivalents of NBS in chloroform as solvent:
| Ex. | Starting material 1 | Product 1 | Yield |
|---|---|---|---|
| 13c | 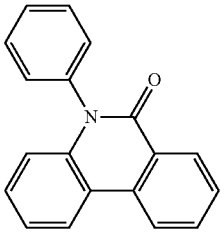 [SMILES: O=c1c2ccccc2c2ccccc2n1-c1ccccc1] | 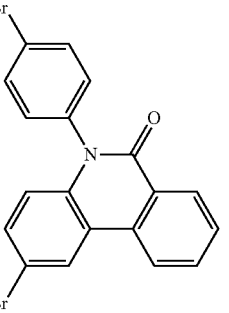 | 87 |
| 13d | 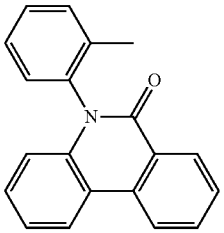 [SMILES: Cc1ccccc1-n1c(=O)c2ccccc2c2ccccc21] | 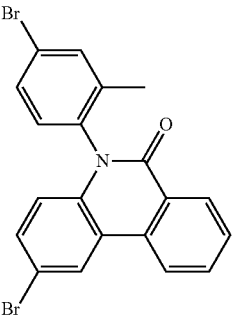 [SMILES: Cc1cc(Br)ccc1-n1c(=O)c2ccccc2c2cc(Br)ccc21] | 82% |

Example 14

5-(4-Dibenzofuran-4-ylphenyl)-5H-phenanthridin-6-one

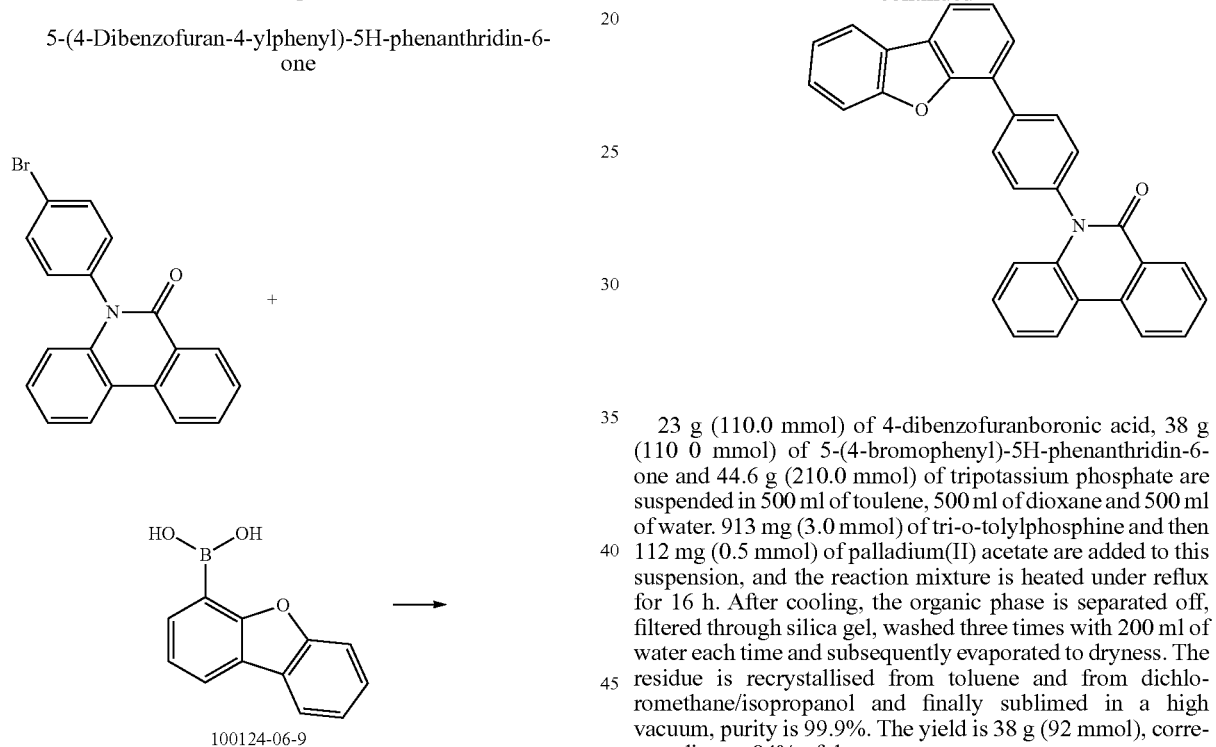

23 g (110.0 mmol) of 4-dibenzofuranboronic acid, 38 g (110 0 mmol) of 5-(4-bromophenyl)-5H-phenanthridin-6-one and 44.6 g (210.0 mmol) of tripotassium phosphate are suspended in 500 ml of toulene, 500 ml of dioxane and 500 ml of water. 913 mg (3.0 mmol) of tri-o-tolylphosphine and then 112 mg (0.5 mmol) of palladium(II) acetate are added to this suspension, and the reaction mixture is heated under reflux for 16 h. After cooling, the organic phase is separated off, filtered through silica gel, washed three times with 200 ml of water each time and subsequently evaporated to dryness. The residue is recrystallised from toluene and from dichloromethane/isopropanol and finally sublimed in a high vacuum, purity is 99.9%. The yield is 38 g (92 mmol), corresponding to 84% of theory.

The following compounds are obtained analogously:

-continued

| Ex. | Starting material 1 | Starting material 2 | Product | Yield |
|---|---|---|---|---|
| 14b | | 854952-58-2 | | 81% |
| 14c | | 943836-24-6 | | 84% |
| 14d | | 128388-54-5 | | 88% |

| Ex. | Starting material 1 | Starting material 2 | Product | Yield |
|---|---|---|---|---|
| 14e | 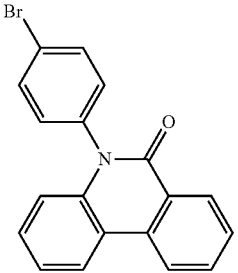 [SMILES: O=c1c2ccccc2c2ccccc2n1-c1ccc(Br)cc1] | 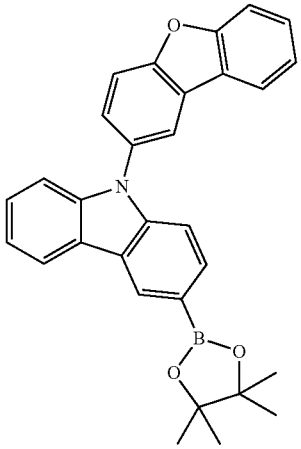
1338488-91-7 | 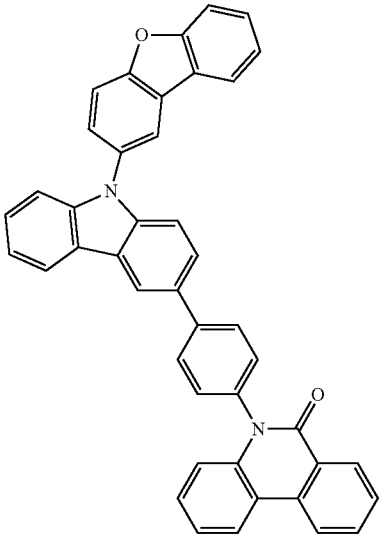 [SMILES: O=c1c2ccccc2c2ccccc2n1-c1ccc(-c2ccc3c(c2)c2ccccc2n3-c2ccc3oc4ccccc4c3c2)cc1] | 67% |
| 14f | 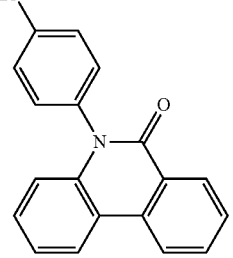 | 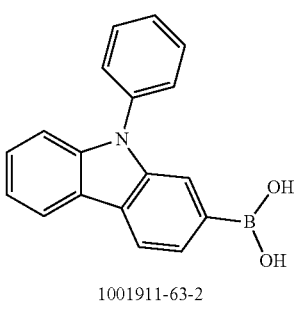 [SMILES: OB(O)c1ccc2c3ccccc3n(-c3ccccc3)c2c1]
1001911-63-2 | 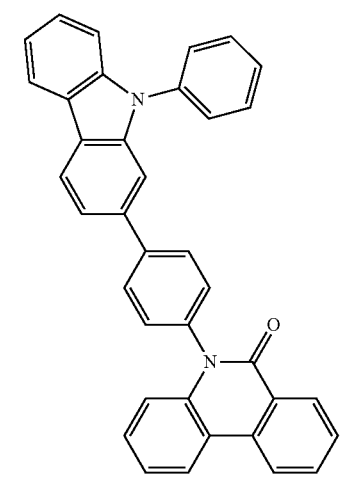 [SMILES: O=c1c2ccccc2c2ccccc2n1-c1ccc(-c2ccc3c4ccccc4n(-c4ccccc4)c3c2)cc1] | 75% |

-continued

| Ex. | Starting material 1 | Starting material 2 | Product | Yield |
|---|---|---|---|---|
| 14g | | 854952-60-6 | | 76% |
| 14h | | 1313018-07-3 | | 83% |

The following compounds are obtained analogously with 0.5 equivalents of the lactam:

| Ex. | Starting material 1 | Starting material 2 | Product | Yield |
|---|---|---|---|---|
| 14i | | | | 93% |

-continued

| Ex. | Starting material 1 | Starting material 2 | Product | Yield |
|---|---|---|---|---|
| 14j | | 854952-58-2 | | 84% |
| 14k | | 943836-24-6 | | 84% |

-continued

| Ex. | Starting material 1 | Starting material 2 | Product | Yield |
|---|---|---|---|---|
| 14l | | 128388-54-5 | | 88% |
| 14m | | 1338488-91-7 | | 75% |

-continued
| Ex. | Starting material 1 | Starting material 2 | Product | Yield |
|---|---|---|---|---|
| 14n | 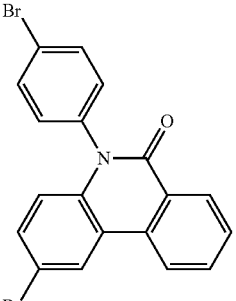 | 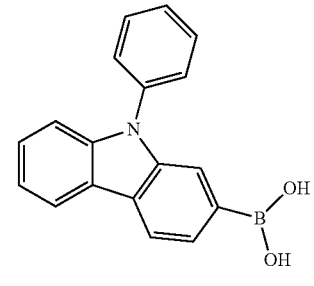
1001911-63-2 | 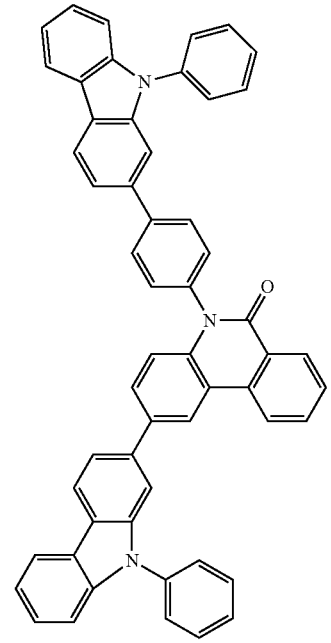 [SMILES: O=c1c2ccccc2c2cc(-c3ccc4c5ccccc5n(-c5ccccc5)c4c3)ccc2n1-c1ccc(-c2ccc3c4ccccc4n(-c4ccccc4)c3c2)cc1] | 72% |
| 14o | 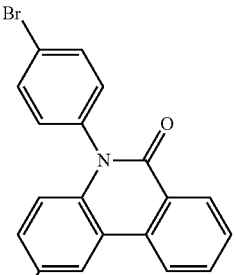 | 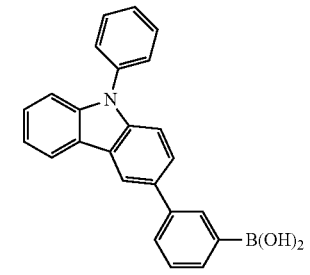
854952-60-6 | 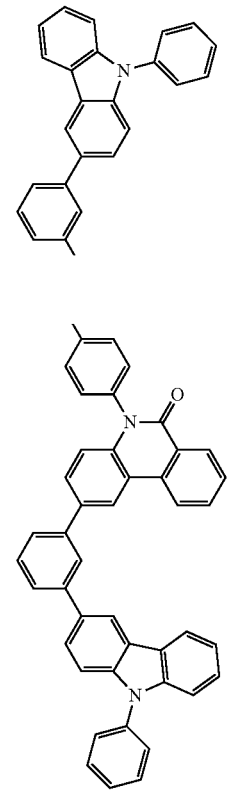 | 70% |

| Ex. | Starting material 1 | Starting material 2 | Product | Yield |
|---|---|---|---|---|
| 14p | 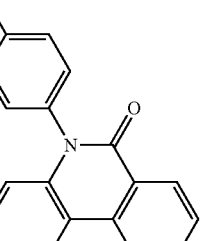 | 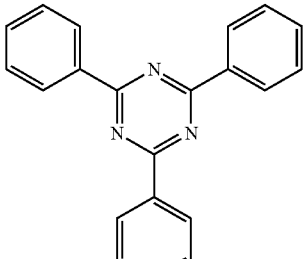 1313018-07-3 | 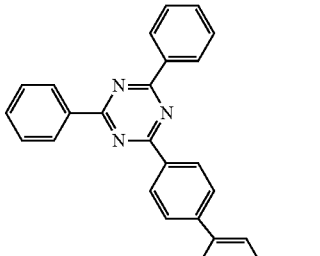 | 82% |

Example 15

3,6-Dibromo-9,9-dimethyl-9,10-dihydroacridine

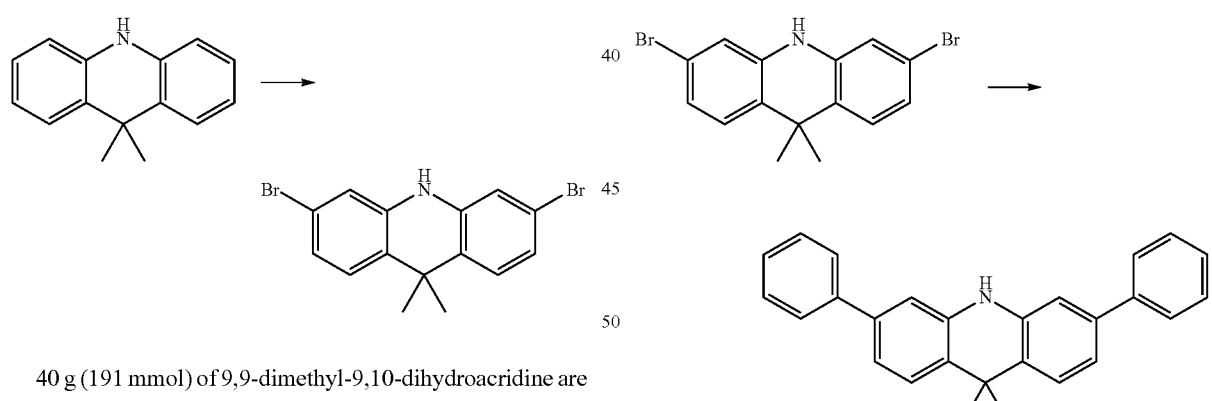

40 g (191 mmol) of 9,9-dimethyl-9,10-dihydroacridine are initially introduced in 1000 ml of CH$_2$Cl$_2$. A solution of 68 g (382 mmol) of NBS in 600 ml of CH$_2$Cl$_2$ is subsequently added dropwise at −25° C. with exclusion of light, the mixture is allowed to come to room temperature and is stirred at this temperature for a further 4 h. 150 ml of water are subsequently added to the mixture, which is then extracted with CH$_2$Cl$_2$. The organic phase is dried over MgSO$_4$, and the solvents are removed in vacuo. The product is washed by stirring with hot hexane and filtered off with suction. Yield: 61.4 g (16 mmol), 70% of theory, purity according to $^1$H-NMR about 98%.

Example 16

9,9-Dimethyl-3,6-diphenyl-9,10-dihydroacridine 1.7 g (5.7 mmol) of tri-o-tolylphosphine and then 643 mg (2.8 mmol) of palladium(II) acetate are added to a degassed suspension of 52 g (143 mmol) of 3,6-dibromo-9,9-dimethyl-9,10-dihydroacridine, 38.4 g (315 mmol) of phenylboronic acid and 60 g (286 mmol) of potassium phosphate hydrate in a mixture of 420 ml of dioxane, 840 ml of toluene and 420 ml of water with vigorous stirring. After heating under reflux for 5 h, the mixture is allowed to cool. The precipitate is filtered off with suction, washed three times with 10 ml of ethanol/ water (1:1, v:v) and three times with 5 ml of ethanol, subsequently dried in vacuo and recrystallised from dioxane. Yield: 41 g (113 mmol), 81% of theory, purity according to ¹H-NMR about 99.9%.

Example 17

10-(2-Bromobenzyl)-9,9-dimethyl-9,10-dihydroacridine

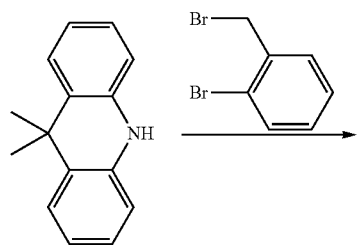

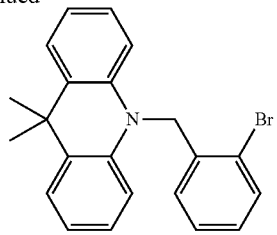

9.7 g (0.243 mol) of NaH, 60% in mineral oil, are dissolved in 500 ml of dimethylformamide under protective atmosphere. 22.1 g (0.106 mol) of 9,9-dimethyl-9,10-dihydroacridine are dissolved in 500 ml of DMF and added dropwise to the reaction mixture. After 1 h at room temperature, a solution of 60.6 (242 mmol) of 2-bromobenzyl bromide in 500 ml of DMF is added dropwise. The reaction mixture is stirred at room temperature for 1 h, then poured onto ice and extracted three times with dichloromethane. The combined organic phases are dried over $Na_2SO_4$ and evaporated. The residue is extracted with hot toluene and recrystallised from toluene/n-heptane. The yield is 37 g (94%).

The following compounds are obtained analogously:

| Ex. | Starting material 1 | Starting material 2 | Product | Yield |
|---|---|---|---|---|
| 17a | | | | 88% |

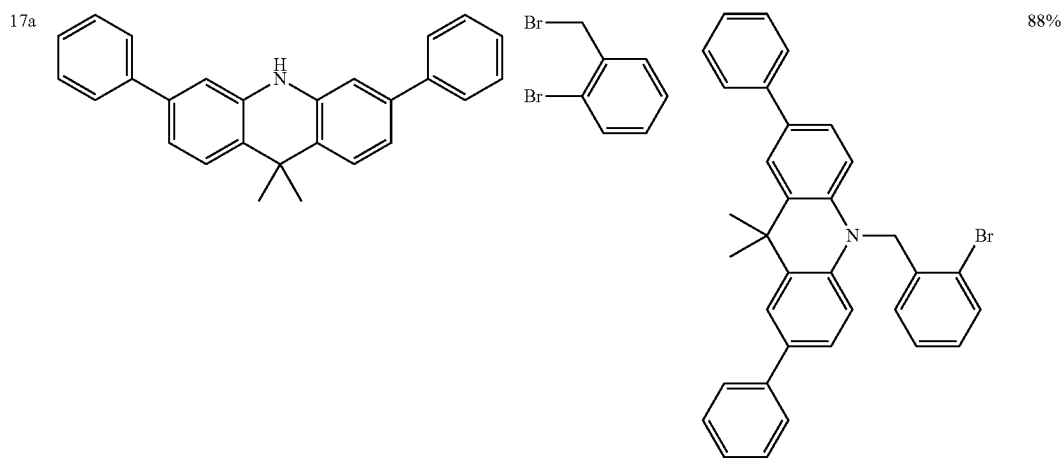

| 17b | | | | 80% |

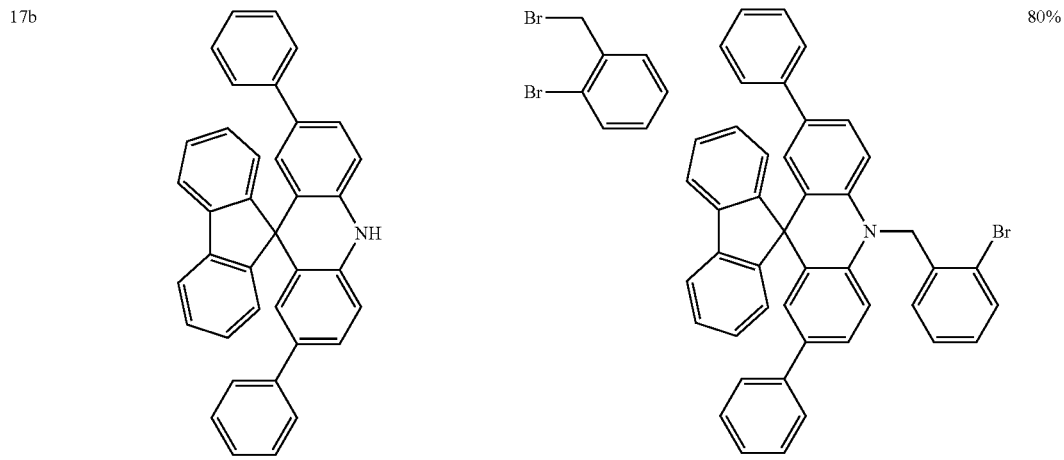

Example 18

5-Biphenyl-4-yl-2-phenyl-5,6-dihydrophenanthridine

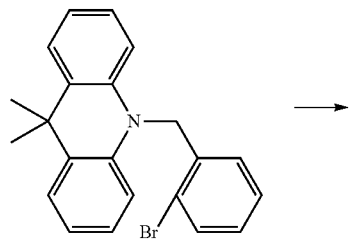

→

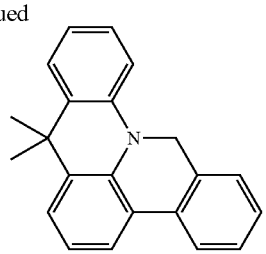

59.7 g (0.158 mol) of 10-(2-bromobenzyl)-9,9-dimethyl-9,10-dihydro-acridine are dissolved in 500 ml of dimethylformamide under protective atmosphere. 17.3 g (0.075 mol) of benzyltrimethylammonium bromide and 31.28 g (0.226 mol) of potassium carbonate are added to this solution. 5.08 g (0.022 mol) of Pd(OAc)$_2$ is subsequently added under protective gas, and the mixture is stirred at 120° C. for 9 h. After this time, the reaction mixture is cooled to room temperature and extracted with dichloromethane. The combined organic phases are dried over Na$_2$SO$_4$ and evaporated. The residue is recrystallised from n-heptane. The yield is 39.5 g (86%).

The following compounds are obtained analogously:

| Ex. | Starting material 1 | Product | Yield |
|---|---|---|---|
| 18a | (structure) | (structure) | 82% |
| 18b | (structure) | (structure) | 78% |

Example 19

8,8-Dimethyl-8H-12b-azadibenzo[a,de]anthracen-13-one

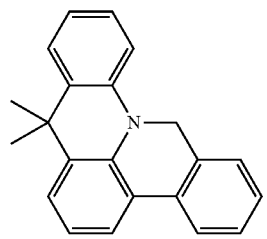

→

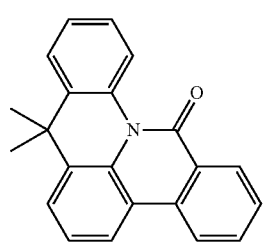

11.7 g (0.039 mol) of 5-biphenyl-4-yl-2-phenyl-5,6-dihydrophenanthridine are dissolved in 300 ml of dichloromethane. 17.3 g (0.075 mol) of benzyl-trimethylammonium bromide and 62.13 g (0.393 mol) of potassium permanganate are added in portions to this solution, and the mixture is stirred at room temperature for two days. After this time, the remaining potassium permanganate is filtered off, the solution is evaporated and purified by chromatography (eluent: heptane/dichloromethane, 5:1). The residue is recrystallised from n-heptane. The yield is 9.8 g (80%).

The following compound is obtained analogously:

Example 20

5-[3-(4,6-Diphenyl-1,3,5-triazin-2-yl)phenyl]-5H-phenanthridin-6-one

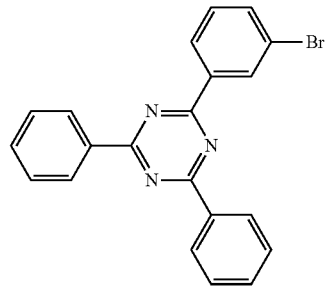

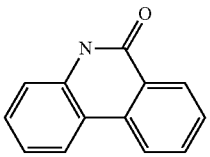

1015-89-0

864377-31-1 →

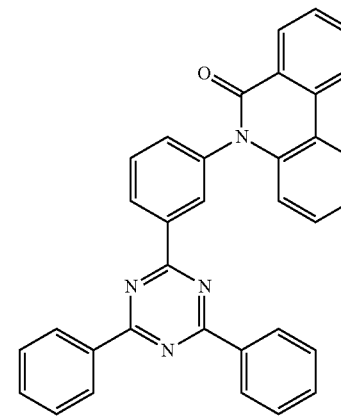

20 g (102 4 mmol) of 5H-phenanthridin-6-one, 43 g (112 mmol) of 2-(3-bromophenyl)-4,6-diphenyl-1,3,5-triazine, 2.3 g (10 2 mmol) of 1,3-bis[2-pyridyl]-1,3-propanedione,

| Ex. | Starting material 1 | Product | Yield |
|---|---|---|---|
| 19a | | | 89% |

28.3 g (204 mmol) of potassium carbonate and 1.9 g (10.2) of copper iodide are stirred under reflux in 1000 ml of DMF for 90 h. The solution is diluted with water and extracted twice with ethyl acetate, the combined organic phases are dried over Na₂SO₄, evaporated in a rotary evaporator and purified by chromatography (EtOAc/hexane: 2/3). The residue is recrystallised from toluene and from dichloromethane and finally sublimed in a high vacuum, purity is 99.9%. The yield is 31 g (62 mmol), corresponding to 61% of theory.

The following compounds are obtained analogously:

| Ex. | Starting material 1 | Starting material 2 | Product | Yield |
|---|---|---|---|---|
| 20a | 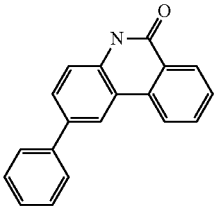 157848-49-2 | 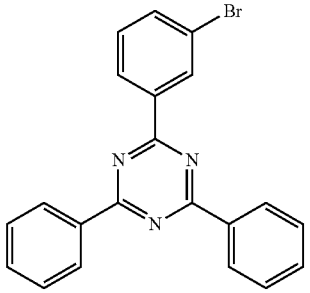 [SMILES: Brc1cccc(-c2nc(-c3ccccc3)nc(-c3ccccc3)n2)c1] | 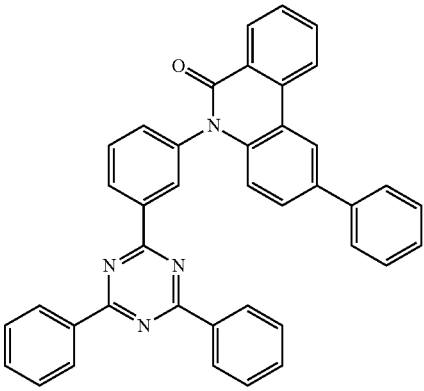 [SMILES: O=c1c2ccccc2c2cc(-c3ccccc3)ccc2n1-c1cccc(-c2nc(-c3ccccc3)nc(-c3ccccc3)n2)c1] | 59% |
| 20b | 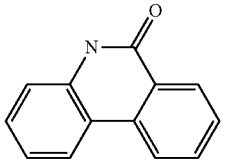 [SMILES: O=c1[nH]c2ccccc2c2ccccc12] | 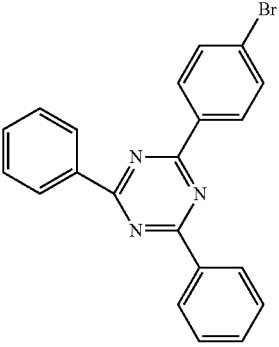 23449-08-3 | 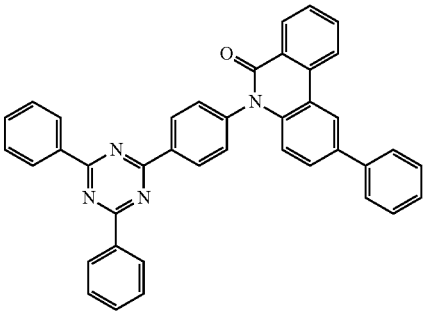 [SMILES: O=c1c2ccccc2c2cc(-c3ccccc3)ccc2n1-c1ccc(-c2nc(-c3ccccc3)nc(-c3ccccc3)n2)cc1] | 57% |
| 20c | 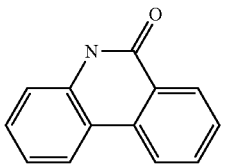 [SMILES: O=c1[nH]c2ccccc2c2ccccc12] | 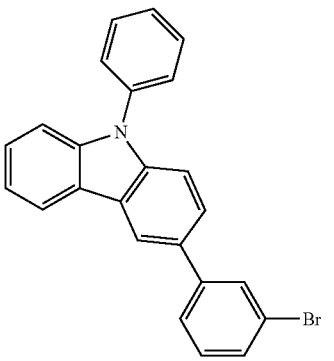 854952-59-3 | 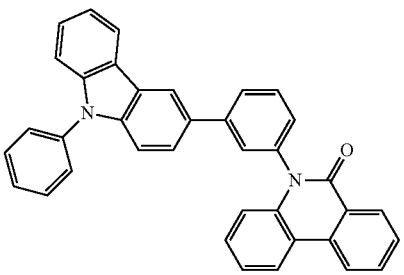 [SMILES: O=c1c2ccccc2c2ccccc2n1-c1cccc(-c2ccc3c(c2)c2ccccc2n3-c2ccccc2)c1] | 54% |

-continued

| Ex. | Starting material 1 | Starting material 2 | Product | Yield |
|---|---|---|---|---|
| 20d | 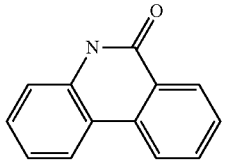 | 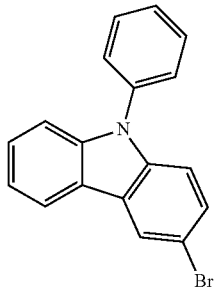 1153-85-1 | 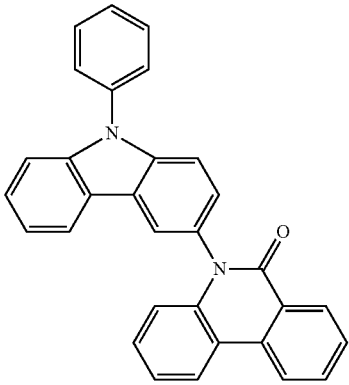 [SMILES: O=c1c2ccccc2c2ccccc2n1-c1ccc2c(c1)c1ccccc1n2-c1ccccc1] | 58% |
| 20e | 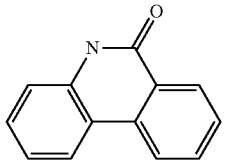 [SMILES: O=c1[nH]c2ccccc2c2ccccc12] | 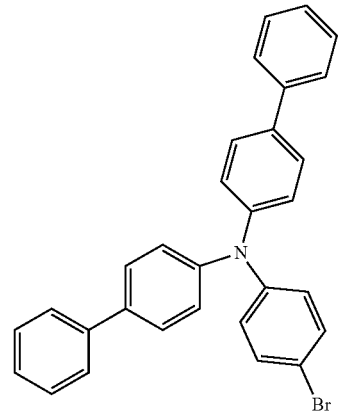 1371655-72-9 | 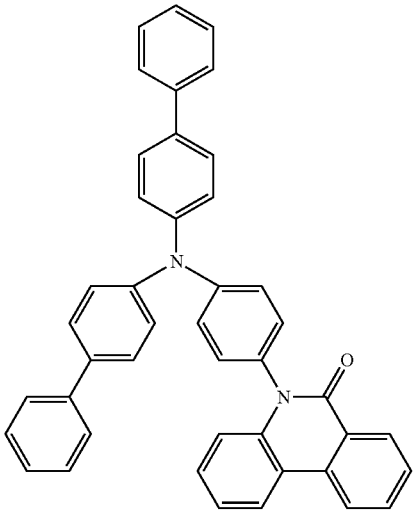 [SMILES: O=c1c2ccccc2c2ccccc2n1-c1ccc(N(c2ccc(-c3ccccc3)cc2)c2ccc(-c3ccccc3)cc2)cc1] | |

Production of OLEDs

OLEDs according to the invention and OLEDs in accordance with the prior art are produced by a general process in accordance with WO 2004/058911, which is adapted to the circumstances described here (layer-thickness variation, materials).

The data of various OLEDs are presented in the following Examples V1 to E29 (see Tables 1 and 2). Glass plates coated with structured ITO (indium tin oxide) in a thickness of 50 nm are coated with 20 nm of PEDOT:PSS (poly(3,4-ethylenedioxythiophene)poly(styrenesulfonate), purchased as CLEVIOS™ P VP AI 4083 from Heraeus Precious Metals GmbH Germany, applied by spin coating from aqueous solution) for improved processing. These coated glass plates form the substrates to which the OLEDs are applied. The OLEDs have in principle the following layer structure: substrate/optional hole-injection layer (HIL)/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. A designation such as "3f" relates to the compound from Example 3f, etc. The other materials required for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as 9 h:VCbz1:TEG1 (60%:30%:10%) here means that material 9 h is present in the layer in a proportion by volume of 60%, VCbz1 is present in the layer in a proportion of 30% and TEG1 is present in the layer in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The term U1000 in Table 2 denotes the voltage required for a luminous density of 1000 cd/m$^2$. CE1000 and PE1000 denote the current and power efficiency respectively which are achieved at 1000 cd/m$^2$. Finally, EQE1000 denotes the external quantum efficiency at an operating luminous density of 1000 cd/m$^2$.

The data of the various OLEDs are summarised in Table 2. Examples V1 and V2 are comparative examples in accordance with the prior art, Examples E1-E19 show data of OLEDs comprising materials according to the invention.

Some of the examples are explained in greater detail below in order to illustrate the advantages of the compounds according to the invention. However, it should be pointed out that this only represents a selection of the data shown in Table 2.

Use of Compounds According to the Invention in the Electron-Transport Layer

If compound 9 g is employed in an electron-transport layer, a low operating voltage of 4.3 V and a very good quantum efficiency of somewhat greater than 8% is obtained, these values are significantly worse on use of compound LaDi1 in accordance with the prior art (Examples V2 and E5).

Furthermore, very good lifetimes are obtained with materials according to the invention: for the OLED in accordance with Example E4, for example, the luminous density drops to 70% of its initial value within 210 h on operation at 60 mA/cm$^2$.

Use of Compounds According to the Invention as Matrix Materials in Phosphorescent OLEDs On use of materials according to the invention as single matrix material in combination with the green dopant TEG1, very low operating voltages of 3.3 V and very good external quantum efficiencies up to 16.4% are obtained (Examples E10 and E11).

Very good performance data are also obtained with materials according to the invention in a mixed-matrix system. In combination with material VCbz1, for example, an external quantum efficiency of greater than 17% is obtained and a very low operating voltage of 3.3 V is required (Example E13).

If a triazine- or pyrimidine-containing compound is selected as second component in a mixed-matrix system, very good performance data are likewise obtained, for example an external quantum efficiency of greater than 16% in the combination IC1 with 19a (Example E23).

Furthermore, very good lifetimes are obtained: for the OLED in accordance with Example E1, for example, the luminous density drops to 70% of its initial value within 170 h on operation at 20 mA/cm$^2$. For the OLED in accordance with Example E10, a lifetime of 190 h is obtained under the same conditions. With material LaDi1 in accordance with the prior art, by contrast, a lifetime of only 130 h is obtained under the same conditions (OLED in accordance with Example V1). Even better lifetimes can be achieved in mixed-matrix systems, for example a drop to 70% within 330 h is obtained for an OLED in accordance with Example E16 on operation at 20 mA/cm$^2$. A drop to 80% of the initial luminous density in 305 h is obtained on operation of an OLED in accordance with Example E23 at 20 mA/cm$^2$, even only after 340 h for Example E22.

TABLE 1

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| V1 | — | SpA1 70 nm | HATCN 5 nm | SpMA1 90 nm | LaDi1:TEG1 (90%:10%) 30 nm | IC1 10 nm | ST1:LiQ (50%:50%) 30 nm | — |
| V2 | HATCN 5 nm | SpA1 140 nm | HATCN 5 nm | SpMA1 20 nm | M1:D1 (95%:5%) 20 nm | — | LaDi1 30 nm | LiQ 3 nm |
| E1 | — | SpA1 70 nm | HATCN 5 nm | SpMA1 90 nm | 3:TEG1 (90%:10%) 30 nm | IC1 10 nm | ST1:LiQ (50%:50%) 30 nm | — |
| E2 | — | SpA1 70 nm | HATCN 5 nm | SpMA1 90 nm | 3e:TEG1 (90%:10%) 30 nm | IC1 10 nm | ST1:LiQ (50%:50%) 30 nm | — |
| E3 | — | SpA1 70 nm | HATCN 5 nm | SpMA1 90 nm | 3f:TEG1 (90%:10%) 30 nm | IC1 10 nm | ST1:LiQ (50%:50%) 30 nm | — |
| E4 | HATCN 5 nm | SpA1 140 nm | HATCN 5 nm | SpMA1 20 nm | M1:D1 (95%:5%) 20 nm | — | 9f:LiQ (50%:50%) 30 nm | — |
| E5 | HATCN 5 nm | SpA1 140 nm | HATCN 5 nm | SpMA1 20 nm | M1:D1 (95%:5%) 20 nm | — | 9g 30 nm | LiQ 3 nm |
| E6 | HATCN 5 nm | SpA1 140 nm | HATCN 5 nm | SpMA1 20 nm | M1:D1 (95%:5%) 20 nm | — | 3h 30 nm | LiQ 3 nm |
| E7 | — | SpA1 70 nm | HATCN 5 nm | SpMA1 90 nm | 3h:TEG1 (90%:10%) 30 nm | IC1 10 nm | ST1:LiQ (50%:50%) 30 nm | — |
| E8 | — | SpA1 70 nm | HATCN 5 nm | SpMA1 90 nm | 3j:IC1:TEG1 (60%:30%:10%) 30 nm | IC1 10 nm | ST1:LiQ (50%:50%) 30 nm | — |
| E9 | — | SpA1 70 nm | HATCN 5 nm | SpMA1 90 nm | 3k:TEG1 (90%:10%) 30 nm | IC1 10 nm | ST1:LiQ (50%:50%) 30 nm | — |
| E10 | — | SpA1 70 nm | HATCN 5 nm | SpMA1 90 nm | 8a:TEG1 (90%:10%) 30 nm | IC1 10 nm | ST1:LiQ (50%:50%) 30 nm | — |
| E11 | — | SpA1 70 nm | HATCN 5 nm | SpMA1 90 nm | 8:TEG1 (90%:10%) 30 nm | IC1 10 nm | ST1:LiQ (50%:50%) 30 nm | — |

TABLE 1-continued

Structure of the OLEDs

| Ex. | HIL Thickness | HTL Thickness | IL Thickness | EBL Thickness | EML Thickness | HBL Thickness | ETL Thickness | EIL Thickness |
|---|---|---|---|---|---|---|---|---|
| E12 | — | SpA1 70 nm | HATCN 5 nm | SpMA1 90 nm | 8b:TEG1 (90%:10%) 30 nm | IC1 10 nm | ST1:LiQ (50%:50%) 30 nm | — |
| E13 | — | SpA1 70 nm | HATCN 5 nm | SpMA1 90 nm | 9g:VCbz1:TEG1 (60%:30%:10%) 30 nm | IC1 10 nm | ST1:LiQ (50%:50%) 30 nm | — |
| E14 | — | SpA1 90 nm | HATCN 5 nm | SpMA1 130 nm | 9c:TER1 (92%:8%) 40 nm | — | ST1:LiQ (50%:50%) 40 nm | — |
| E15 | — | SpA1 90 nm | HATCN 5 nm | SpMA1 130 nm | 9d:TER1 (92%:8%) 40 nm | — | ST1:LiQ (50%:50%) 40 nm | — |
| E16 | — | SpA1 70 nm | HATCN 5 nm | SpMA1 90 nm | 9b:IC1:TEG1 (60%:30%) 30 nm | IC1 10 nm | ST1:LiQ (50%:50%) 30 nm | — |
| E17 | — | SpA1 70 nm | HATCN 5 nm | SpMA1 90 nm | IC1:TEG1 (90%:10%) 30 nm | — | 3a 40 nm | LiQ 3 nm |
| E18 | — | SpA1 90 nm | HATCN 5 nm | SpMA1 130 nm | 3c:TER1 (92%:8%) 40 nm | — | ST1:LiQ (50%:50%) 40 nm | — |
| E19 | — | SpA1 70 nm | HATCN 5 nm | SpMA1 90 nm | 3g:TEG1 (90%:10%) 30 nm | IC1 10 nm | ST1:LiQ (50%:50%) 30 nm | — |
| E20 | — | SpA1 90 nm | HATCN 5 nm | SpMA1 130 nm | IC1:TEG1 (90%:10%) 40 nm | — | 20:LiQ (50%:50%) 40 nm | — |
| E21 | — | SpA1 90 nm | HATCN 5 nm | SpMA1 130 nm | IC1:TEG1 (90%:10%) 40 nm | — | 20 40 nm | LiF 1 nm |
| E22 | — | SpA1 70 nm | HATCN 5 nm | SpMA1 90 nm | 3:IC2:TEG1 (60%:30%:10%) 40 nm | — | ST1:LiQ (50%:50%) 30 nm | — |
| E23 | — | SpA1 70 nm | HATCN 5 nm | SpMA1 90 nm | 19a:IC1:TEG1 (45%:45%:10%) 30 nm | IC1 10 nm | ST1:LiQ (50%:50%) 30 nm | — |
| E24 | — | SpA1 70 nm | HATCN 5 nm | SpMA1 90 nm | 19a:IC3:TEG1 (45%:45%:10%) 30 nm | — | ST1:LiQ (50%:50%) 40 nm | — |
| E25 | — | SpA1 70 nm | HATCN 5 nm | SpMA1 90 nm | 19a:IC4:TEG1 (45%:45%:10%) 30 nm | IC1 10 nm | ST1:LiQ (50%:50%) 30 nm | — |
| E26 | — | SpA1 90 nm | HATCN 5 nm | SpMA1 130 nm | 19a:TEG1 (90%:10%) 40 nm | — | 19a 40 nm | LiQ 3 nm |
| E27 | — | SpA1 70 nm | HATCN 5 nm | SpMA1 90 nm | 19a:3e:TEG1 (45%:45%:10%) 30 nm | IC1 10 nm | ST1:LiQ (50%:50%) 30 nm | — |
| E28 | — | SpA1 70 nm | HATCN 5 nm | SpMA1 90 nm | 8a:IC2:TEG1 (45%:45%:10%) 40 nm | — | ST1:LiQ (50%:50%) 30 nm | — |
| E29 | — | SpA1 70 nm | HATCN 5 nm | SpMA1 90 nm | 3:ST2:TEG1 (60%:30%:10%) 40 nm | — | ST1:LiQ (50%:50%) 30 nm | — |

TABLE 2

Data of the OLEDs

| Ex. | U1000 (V) | CE1000 (cd/A) | PE1000 (lm/W) | EQE1000 | CIE x/y at 1000 cd/m$^2$ |
|---|---|---|---|---|---|
| V1 | 4.5 | 46 | 33 | 13.0% | 0.33/0.62 |
| V2 | 5.3 | 6.6 | 3.9 | 6.1% | 0.14/0.13 |
| E1 | 4.4 | 48 | 35 | 13.6% | 0.34/0.62 |
| E2 | 4.5 | 48 | 33 | 13.3% | 0.34/0.62 |
| E3 | 4.0 | 51 | 41 | 14.3% | 0.34/0.63 |
| E4 | 4.4 | 8.2 | 5.8 | 7.6% | 0.14/0.13 |
| E5 | 4.3 | 8.7 | 6.4 | 8.1% | 0.14/0.13 |
| E6 | 4.6 | 7.1 | 4.8 | 6.6% | 0.14/0.13 |
| E7 | 3.7 | 55 | 48 | 15.5% | 0.33/0.62 |
| E8 | 3.7 | 55 | 46 | 15.2% | 0.34/0.63 |
| E9 | 4.1 | 52 | 40 | 14.4% | 0.33/0.62 |
| E10 | 3.4 | 59 | 54 | 16.4% | 0.33/0.63 |
| E11 | 3.3 | 58 | 55 | 16.2% | 0.34/0.62 |
| E12 | 3.4 | 56 | 52 | 15.8% | 0.34/0.62 |
| E13 | 3.3 | 63 | 60 | 17.4% | 0.33/0.62 |
| E14 | 4.3 | 11.8 | 8.7 | 12.8% | 0.67/0.33 |

TABLE 2-continued
Data of the OLEDs
| Ex. | U1000 (V) | CE1000 (cd/A) | PE1000 (lm/W) | EQE1000 | CIE x/y at 1000 cd/m² |
|---|---|---|---|---|---|
| E15 | 4.4 | 10.8 | 7.7 | 11.8% | 0.67/0.33 |
| E16 | 3.6 | 54 | 47 | 15.0% | 0.33/0.63 |
| E17 | 3.7 | 57 | 49 | 15.9% | 0.32/0.62 |
| E18 | 4.7 | 10.1 | 6.8 | 11.1% | 0.67/0.33 |
| E19 | 4.5 | 46 | 32 | 12.8% | 0.34/0.62 |
| E20 | 3.3 | 64 | 61 | 17.3% | 0.34/0.62 |
| E21 | 3.8 | 60 | 50 | 16.0% | 0.34/0.62 |
| E22 | 3.8 | 59 | 49 | 15.8% | 0.34/0.63 |
| E23 | 3.8 | 60 | 50 | 16.3% | 0.35/0.62 |
| E24 | 3.7 | 61 | 52 | 16.7% | 0.34/0.62 |
| E25 | 3.5 | 55 | 49 | 15.4% | 0.34/0.62 |
| E26 | 4.4 | 55 | 39 | 15.2% | 0.33/0.62 |
| E27 | 3.6 | 57 | 48 | 15.7% | 0.32/0.62 |
| E28 | 3.2 | 58 | 56 | 16.8% | 0.33/0.63 |
| E29 | 4.2 | 61 | 46 | 16.8% | 0.33/0.63 |
TABLE 3
Structural formulae of the materials for the OLEDs
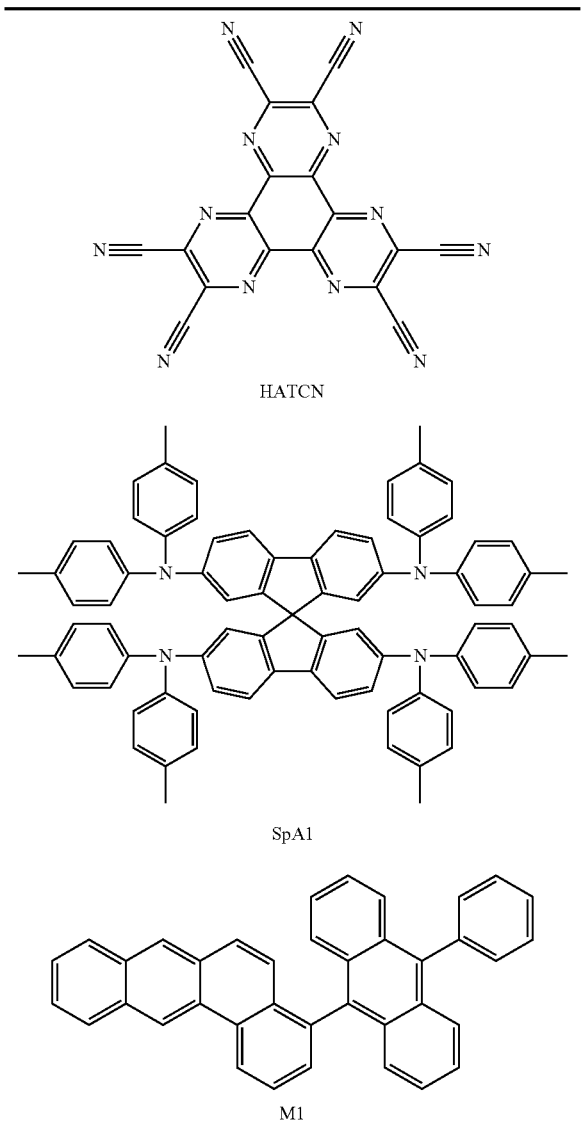
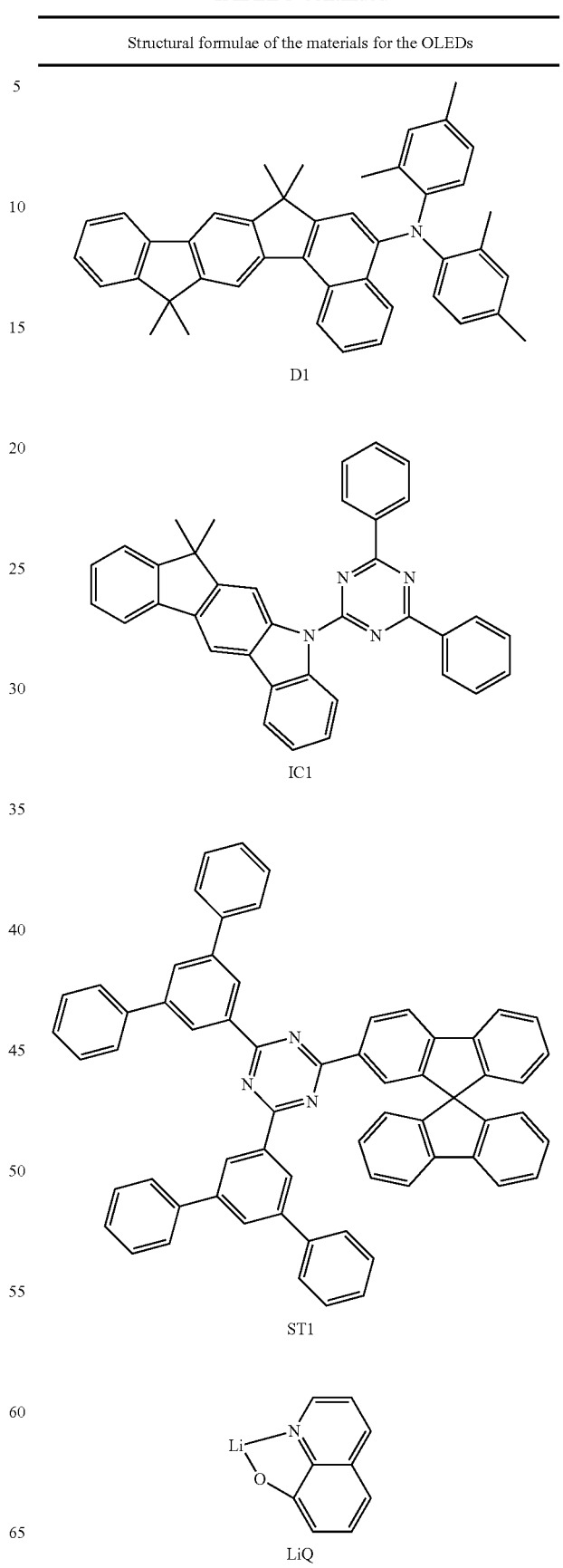

TABLE 3-continued
Structural formulae of the materials for the OLEDs
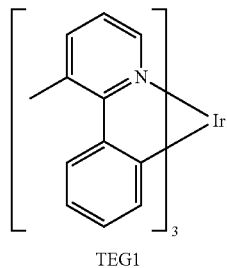
TEG1
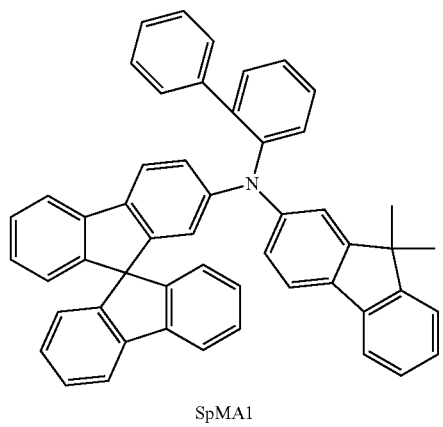 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
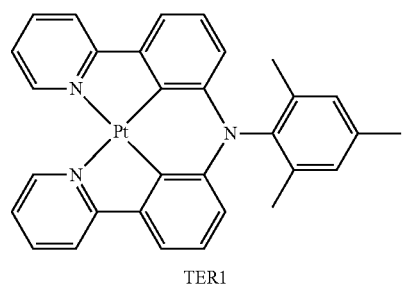
TER1
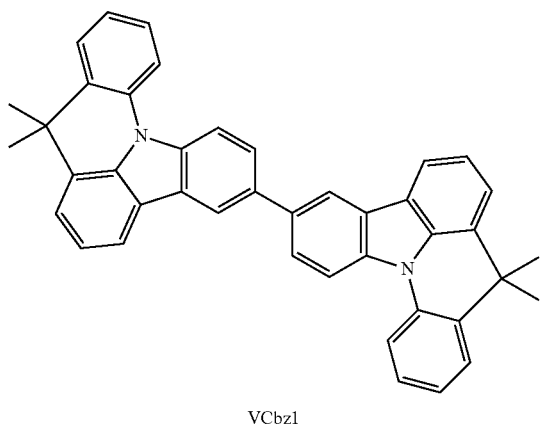
VCbz1
TABLE 3-continued
Structural formulae of the materials for the OLEDs
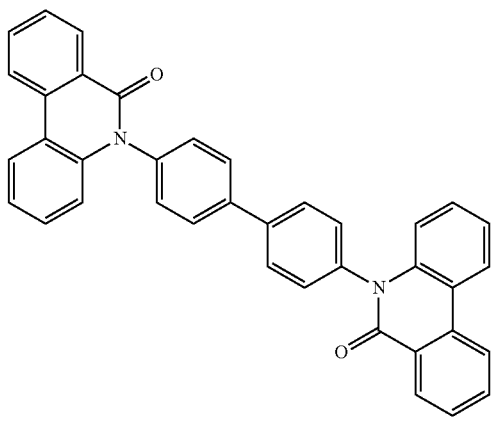
LaDi1 (prior art)
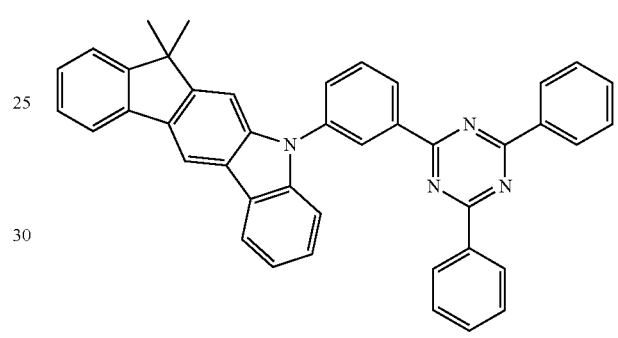
IC2
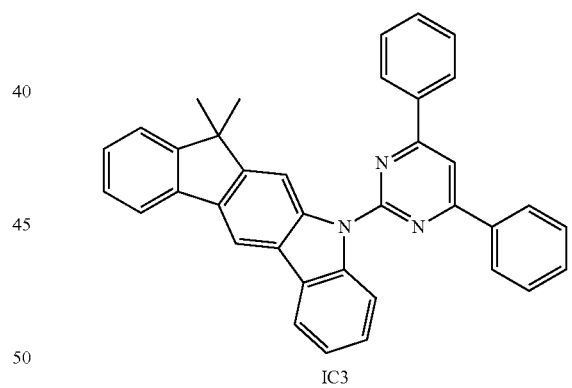
IC3
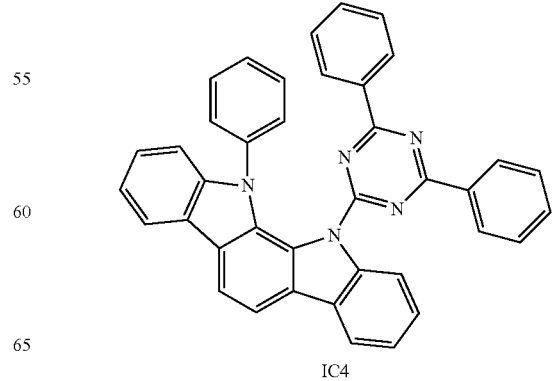
IC4

TABLE 3-continued

Structural formulae of the materials for the OLEDs

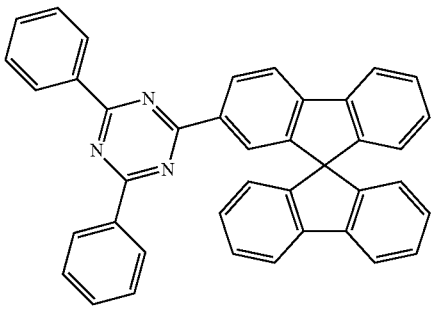

ST2

The invention claimed is:

1. A compound of the formula (11) or formula (12),

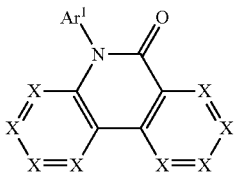

formula (11)

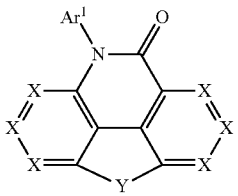

formula (12)

where the following applies to the symbols and indices used:

X is, identically or differently on each occurrence, CR or N; or two adjacent groups X in formula (11) or formula (12) stand for a group of the following formula (9) or (10),

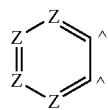

formula (9)

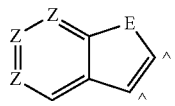

formula (10)

where

E stands for $NR$, $CR_2$, O or S;

Z stands, identically or differently on each occurrence, for CR or N and

^ indicate the corresponding adjacent groups X in formula (11) or formula (12);

$Ar^1$ is an aromatic or heteroaromatic ring system having 5 to 24 aromatic ring atoms, which may be substituted by one or more radicals R and which contains no aryl or heteroaryl groups having more than two aromatic six-membered rings condensed directly onto one another;

Y is $-C(=O)-N(Ar^1)-$, $C(R^1)_2$, or $C(=O)$;

R is selected, identically or differently on each occurrence, from the group consisting of H, D, F, CN, $N(Ar^2)_2$, $C(=O)Ar^2$, a straight-chain alkyl or alkoxy group having 1 to 10 C atoms or a branched or cyclic alkyl or alkoxy group having 3 to 10 C atoms or an alkenyl group having 2 to 10 C atoms, each of which may be substituted by one or more radicals $R^2$, where one or more non-adjacent $CH_2$ groups may be replaced by O and where one or more H atoms may be replaced by D or F, an aromatic or heteroaromatic ring system having 5 to 30 aromatic ring atoms, which may in each case be substituted by one or more radicals $R^2$, or an aryloxy or heteroaryloxy group having 5 to 30 aromatic ring atoms, which may be substituted by one or more radicals $R^2$;

$R^1$ is selected on each occurrence, identically or differently, from the group consisting of H, D, F, Cl, Br, I, CN, $NO_2$, $N(Ar^2)_2$, $N(R^2)_2$, $C(=O)Ar^2$, $C(=O)R^2$, $P(=O)(Ar^2)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent $CH_2$ groups may be replaced by $R^2C=CR^2$, $C=C$, $Si(R^2)_2$, $C=O$, $C=S$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^2$, an aryloxy or heteroaryloxy group having 5 to 60 aromatic ring atoms, which may be substituted by one or more radicals $R^2$, or a combination of these systems, where two or more adjacent substituents R or two or more adjacent substituents $R^1$ may optionally form a monocyclic or polycyclic, aliphatic, aromatic or heteroaromatic ring system, which may be substituted by one or more radicals $R^2$ and which contains no aryl or heteroaryl groups having more than two aromatic six-membered rings condensed directly onto one another; a radical R on $Ar^1$ may furthermore also form an aliphatic ring system with a radical R on Ar; with the proviso that an aryl or heteroaryl group having more than two aryl groups condensed directly onto one another is not formed by ring formation of the radicals R or $R^1$;

$Ar^2$ is on each occurrence, identically or differently, an aromatic or heteroaromatic ring system having 5-30 aromatic ring atoms, which may be substituted by one or more non-aromatic radicals $R^2$ and which contains no aryl or heteroaryl groups having more than two aromatic six-membered rings condensed directly onto one another; two radicals $Ar^2$ which are bonded to the same N atom or P atom may also be bridged to one another here by a single bond or a bridge selected from $N(R^2)$, $C(R^2)_2$ or O;

$R^2$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^2$ may form a mono- or polycyclic, aliphatic, aromatic or heteroaromatic ring system with one another;

n is on each occurrence, identically or differently, 0 or 1, where n=0 means that no group Y is present and instead a substituent R is bonded or a heteroatom of the group Ar is present in the positions on Ar in which Y is bonded in formula (12);

with the proviso that the radicals on Ar¹ do not contain a lactam group the following compounds are excluded from the invention:

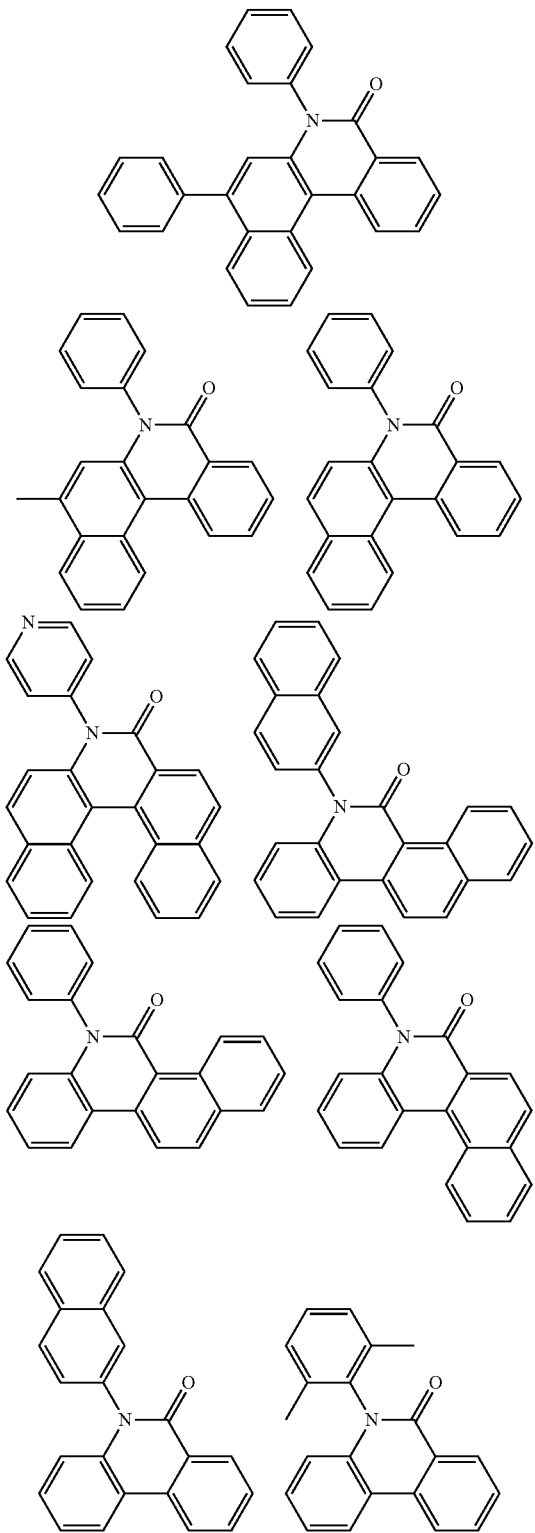

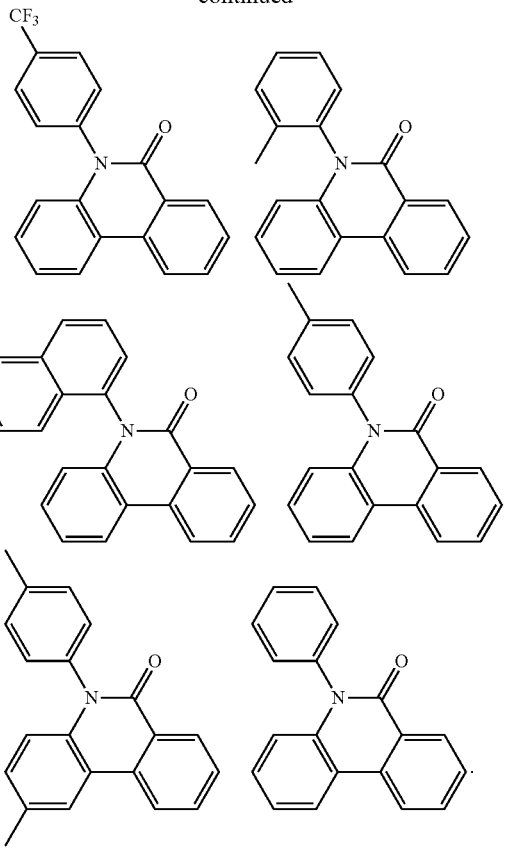

2. Process for the preparation of the compound according to claim 1 comprising:

bond formation between the nitrogen of a lactam and Ar¹;

followed by an oxidation to the corresponding lactum.

3. The electronic device which comprises the compound according to claim 1.

4. The electronic device as claimed in claim 3, wherein the device is an organic electroluminescent device.

5. An electronic device comprising a compound of the formula (11) or (12),

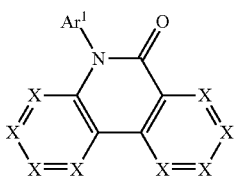

formula (11)

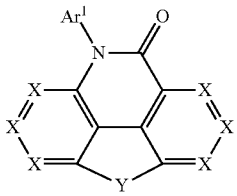

formula (12)

where the following applies to the symbols and indices used:

X is, identically or differently on each occurrence, CR or N; or two adjacent groups X in formula (11) or formula (12) stand for a group of the following formula (9) or (10),

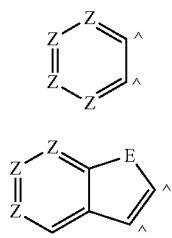

formula (9)

formula (10)

where

E stands for NR, CR$_2$, O or S;

Z stands, identically or differently on each occurrence, for CR or N and

^ indicate the corresponding adjacent groups X in formula (11) or formula (12);

Ar$^1$ is an aromatic or heteroaromatic ring system having 5 to 24 aromatic ring atoms, which may be substituted by one or more radicals R and which contains no aryl or heteroaryl groups having more than two aromatic six-membered rings condensed directly onto one another;

Y is —C(=O)—N(Ar$^1$)—, C(R$^1$)$_2$, or C(=O);

R is selected, identically or differently on each occurrence, from the group consisting of H, D, F, CN, N(Ar$^2$)$_2$, C(=O)Ar$^2$, a straight-chain alkyl or alkoxy group having 1 to 10 C atoms or a branched or cyclic alkyl or alkoxy group having 3 to 10 C atoms or an alkenyl group having 2 to 10 C atoms, each of which may be substituted by one or more radicals R$^2$, where one or more non-adjacent CH$_2$ groups may be replaced by O and where one or more H atoms may be replaced by D or F, an aromatic or heteroaromatic ring system having 5 to 30 aromatic ring atoms, which may in each case be substituted by one or more radicals R$^2$, or an aryloxy or heteroaryloxy group having 5 to 30 aromatic ring atoms, which may be substituted by one or more radicals R$^2$;

R$^1$ is selected on each occurrence, identically or differently, from the group consisting of H, D, F, Cl, Br, I, CN, NO$_2$, N(Ar$^2$)$_2$, N(R$^2$)$_2$, C(=O)Ar$^2$, C(=O)R$^2$, P(=O)(Ar$^2$)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^2$, where one or more non-adjacent CH$_2$ groups may be replaced by R$^2$C=CR$^2$, C≡C, Si(R$^2$)$_2$, C=O, C=S, C=NR$^2$, P(=O)(R$^2$), SO, SO$_2$, NR$^2$, O, S or CONR$^2$ and where one or more H atoms may be replaced by D, F, Cl, Br, I, CN or NO$_2$, an aromatic or heteroaromatic ring system having 5 to 60 aromatic ring atoms, which may in each case be substituted by one or more radicals R$^2$, an aryloxy or heteroaryloxy group having 5 to 60 aromatic ring atoms, which may be substituted by one or more radicals R$^2$, or a combination of these systems, where two or more adjacent substituents R or two or more adjacent substituents R$^1$ may optionally form a monocyclic or polycyclic, aliphatic, aromatic or heteroaromatic ring system, which may be substituted by one or more radicals R$^2$ and which contains no aryl or heteroaryl groups having more than two aromatic six-membered rings condensed directly onto one another; a radical R on Ar$^1$ may furthermore also form an aliphatic ring system with a radical R on Ar; with the proviso that an aryl or heteroaryl group having more than two aryl groups condensed directly onto one another is not formed by ring formation of the radicals R or R$^1$;

Ar$^2$ is on each occurrence, identically or differently, an aromatic or heteroaromatic ring system having 5-30 aromatic ring atoms, which may be substituted by one or more non-aromatic radicals R$^2$ and which contains no aryl or heteroaryl groups having more than two aromatic six-membered rings condensed directly onto one another; two radicals Ar$^2$ which are bonded to the same N atom or P atom may also be bridged to one another here by a single bond or a bridge selected from N(R$^2$), C(R$^2$)$_2$ or O;

R$^2$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents R$^2$ may form a mono- or polycyclic, aliphatic, aromatic, or heteroaromatic ring system with one another;

n is on each occurrence, identically or differently, 0 or 1, where n=0 means that no group Y is present and instead a substituent R is bonded or a heteroatom of the group Ar is present in the positions on Ar in which Y is bonded on formula (12);

with the proviso that the radicals on Ar$^1$ do not contain a lactum group.

6. The electronic device according to claim 5 wherein R, R$^1$ is selected on each occurrence, identically or differently, from the group consisting of H, D, F, Cl, Br, I, CN, NO$_2$, N(Ar$^2$)$_2$, N(R$^2$)$_2$, C(=O)Ar$^2$, C(=O)R$^2$, P(=O)(Ar$^2$)$_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^2$, where one or more non-adjacent CH$_2$ groups may be replaced by R$^2$C=CR$^2$, C≡C, Si(R$^2$)$_2$, C=O, C=S, C=NR$^2$, P(=O)(R$^2$), SO, SO$_2$, NR$^2$, O, S or CONR$^2$ and where one or more H atoms may be replaced by D, F, Cl, Br, I, CN or NO$_2$, an aromatic or heteroaromatic ring system having 5 to 60 aromatic ring atoms, which may in each case be substituted by one or more radicals R$^2$, an aryloxy or heteroaryloxy group having 5 to 60 aromatic ring atoms, which may be substituted by one or more radicals R$^2$, or a combination of these systems, where two or more adjacent substituents R or two or more adjacent substituents R$^1$ may optionally form a monocyclic or polycyclic, aliphatic, aromatic or heteroaromatic ring system, which may be substituted by one or more radicals R$^2$ and which contains no aryl or heteroaryl groups having more than two aromatic six-membered rings condensed directly onto one another; a radical R on Ar$^1$ may furthermore also form an aliphatic ring system with a radical R on Ar; with the proviso that an aryl or heteroaryl group having more than two aryl groups condensed directly onto one another is not formed by ring formation of the radicals R or R$^1$;

and

R$^2$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN.

7. The electronic device according to claim 5, wherein all groups X stand, identically or differently on each occurrence, for CR.

8. The electronic device according claim 5, wherein the compounds of the formula (11) and (12) are selected from the compounds of the formulae (11b), (11c), (11d), (12b), (12c) and (12d),

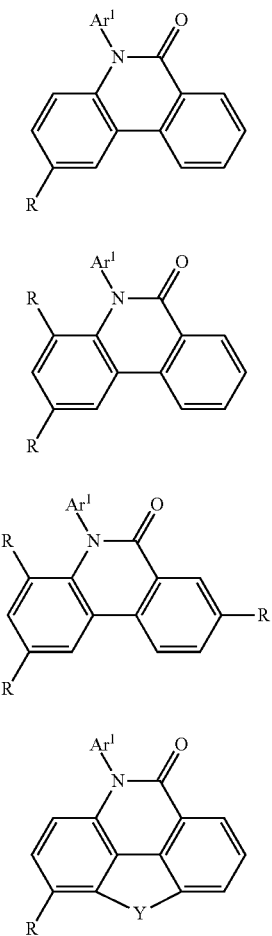

formula (11b)

formula (11c)

formula (11d)

formula (12b)

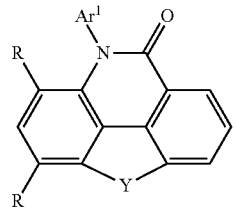

formula (12c)

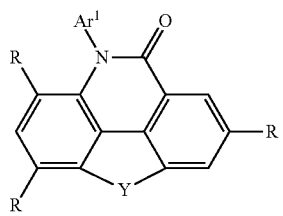

formula (12d)

where the symbols used have the meanings given in claim 5.

9. The electronic device according claim 5, wherein Ar¹ is selected from the group consisting of benzene, ortho-, meta- or para-biphenyl, ortho-, meta-, para- or branched terphenyl, linear or branched quaterphenyl, fluorene, spirobifluorene, carbazole, dibenzothiophene, dibenzofuran, 1,3,5-triazine, pyridine, pyrimidine, indenocarbazole, bridged carbazole or indolocarbazole or a combination of two or three of these groups, where these groups may each also be substituted by one or more radicals R.

10. The electronic device according to claim 5, which is an organic electroluminescent device, wherein the compound of the formula (11) or (12) is employed as matrix material for fluorescent or phosphorescent emitters and/or in a hole-blocking layer and/or in an electron-transport layer and/or in an electron-blocking or exciton-blocking layer and/or in a hole-transport layer and/or in an optical coupling-out layer.

11. The electronic device according to claim 5, selected from the group consisting of organic electroluminescent devices, organic integrated circuits, organic field-effect transistors, organic thin-film transistors, organic light-emitting transistors, organic solar cells, organic dye-sensitised solar cells, organic optical detectors, organic photoreceptors, organic field-quench devices, light-emitting electrochemical cells, organic laser diodes (O-lasers) and organic plasmon emitting devices.

* * * * *